US008133515B2

(12) United States Patent
Boons et al.

(10) Patent No.: US 8,133,515 B2
(45) Date of Patent: Mar. 13, 2012

(54) ALKYNES AND METHODS OF REACTING ALKYNES WITH 1,3-DIPOLE-FUNCTIONAL COMPOUNDS

(75) Inventors: Geert-Jan Boons, Athens, GA (US); Jun Guo, Athens, GA (US); Xinghai Ning, Athens, GA (US); Margaretha Wolfert, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/743,632

(22) PCT Filed: Nov. 21, 2008

(86) PCT No.: PCT/US2008/084345
§ 371 (c)(1),
(2), (4) Date: Aug. 5, 2010

(87) PCT Pub. No.: WO2009/067663
PCT Pub. Date: May 28, 2009

(65) Prior Publication Data
US 2010/0297250 A1    Nov. 25, 2010
US 2012/0040011 A9    Feb. 16, 2012

Related U.S. Application Data

(60) Provisional application No. 61/004,021, filed on Nov. 21, 2007, provisional application No. 61/007,674, filed on Dec. 14, 2007, provisional application No. 61/137,061, filed on Jul. 25, 2008.

(51) Int. Cl.
A61K 9/14       (2006.01)
A61K 31/4192    (2006.01)
A61K 31/423     (2006.01)
A61K 31/4245    (2006.01)
C07C 49/323     (2006.01)
C07C 33/34      (2006.01)
C07C 211/42     (2006.01)
C07C 251/56     (2006.01)
C07C 69/96      (2006.01)
C07C 271/34     (2006.01)
C07C 233/10     (2006.01)
C07D 249/16     (2006.01)
C07D 261/20     (2006.01)
C07D 271/12     (2006.01)
C07D 405/06     (2006.01)
C12N 11/02      (2006.01)
A61P 37/04      (2006.01)
C08G 16/00      (2006.01)

(52) U.S. Cl. ........ 424/501; 435/177; 514/359; 514/364; 514/379; 528/220; 548/126; 548/241; 548/261; 548/304.1; 558/272; 560/115; 564/172; 564/257; 564/427; 568/326; 568/808

(58) Field of Classification Search .......................... None
See application file for complete search history.

(56) References Cited

U.S. PATENT DOCUMENTS

| | | | |
|---|---|---|---|
| 5,874,532 A | 2/1999 | Pieken et al. | |
| 6,255,475 B1 | 7/2001 | Kwiatkowski | |
| 6,737,236 B1 | 5/2004 | Pieken et al. | |
| 7,375,234 B2 | 5/2008 | Sharpless et al. | |
| 7,427,678 B2 | 9/2008 | Pieken et al. | |
| 7,763,736 B2 | 7/2010 | Sharpless et al. | |
| 2005/0032081 A1 | 2/2005 | Ju et al. | |
| 2006/0147963 A1 | 7/2006 | Barone et al. | |
| 2009/0215635 A1 | 8/2009 | Carell et al. | |

FOREIGN PATENT DOCUMENTS

| | | |
|---|---|---|
| WO | WO 96/09316 A1 | 3/1996 |
| WO | WO 96/20289 A1 | 7/1996 |
| WO | WO 96/34984 A1 | 11/1996 |
| WO | WO 98/30575 A1 | 7/1998 |
| WO | WO 02/29003 A2 | 4/2002 |
| WO | WO 02/29003 A3 | 7/2002 |
| WO | WO 03/101972 A1 | 12/2003 |
| WO | WO 2004/018497 A2 | 3/2004 |
| WO | WO 2004/018497 A3 | 6/2004 |
| WO | WO 2006/038184 A2 | 4/2006 |
| WO | WO 2006/038184 A3 | 6/2006 |
| WO | WO 2006/117161 A2 | 11/2006 |
| WO | WO 2006/117161 A3 | 1/2007 |
| WO | WO 2007/039858 A2 | 4/2007 |
| WO | WO 2008/101024 A2 | 8/2008 |
| WO | WO 2008/101024 A3 | 10/2008 |

OTHER PUBLICATIONS

Ning et al., Angewandte Chemie International Edition, 2008, 47, 2253-2255.*
Ning et al., caplus an 2008:409852.*
International Search Report and Written Opinion issued by the European Search Authority on Apr. 22, 2009 for International Application No. PCT/US2008/084345; 11 pgs.
International Preliminary Report on Patentability issued by the International Bureau of WIPO on Jun. 3, 2010 for International Application No. PCT/US2008/084345; 9 pgs.
Agard et al., "A strain-promoted [3 +2} azide-alkyne cycloaddition for covalent modification of biomolecules in living systems," *J of Amer. Chem Society*, Nov. 24, 2004; 126(46):15046-15047.
Agard et al., "A comparative Study of Bioorthogonal Reactions with Azides," *ACS Chemical Biology*, Nov. 10, 2006;1(10):644-648.
"Azide alkyne Huisgen cycloaddition," *Wikipedia*, [online]. Downloaded Nov. 19, 2007 from http://en.wikipedia.org/wiki/Azide_alkyne_Huisgen_cycloaddition> 3 pgs.
Bantscheff et al., "Quantitative mass spectrometry in proteomics: a critical review," *Anal. Bioanal. Chem.*, 2007;389:1017-1031.

(Continued)

Primary Examiner — Sun Jae Loewe
(74) Attorney, Agent, or Firm — Mueting, Raasch & Gebhardt, P.A.

(57) ABSTRACT 1,3-Dipole-functional compounds (e.g., azide functional compounds) can be reacted with certain alkynes in a cyclization reaction to form heterocyclic compounds. Useful alkynes (e.g., strained, cyclic alkynes) and methods of making such alkynes are also disclosed. The reaction of 1,3-dipole-functional compounds with alkynes can be used for a wide variety of applications including the immobilization of biomolecules on a substrate.

24 Claims, 23 Drawing Sheets

OTHER PUBLICATIONS

Baskin et al., "Bioorthogonal Click Chemistry: Covalent Labeling in Living Systems," *QSAR Comb. Sci.*, 2007;26:1211-1219.

Baskin et al., "Copper-Free click chemistry for dynamic in vivo imaging," *Proc. Natl. Acad Sci.* USA, Oct. 23, 2007;104(43):16793-16797.

Binder et al., "'Click' Chemistry in Polymer and Material Science: An Update," *Macromol. Rapid Commun.*, 2008;29:952-981.

Blixt et al., "Enzymatic Glycosylation of reducing oligosaccharides linked to a solid phase or a lipid via a cleavable squarate linker," *Carbohydr. Res.*, Jun. 30, 1999;319(1-4):80-91.

Boons, Geert-Jan, "Site-Specific Glycosylation of Glycolylated Human IGG-FC Antibodies," Grant Abstract, Grant No. 2P41RR005351-160092 [online]. National Institutes of Health, project dates Apr. 4, 2005 to Jan. 31, 2006 [retrieved on Jul. 25, 2008]. Retrieved from the Internet:<URL: http://crip.cit.nih.gov/crisp/CRISP...>; 1 pg.

Boons, Geert-Jan, "New Synthetic Endotoxin Antagonists," Grant Abstract, Grant No. 2P41RR005351-160093 [online]. National Institutes of Health, project dates Apr. 4, 2005 to Jan. 31, 2006 [retrieved on Jul. 25, 2008]. Retrieved from the Internet:<URL:http://crip.cit.nih.gov/crisp/CRISP...>; 1 pg.

Boons, Geert-Jan, "The Role of Multivalency in the mode-of-action," Grant Abstract, Grant No. 2P41RR005351-160096 [online]. National Institutes of Health, project dates Apr. 4, 2005 to Jan. 31, 2006 [retrieved on Jul. 25, 2008]. Retrieved from the Internet:<URL: http://crip.cit.nih.gov/crisp/Crisp...>; 1 pg Boons, Geert-Jan, "Modulation of Biological Functions with Synthetic Glycoconjugates," Department of Basic Sciences and Environment Seminar, Oct. 8, 2008. [Online]. [retrieved on Oct. 10, 2008]. Retrieved from the Internet:<URL:http://www.igm/life.ku.dk/Aktiviteter/2008_10_08_Boons_Seminar.aspx>; 1 pg.

Chin et al., "An Expanded Eukaryotic Genetic Code," *Science*, Aug. 15, 2003;301:964-967.

Choi et al., "Surface Modification of Functional Nanoparticles for Controlled Drug Delivery," *J Dispersion Sci. Tech.*, 2003;24:475-487.

Codelli et al., "Second-Generation Difluorinated Cyclooctynes for Copper-Free Click Chemistry," *J Am Chem Soc.*, 2008;130:11486-11493.

Dedola et al., "Recent Applications of the $Cu^I$-catalysed Huisgen azide-alkyne 1,3-dipolar cycloaddition reaction in carbohydrate chemistry," *Org. Biomol. Chem.*, 2007;5:1006-1017.

Dicken et al., "Reactions at High Pressures. [3 +2] Dipolar Cycloaddition of Nitrones with Vinyl Esters," *J Org. Chem.*, 1982;47:2047-2051.

Du et al., "Phenacyl esters as a new photocleavable linker in liquid-phase chemistry," *Tetrahedron. Lett.*, 2005;46(19):3399-3402.

Ess et al., "Transition States of Strain-Promoted Metal-Free Click Chemistry: 1,3-Dipolar Cycloadditions of Phenyl Azide and Cyclooctynes," *Organic Lett.*, 2008;10(8):1633-1636.

Gaucher et al., "Block copolymer micelles: preparation, characterization and application in drug delivery," *J Control Release*, 2005;109:169-188.

Gierlich et al., "Click Chemistry as a Reliable Method for the High-Density Postsynthetic Functionalization of Alkyne-Modified DNA," *Organic Lett.*, 2006;8(17):3639-3642.

Glatthar et al., "A New Photocleavable Linker in Solid-Phase Chemistry for Ether Cleavage," *Organic Lett.*, 2000;2(15):2315-2317.

Gupta et al., "Mild and Safe procedure for hydrolyzing oximes: Improved synthesis of 1,2-Indandione," *J Pharmaceutical Sci*, Jan. 2006;65(1):134-135.

Hanson et al., "Tailored glycoproteomics and glycan site mapping using saccharideselective bioorthogonal probes," *J. Am. Chem. Soc.*, Jun. 13, 2007;129923):7266-7267.

Hojfeldt et al., "A Cleavable Amino-Thiol Linker for Reversible Linking of Amines to DNA," *J Org. Chem*, 2006;71:9556-9559.

Inouye et al., "The Configurations of $N$-Methyl and $N$-$t$-Butyl-$\alpha$-methoxycarbonylmethanimine $N$-Oxides," *Bull. Chem. Soc.* Japan, 1983;56:3541-3542.

Johnson et al., "Copper-Free click chemistry for the *in situ* crosslinking of photodegradable star polymers," *Chem. Commun.*, 2008;3064-3066.

Jung et al., "Direct Synthesis of Dibenzocyclooctadienes via Double Ortho Friedel-Crafts Alkylation by the Use of Aldehyde-Trimethylsilyl Iodide Adducts," *J Org. Chem.*, 1978;43(19):3698-3701.

Jung and Miller, "Total Synthesis of Isopavine and Intermediates for the Preparation of Substituted Amitriptyline Analogues: Facile Routes to Substituted Dibenzocyclooctatrienes and Dibenzocycloheptatrienes," *J Am. Chem. Soc.*, 1981;103:1984-1992.

Keller et al., "A Thermally-cleavable linker for solid-phase synthesis," *Tetrahedron. Lett.*, 2005;46:1181-1184.

Kho et al., "A tagging-via-substrate technology for detection and proteomics of farnesylated proteins," *Proc. Natl Acad. Sci.* USA, Aug. 24, 2004;101(34):12479-12484.

Kolb and Sharpless, "The growing impact of click chemistry on drug discovery," *Drug Discovery Today*, Dec. 24, 2003;8(24):1128-1137.

Lau et al., "Capture and analysis of quantitative proteomic data," *Proteomics*, 2007;7:2787-2799.

Laughlin et al., "In Vivo Imaging of Membrane-Associated Glycans in Developing Zebrafish," *Science*, 2008;320:664-667.

Lavasanifar et al., "Poly(ethylene oxide)-*block*-poly($_L$-amino acid) micelles for drug delivery," *Adv. Drug Delivery Rev.*, 2002;54:169-190.

Link et al., "Cell surface labeling of *Escherichia coli* via copper(I)-catalyzed (3+2) cycloaddition," *J of Amer. Chem Society*, Sep. 17, 2003;125(37):11164-11165.

Link et al., "Discovery of aminoacyl-tRNA synthetase activity through cell-surface display of noncanonical amino acids," *Proc. Natl. Acad. Sci.* USA, Jul. 5, 2006;103(27):10180-10185.

Luchansky and Bertozzi, "Azido Sialic Acids Can Modulate Cell-Surface Interactions," *Chem BioChem.*, 2004;5:1706-1709.

More et al., "Rate and equilibrium constants for formation and hydrolysis of 9-formylfluorene oxime: diffusion-controlled trapping of a protonated aldehyde by hydroxylamine," *Canadian J of Chemistry*, 2000;78(12):1594-1612.

Moses and Moorhouse, "The growing applications of click chemistry," *Chem Soc Rev*, 2007;36:1249-1262.

Murata et al., "A novel linker for solid-phase synthesis cleavable under neutral conditions," *Tetrahedron. Lett.*, 2006;2147-2150.

Nandivada et al., "Click Chemistry: Versatility and Control in the Hands of Materials Scientists," *Adv Mater.*, 2007;19:2197-2208.

Ning et al., "Visualizing Metabolically Labeled Glycoconjugates of Living Cells by Copper-Free and Fast Huisen Cycloaddition," *Angew Chem Int Ed.*, Feb. 14, 2008;47:2253-2255.

Nishiyama et al., "Nanostructured Devices based on Block Copolymer Assemblies for Drug Delivery: Designing Structures for Enhanced Drug Function," *Adv. Polym. Sci.*, 2006;193:67-101.

Parker et al., "Photocleavable peptide hydrogel arrays for MALDI-TOF analysis of kinase activity," *Analyst*, 2006;131:1097-1104.

Paulick et al., "Cleavable Hydrophilic Linker for One-Bead-One-Compound Sequencing of Oligomer Libraries by Tandem Mass Spectrometry," *J Comb. Chem.*, 2006;8(3):417-426.

Piggott et al., "Synthesis of a new hydrophilic o-nitrobenzyl photocleavable linker suitable for use in chemical proteomics," *Tetrahedron Lett.*, 2005;46:8241-8244.

Prescher et al., "Chemistry in Living Systems," *Nature Chemical Biology*, Jun. 1, 2005;1(1):13-21.

Reents et al., "Enzymatically cleavable linker groups in polymer-supported synthesis," *Combinatorial Chem.*, Jan. 2002;7(1):71-76.

Rösler et al., "Advanced drug delivery devices via self-assembly of amphiphilic block copolymers," *Adv. Drug Delivery Rev.*, 2001;53:95-108.

Rostovtsev et al., "A Stepwise Huisgen Cycloaddition Process: Copper (I)-Catalyzed Regioselective 'Ligation' of Azides and Terminal Alkynes," *Angew. Chem.*; Jul. 15, 2002;114(14):2708-2711.

Rostovtsev et al., "A Stepwise Huisgen Cycloaddition Process: Copper (I)-Catalyzed Regioselective 'Ligation' of Azides and Terminal Alkynes," *Angew. Chem. Intl Ed.*, 2002;41(14):2596-2599.

Ruebner et al., "A cyclodextrin dimmer with a photocleavable linker as a possible carrier for the photosensitizer in photodynamic tumor therapy," *Proc Natl Acad Sci USA*, Dec. 21, 1999;96(26):14692-14693

Russell et al., "Thermally cleavable safety-catch linkers for solid phase chemistry," *Tetrahedron Lett.*, 2000;41:5287-5290.

Seitz et al., "5,6-Didehydro-11,12-dihydrobenzo[a,e]cycloocten," *Angew. Chem.*, 1969;81(11):427-428.

Seitz et al., "5,6-Didehydro-11,12-dihydrobenzo[a,e]cycloocten," Angew Chem Int. Ed Engl., 1969;8(6):447-448.

Shimkus et al., "A chemically cleavable biotinylated nucleotide: Usefulness in the recovery of protein-DNA complexes from avidin affinity columns," *Proc Natl Acad Sci USA*, May 1985;82:2593-2597.

Sivakumar et al., "A fluorogenic 1,3-Dipolar Cycloaddition Reaction of 3-Axidocoumarins and Acetylenes," *Org. Lett.*, 2004;6(24):4603-4606.

Sletten et al., "A Hydrophilic Azacyclooctyne for Cu-Free Click Chemistry," *Organic Letters*, 2008;10(14):3097-3099.

Speers et al., "Activity-Based Protein Profiling in Vivo Using a Copper (I)-Catalyzed Azide-Alkyne [3+2] Cycloaddition," *J. Am. Chem. Soc.*, 2003;125:4686-4687.

Sun et al., "Carbohydrate and Protein Immobilization onto Solid Surfaces by Sequential Diels-Alder and Azide-Alkyne Cycloadditions," *Bioconjugate Chem.*, 2006;17:52-57.

Tao, "Soluble polymer-based isotopic labeling (SoPIL): a new strategy to discover protein biomarkers?," *Expert Rev. Proteomics*, Oct. 2007;4(5):603-607.

Tornoe et al., "Peptidotriazoles on Solid Phase: [1,2,3]-Triazoles by Regiospecific Copper(I)-Catalyzed 1,3-Dipolar Cycloadditions of Terminal Alkynes to Azides," *J Org. Chem*. 2002;67:3057-3064.

Turner et al., "Heats of Hydrogenation. IX. Cyclic Acetylenes and Some Miscellaneous Olefins," *J Am. Chem. Soc.*, Feb. 7, 1973;95(3):790-792.

Van Berkel et al., "Metal-Free Triazole Formation as a Tool for Bioconjugation," *ChemBioChem*, 2007;8:1504-1508.

Verhelst et al., "A Mild Chemically Cleavable Linker System for Functional Proteomic Applications," *Angew. Chem.*, 2007;119:1306-1308.

Verhelst et al., "A Mild Chemically Cleavable Linker System for Functional Proteomic Applications," *Angew. Chem. Int Ed.*, 2007;46:1284-1286.

Wang et al., "Bioconjugation by Copper(I)-Catalyzed Azide-Alkyne [3+2] Cycloaddition," *J Am Chem Soc.*, 2003;125:3192-3193.

Wu and Fokin, "Catalytic Azide-Alkyne Cycloaddition: Reactivity and Applications," *Aldrichimica Acta*, 2007;40(1):7-17.

Xiao et al., "A Cyclitively Cleavable Linker for Alcohols: Linker Preparation and Cleavage Conditions," *J Comb. Chem.*, 1999;1(5):379-382.

Antos et al., "Transition metal catalyzed methods for site-selective protein modification," *Current Opinion in Chemical Biology*, Jun. 2006; 10: 253-262. Available online May 12, 2006.

Becer et al. "Click Chemistry beyond Metal-Catalyzed Cycloaddition", *Angew. Chem. Int. Ed.*, 2009, 48:4900-4908. Available online May 27, 2009.

DeClercq et al., "(E)-5-(2-Bromovinyl)-2'-deoxyuridine: A potent and selective anti-herpes agent," *Proc. Natl. Acad. Sci. USA*, Jun. 1979; 76(6): 2947-2951.

Hassane et al., "Targeted Liposomes: Convenient Coupling of Ligands to Preformed Vesicles Using 'Click Chemistry,'" *Bioconjugate Chem.*, 2006; 17: 849-854. Available online Apr. 18, 2006.

International Preliminary Report on Patentability issued Aug. 19, 2009 by the PCT, Patent Application Publication No. PCT/US2008/053870, filed Feb. 13, 2008.

Langenhan et al., "Recent Carbohydrate-Based Chemoselective Ligation Applications," *Current Organic Synthesis*, Jan. 2005; 2(1): 59-81.

Ötvös et al., "Base Modified Oligodeoxynucleotides. II. Increase of Stability to Nucleases by 5-Alkyl-, 5-(1-Alkenyl)-, and 5-(1-Alkynyl)-pyrimidines," *Nucleosides, Nucleotides and Nucleic Acids*, 1999; 18(9): 1929-1933.

Rodionov et al., "Mechanism of the Ligand-Free $Cu^1$-Catalyzed Azide-Alkyne Cycloaddition Reaction," *Angew. Chem. Int. Ed.*, Apr. 4, 2005; 44(15): 2210-2215. Available online Feb. 3, 2005.

Speers et al., "Profiling Enzyme Activities In Vivo Using Click Chemistry Methods," *Chemistry and Biology*, Apr. 2004; 11: 535-546.

"Telomerase PCR ELISA," *Biochemica*, 1996; 4: 7-8.

"TRAPeze® Telomerase Detection Kit S7700," Chemicon International, copyright 2003-2005, cover pages, table of contents, and 1-39.

* cited by examiner 1  2  3

10

11

12

13 a)

b)

(61) 2.17 M$^{-1}$s$^{-1}$ (CH$_3$CN/H$_2$O)
0.27 M$^{-1}$s$^{-1}$ (CD$_3$OH)

(62) 0.0365 M$^{-1}$s$^{-1}$ CH$_3$CN/H$_2$O)

(63) 0.24 M$^{-1}$s$^{-1}$ (CD$_3$CN/D$_2$O)

(64) 0.22 M$^{-1}$s$^{-1}$ (CD$_3$CN/D$_2$O)

(65) 0.08 M$^{-1}$s$^{-1}$ (CD$_3$CN/D$_2$O)

(66) 0.92 M$^{-1}$s$^{-1}$ (CD$_3$CN/D$_2$O)

(67) 0.27 M$^{-1}$s$^{-1}$ (CD$_3$OH)

(68) 0.08 M$^{-1}$s$^{-1}$ (CD$_3$OH))

A.

B.

| Nitrone starting material | reaction time | The second-order rate constant |
|---|---|---|
|  91 | 1.5 h | 0.0515 |
|  92 | 1 h | 0.0721 |
|  93 | 20 min | 0.6721 |
|  94 | 3 min | too fast to measure |
|  95 | 3.5 h | 0.0127 |

ALKYNES AND METHODS OF REACTING ALKYNES WITH 1,3-DIPOLE-FUNCTIONAL COMPOUNDS

This application is the §371 U.S. National Stage of International Application No. PCT/US2008/084345, filed 21 Nov. 2008, which claims the benefit of U.S. Provisional Application Nos. 61/004,021, filed Nov. 21, 2007; 61/007,674, filed Dec. 14, 2007; and 61/137,061, filed Jul. 25, 2008, all of which are hereby incorporated by reference in their entireties.

GOVERNMENT FUNDING

The present invention was made with government support under a grant from the Research Resource Center for Biomedical Complex Carbohydrates of the National Institutes of Health (Grant No. P41-RR-5351). The Government has certain rights in this invention.

BACKGROUND

Bioorthogonal reactions are reactions of materials with each other, wherein each material has limited or substantially no reactivity with functional groups found in vivo. The efficient reaction between an azide and a terminal alkyne, i.e., the most widely studied example of "click" chemistry, is known as a useful example of a bioorthogonal reaction. In particular, the Cu(I) catalyzed 1,3-dipolar cyclization of azides with terminal alkynes to give stable triazoles (e.g., Binder et al., *Macromol. Rapid Commun.* 2008, 29:952-981) has been employed for tagging a variety of biomolecules including proteins, nucleic acids, lipids, and saccharides. The cycloaddition has also been used for activity-based protein profiling, monitoring of enzyme activity, and the chemical synthesis of microarrays and small molecule libraries.

An attractive approach for installing azides into biomolecules is based on metabolic labeling whereby an azide containing biosynthetic precursor is incorporated into biomolecules using the cells' biosynthetic machinery. This approach has been employed for tagging proteins, glycans, and lipids of living systems with a variety of reactive probes. These probes can facilitate the mapping of saccharide-selective glycoproteins and identify glycosylation sites. Alkyne probes have also been used for cell surface imaging of azide-modified bio-molecules and a particularly attractive approach involves the generation of a fluorescent probe from a non-fluorescent precursor by a [3+2] cycloaddition.

Despite the apparent utility of reacting an azide with a terminal alkyne, applications in biological systems using this reaction have been practically limited by factors including the undesirable presence of a copper catalyst. Thus, there is a continuing, unmet need for new bioorthogonal reactions.

SUMMARY

In one aspect, the present invention provides an alkyne, and methods of making an alkyne. In one embodiment, the alkyne is of the formula:

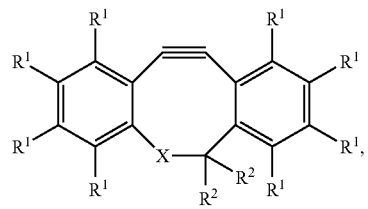

Formula I wherein: each $R^1$ is independently selected from the group consisting of hydrogen, halogen, hydroxy, alkoxy, nitrate, nitrite, sulfate, and a C1-C10 organic group; each $R^2$ is independently selected from the group consisting of hydrogen, halogen, hydroxy, alkoxy, nitrate, nitrite, sulfate, and a C1-C10 organic group; X represents C=O, C=N—$OR^3$, C=N—$NR^3R^4$, $CHOR^3$, or $CHNHR^3$; and each $R^3$ and $R^4$ independently represents hydrogen or an organic group (e.g., which can include a cleavable linker). Also provided are blends of certain alkynes with a polymer or a copolymer that can optionally form a copolymer micelle, which can be useful, for example, for controlling the delivery of drugs as described herein.

In another embodiment, the alkyne includes: a cleavable linker fragment including at least two ends; an alkyne fragment attached to a first end of the cleavable linker fragment; and a biotinylated fragment attached to a second end of the cleavable linker fragment. In preferred embodiments, the alkyne fragment includes a strained, cyclic alkyne fragment. In certain embodiments, the alkyne further includes at least one heavy mass isotope. Optionally, the alkyne further includes at least one detectable label such as a fluorescent label.

Alkynes such as those described herein above can be reacted with at least one 1,3-dipole-functional compound (e.g., an azide-functional compound, a nitrile oxide-functional compound, a nitrone-functional compound, an azoxy-functional compound, and/or an acyl diazo-functional compound) in a cyclization reaction to form a heterocyclic compound, preferably in the substantial absence of added catalyst (e.g., Cu(I)). Optionally, the reaction can take place within or on the surface of a living cell. In certain embodiments, the at least one 1,3-dipole-functional compound includes a 1,3-dipole-functional biomolecule such as a peptide, protein, glycoprotein, nucleic acid, lipid, saccharide, oligosaccharide, and/or polysaccharide. Optionally, the 1,3-dipole-functional biomolecule includes a detectable label such as an affinity label. The heterocyclic compounds formed by the alkyne with the at least one 1,3-dipole-functional compound are also disclosed herein. In certain embodiments, the reaction between the alkyne and the at least one 1,3-dipole-functional compound can take place within or on the surface of a living cell.

For embodiments in which the heterocyclic compound includes a biotinylated fragment, the heterocyclic compound can be bound to a compound that binds biotin, such as avidin and/or streptavidin.

In another aspect, the present invention provides a substrate having an alkyne as described herein on the surface thereof. The substrate can be in the form of a resin, a gel, nanoparticles, or combinations thereof. Optionally, the substrate is a three-dimensional matrix. In preferred embodiments, the X group of an alkyne of Formula I represents a point of attachment to the surface of the substrate. Such substrates can be useful for immobilizing biomolecules such as peptides, proteins, glycoproteins, nucleic acids, lipids, saccharides, oligosaccharides, and/or polysaccharides. Articles including an immobilized biomolecule, such as a protein immobilized on a three-dimensional matrix, are also disclosed herein.

The compositions and methods disclosed herein can offer advantages over bioorthogonal reactions known in the art. See, for example, Baskin et al., *QSAR Comb. Sci.* 2007, 26:1211-1219. For example, alkynes of Formula I as described herein (e.g., wherein X represents C=O, C=N—OR$^3$, C=N—NR$^3$R$^4$, CHOR$^3$, or CHNHR$^3$; and each R$^3$ and R$^4$ independently represents hydrogen or an organic group) surprisingly have been found to have higher reactivity towards 1,3-dipole-functional compounds than other strained, cyclic alkynes (e.g., wherein X represents CH$_2$). See, for example, Codelli, et al., *J. Am. Chem. Soc.* 2008, 130:11486-11493; Johnson et al., *Chem. Commun.* 2008, 3064-3066; Sletten et al., *Organic Letters* 2008, 10:3097-3099; and Laughlin et al., *Science* 2008, 320:664-667. Further, convenient methods having the flexibility to prepare a wide variety of alkynes of Formula I are disclosed herein. In addition, alkynes of Formula I have the capability of reacting not only with azides, but also a variety of other 1,3-dipole-functional compounds.

Definitions:

The term "comprises" and variations thereof do not have a limiting meaning where these terms appear in the description and claims.

As used herein, "a," "an," "the" "at least one," and "one or more" are used interchangeably.

As used herein, the term "or" is generally employed in the sense as including "and/or" unless the context of the usage clearly indicates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

N-{2-[2-(2-amino-ethoxy)-ethoxy]-ethyl}-2-aminooxy-acetamide, AcOH, 1:1 DCM/MeOH, 63%.

Figure 15:
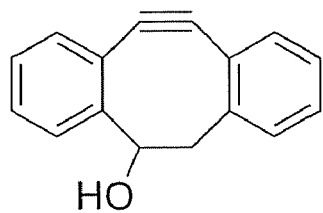
Figure 15:
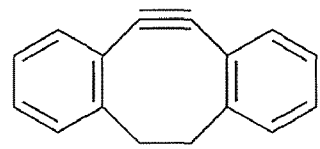
Figure 15:
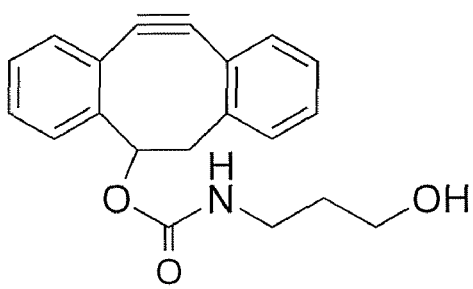
Figure 15:
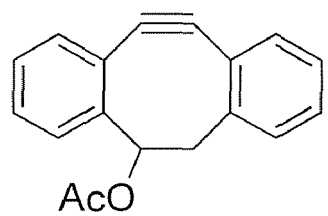
Figure 15:
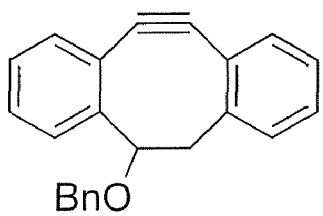
Figure 15:
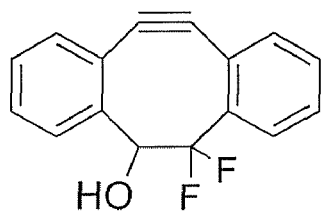
Figure 15:
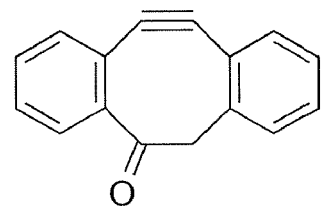
Figure 15:
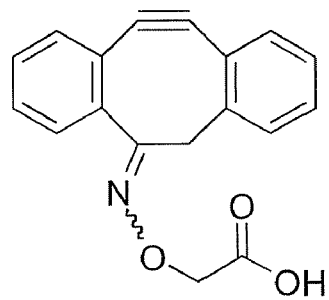

FIG. 15 illustrates compounds 61-68 and second order constants.

Figure 16:
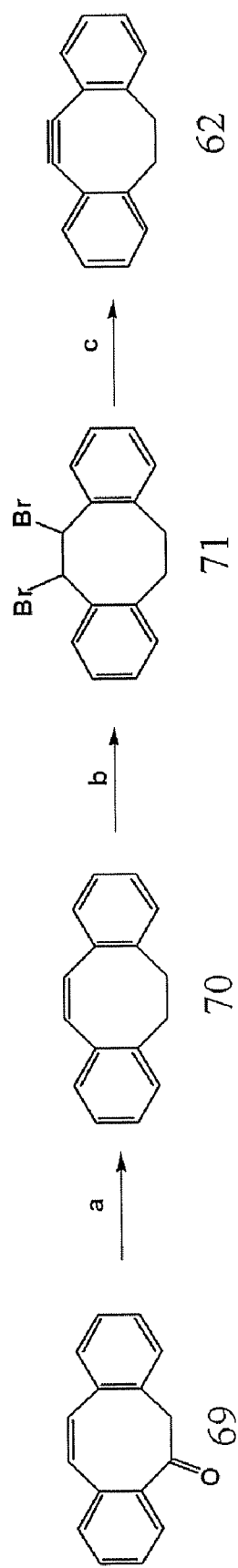

FIG. 16 illustrates scheme 7: exemplary reagents and conditions: a) LiAlH$_4$, AlCl$_3$, Et$_2$O, 0° C., 61%; b) Br$_2$, CHCl$_3$, 0° C., 58%; c) potassium t-butoxide (t-BuOK), THF, room temperature, 25%.

Figure 17:
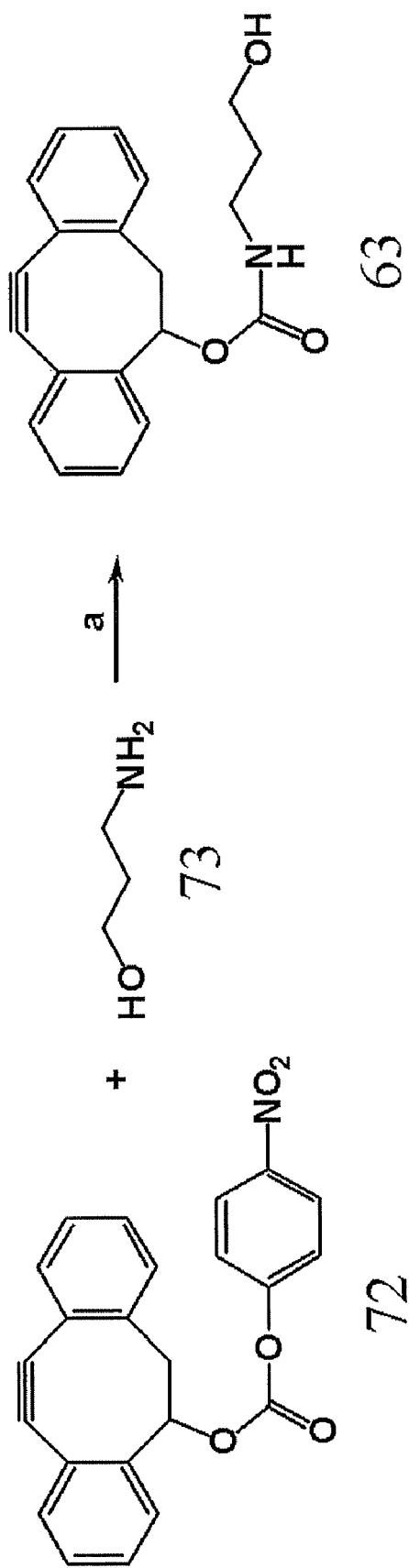

FIG. 17 illustrates scheme 8: exemplary reagents and conditions: a) TEA, CH$_2$Cl$_2$, room temperature, 77%.

Figure 18:
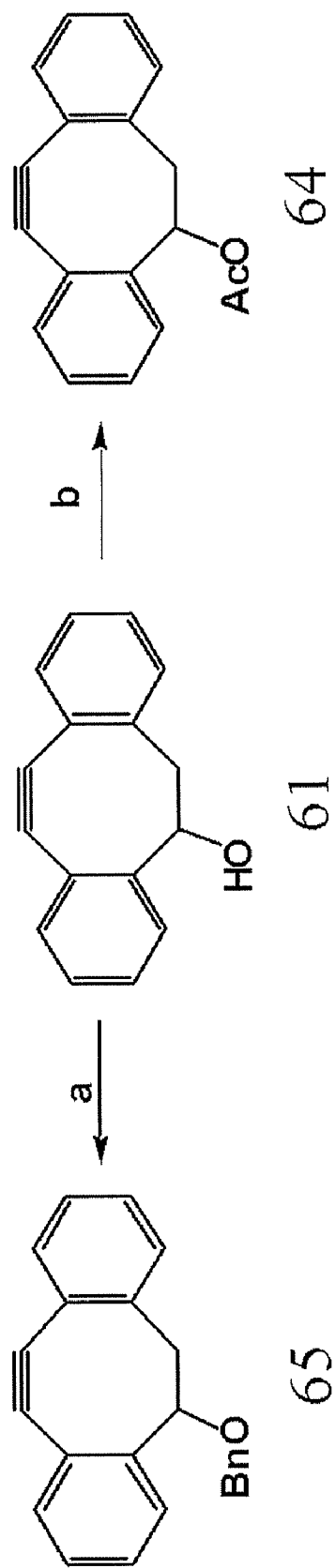

FIG. 18 illustrates scheme 9: exemplary reagents and conditions: a) NaH, benzyl bromide, DMF, room temperature, 59%; b) acetic anhydride (Ac$_2$O), pyridine, room temperature, 81%.

Figure 19:
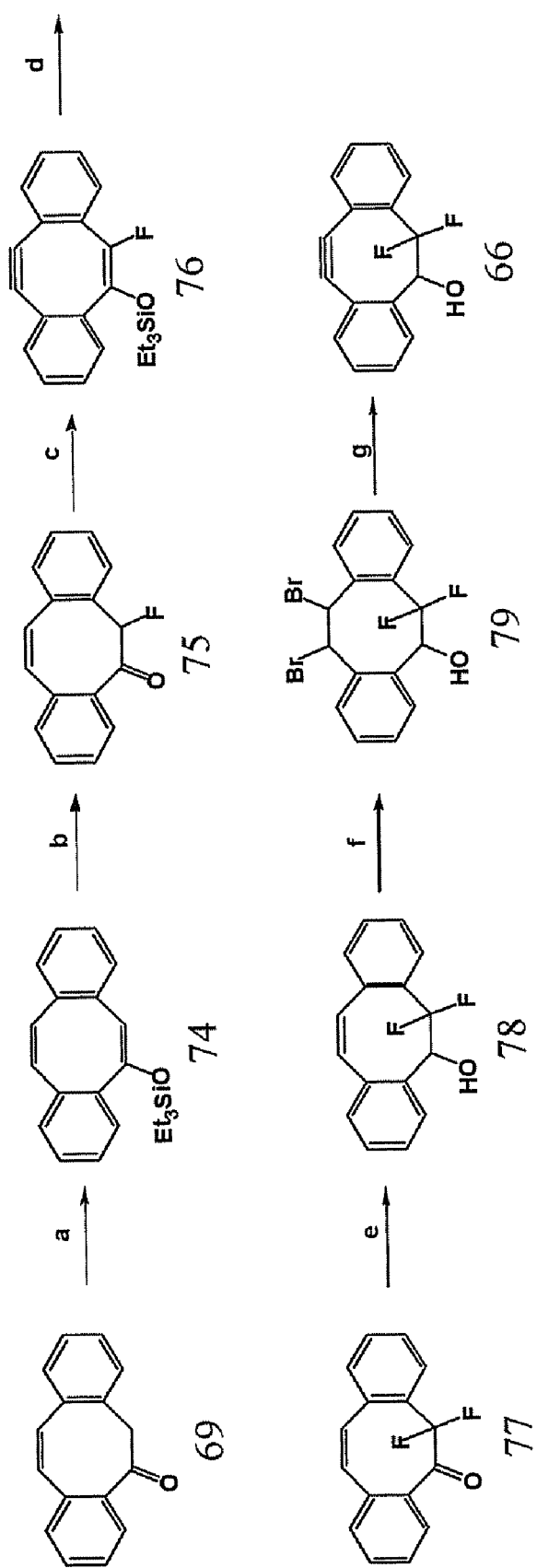

FIG. 19 illustrates scheme 10: exemplary reagents and conditions: a) LDA, Et$_3$SiCl, THF, room temperature, 85%; b) SELECTFLUOR fluorinating reagent, DMF, room temperature, 66% c) LDA, Et$_3$SiCl, THF, room temperature, 79%; d) SELECTFLUOR fluorinating reagent, DMF, room temperature, 51%; e) NaBH$_4$, EtOH, room temperature, 78%; f) Br$_2$, CHCl$_3$, 0° C., 46%; g) c) t-BuOK, THF, room temperature, 49%.

Figure 20:
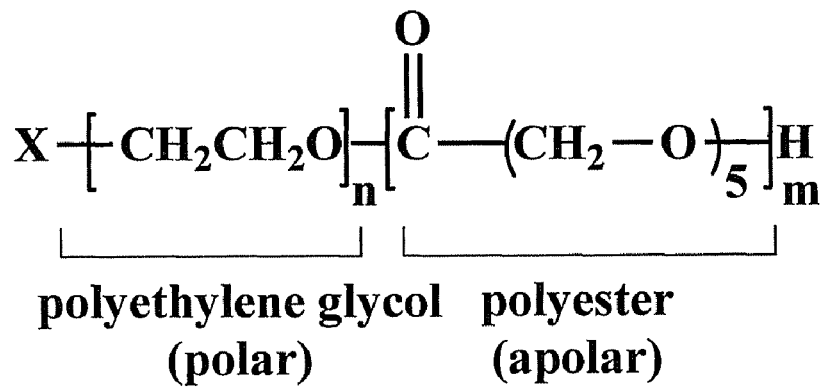
Figure 20:
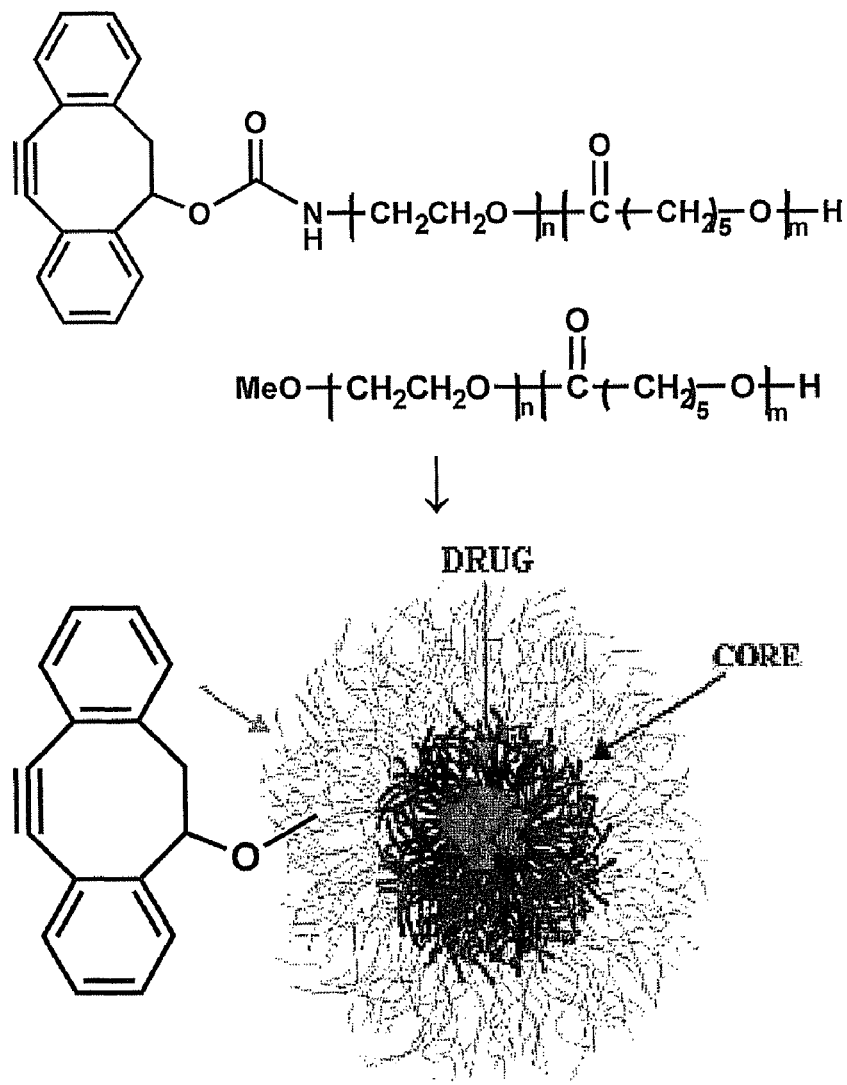
Figure 20:
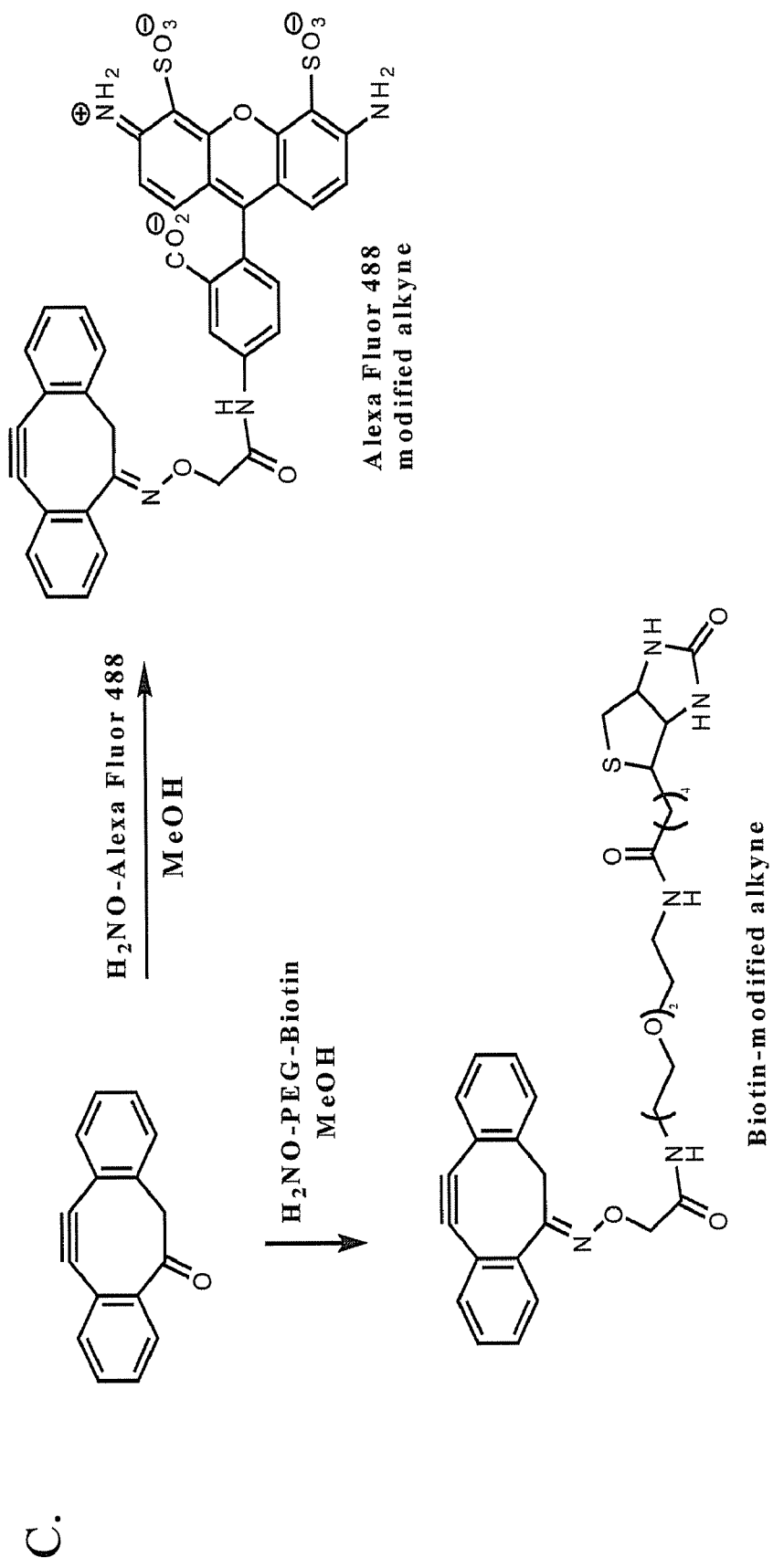

FIG. 20 illustrates the use of copolymer micelles for drug delivery. A) Polyester and polyethyleneglycol groups self-assembled in water. B) Functionalized copolymer micelles as drug delivery devices. C) Oxime-modified alkyne derivatives of copolymer micelles.

Figure 21:
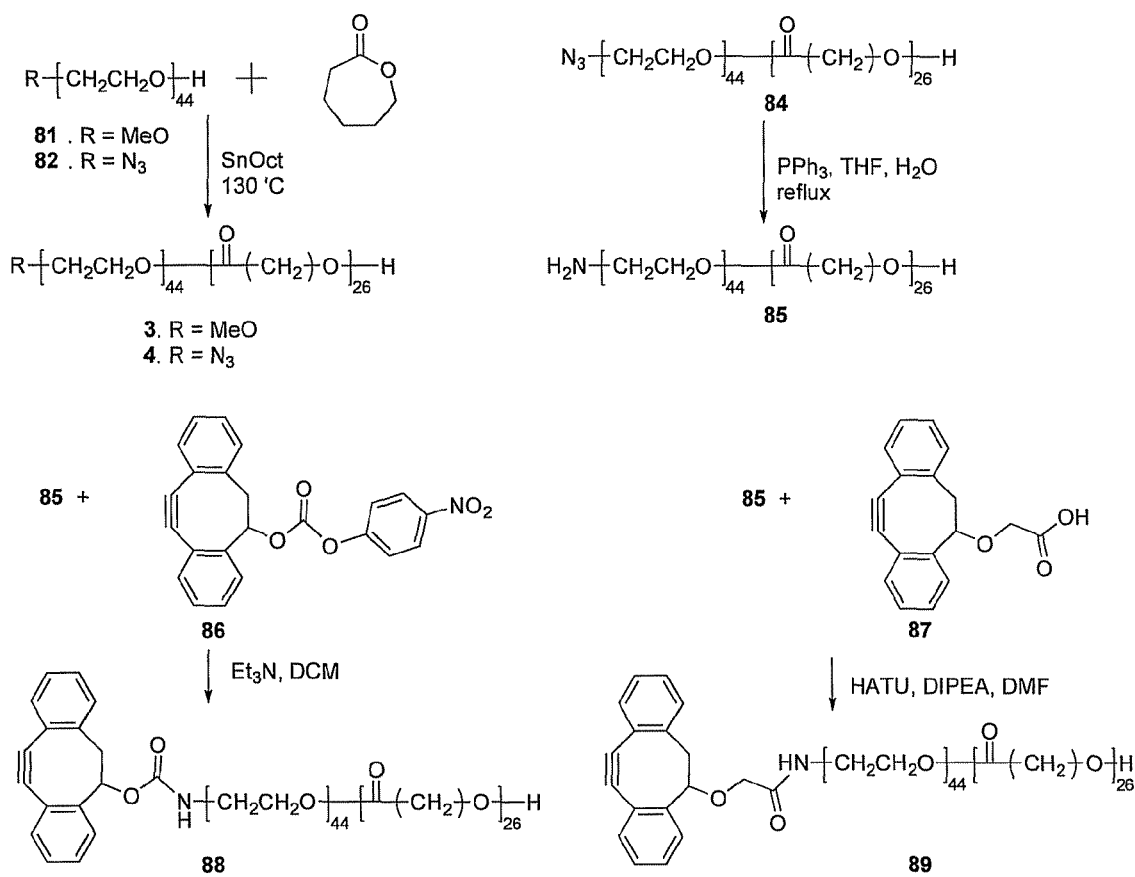

FIG. 21 illustrates the preparation of macromolecules with 4-dibenzocyclooctyne functionality.

Figure 22:
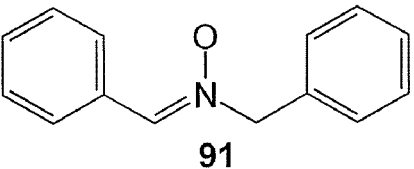
Figure 22:
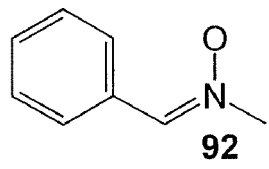
Figure 22:
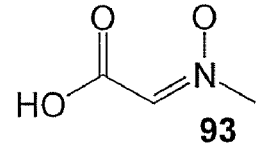
Figure 22:
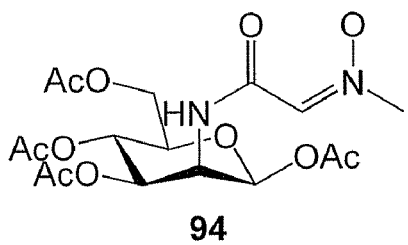
Figure 22:
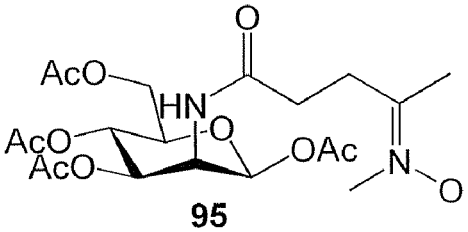

FIG. 22 illustrates cycloadditions of 4-dibenzocyclooctynol with various nitrones. Compounds were mixed at 1:1 molar ratio at a final concentration of 6 mM and reacted for a time indicated.

DETAILED DESCRIPTION OF ILLUSTRATIVE EMBODIMENTS

Alkynes such as those described herein can be reacted with at least one 1,3-dipole-functional compound in a cyclization reaction to form a heterocyclic compound. In preferred embodiments, the reaction can be carried out in the substantial absence of added catalyst (e.g., Cu(I)). Exemplary 1,3-dipole-functional compounds include, but are not limited to, azide-functional compounds, nitrile oxide-functional compounds, nitrone-functional compounds, azoxy-functional compounds, and/or acyl diazo-functional compounds.

Exemplary alkynes include alkynes of the formula:

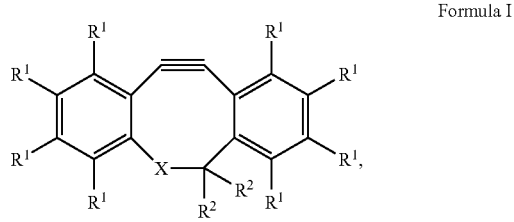

Formula I wherein: each $R^1$ is independently selected from the group consisting of hydrogen, halogen, hydroxy, alkoxy, nitrate, nitrite, sulfate, and a C1-C10 organic group (and preferably a C1-C10 organic moiety); each $R^2$ is independently selected from the group consisting of hydrogen, halogen, hydroxy, alkoxy, nitrate, nitrite, sulfate, and a C1-C10 organic group (and preferably a C1-C10 organic moiety); X represents C=O, C=N—OR$^3$, C=N—NR$^3$R$^4$, CHOR$^3$, or CHNHR$^3$; and each $R^3$ and $R^4$ independently represents hydrogen or an organic group (and in some embodiments an organic moiety). In preferred embodiments, each $R^1$ represents hydrogen and/or each $R^2$ represents hydrogen. Optionally, $R^3$ includes a covalently bound organic dye (e.g., a fluorescent dye).

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for compounds of this invention are those that do not interfere with the reaction of an alkyne with a 1,3-dipole-functional compound to form a heterocyclic compound. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, text-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the teens "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Alkynes of Formula I are typically strained, cyclic alkynes. Surprisingly it has been found that alkynes of Formula I as described herein (e.g., wherein X represents C=O, C=N—OR$^3$, C=N—NR$^3$R$^4$, CHOR$^3$, or CHNHR$^3$; and each R$^3$ and R$^4$ independently represents hydrogen or an organic group) have been found to have higher reactivity towards 1,3-dipole-functional compounds than other strained, cyclic alkynes (e.g., wherein X represents CH$_2$).

In certain embodiments of alkynes of Formula I, X can represent C=N—OR$^3$ wherein R$^3$ is an organic group. For example, $R^3$ can have the formula $-(CH_2)_aC(O)Y$, wherein: a is 1-3; Y represents OH or $NHR^5$; and $R^5$ represents hydrogen or a biotinylation product of a primary amine-containing organic group. The primary amine-containing group can, for example, be of the formula $-(CH_2CH_2O)_b(CH_2)_c$-$L_d$-$(CH_2CH_2O)_e(CH_2)_f NH_2$ and/or $-(CD_2CD_2O)_b(CD_2)_c$-$L_d$-$(CD_2CD_2O)_e(CD_2)_f NH_2$, wherein b=0 to 100 (e.g., 10 to 100); c=0 to 100 (and preferably 1 to 10); d=0 to 100 (and preferably 1 to 10); e=0 to 100 (e.g., 10 to 100); f=0 to 100 (and preferably 1 to 10); and L is an optional cleavable linker (e.g., a disulfide).

In certain embodiments of alkynes of Formula I, X can represent $CHOR^3$, wherein $R^3$ is selected from the group consisting of an alkyl group, an aryl group, an alkaryl group, and an aralkyl group. For example, $R^3$ can have the formula $-C(O)Z$, wherein: Z represents an alkyl group, $OR^6$, or $NHR^7$; and $R^6$ and $R^7$ are each independently selected from the group consisting of an alkyl group, an aryl group, an alkaryl group, and an aralkyl group. In certain embodiments, $R^7$ can be a biotinylation product of a primary amine-containing organic group. The primary amine-containing group can, for example, be of the formula $-(CF_2CH_2O)_b(CH_2)_c$-$L_d$-$(CF_2CH_2O)_e(CH_2)_f NH_2$ and/or $-(CD_2CD_2O)_b(CD_2)_c$-$L_d$-$(CD2CD_2O)_e(CD_2)_f NR_2$, wherein b=0 to 100 (e.g., 10 to 100); c=0 to 100 (and preferably 1 to 10); d=0 to 100 (and preferably 1 to 10); e=0 to 100 (e.g., 10 to 100); f=0 to 100 (and preferably 1 to 10); and L is an optional cleavable linker (e.g., a disulfide).

An exemplary alkyne of Formula I is the species in which X represents C=O, an alkyne of the formula:

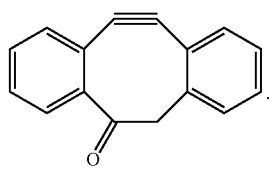

Formula IV

Another exemplary alkyne of Formula I is the species in which X represents CHOH, an alkyne of the formula:

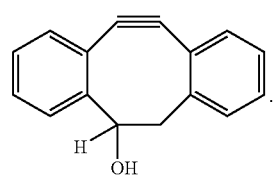

Formula V

Another exemplary alkyne of Formula I is the species in which X represents $CHNH_2$, an alkyne of the formula:

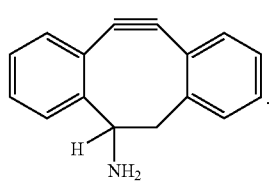

Formula VI

Another exemplary alkyne of Formula I is the species in which X represents $C=N-OR^3$, an alkyne of the formula:

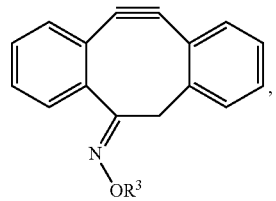

Formula VII wherein $R^3$ represents hydrogen or an organic group (and in some embodiments an organic moiety).

Additional exemplary alkynes include alkynes that have: a cleavable linker fragment including at least two ends; an alkyne fragment attached to a first end of the cleavable linker fragment; and a biotinylated fragment attached to a second end of the cleavable linker fragment. In certain embodiments, the alkyne fragment includes a strained, cyclic alkyne fragment. In certain embodiments, the alkyne further includes at least one heavy mass isotope. Optionally, the alkyne further includes at least one detectable label (e.g., a fluorescent label).

In certain embodiments of alkynes of Formula I, X can represent a polymeric or a copolymeric group. For embodiments in which X represents a copolymeric group, the copolymeric group can include a hydrophilic segment and a hydrophobic segment. For example, the copolymeric group can include a fragment of the formula $-[CH_2CH_2O]_n-[C(O)(CH_2)_5O]_m-H$, wherein n=0 to 100 (e.g., 10 to 100) and m=0 to 100 (e.g., 10 to 100). Surfaces on which drops of water or aqueous solutions exhibit a contact angle of less than 90 degrees are commonly referred to as "hydrophilic." The contact angle of a hydrophobic material with water is typically greater than 90 degrees.

Exemplary methods of making alkynes of Formula I are also disclosed herein. In one embodiment, the method includes: brominating an alkene of the formula:

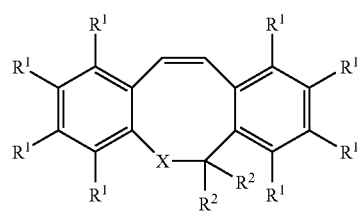

Formula XIV to provide a dibromide of the formula:

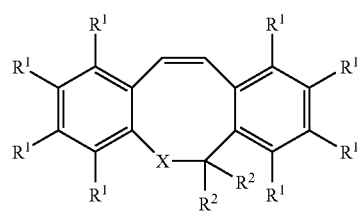

Formula XV and dehydrobrominating the dibromide of Formula XV to provide the alkyne of the formula:

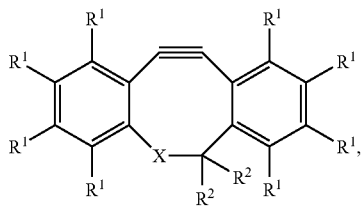

Formula I wherein: each $R^1$ is independently selected from the group consisting of hydrogen, halogen, hydroxy, alkoxy, nitrate, nitrite, sulfate, and a C1-C10 organic group; each $R^2$ is independently selected from the group consisting of hydrogen, halogen, hydroxy, alkoxy, nitrate, nitrite, sulfate, and a C1-C10 organic group; X represents C=O, C=N—OR$^3$, C=N—NR$^3$R$^4$, CHOR$^3$, or CHNHR$^3$; and each $R^3$ and $R^4$ independently represents hydrogen or an organic group (e.g., which can include a cleavable linker).

A wide variety of 1,3-dipole-functional compounds can be used to react with the alkynes disclosed herein. As used herein, a "1,3-dipole-functional compound" is meant to include compounds having at least one 1,3-dipole group attached thereto. As used herein, a "1,3-dipole group" is intended to refer to a group having a three-atom pi-electron system containing 4 electrons delocalized over the three atoms. Exemplary 1,3-dipole groups include, but are not limited to, azides, nitrile oxides, nitrones, azoxy groups, and acyl diazo groups. In certain embodiments, the 1,3-dipole-functional compound can be a biomolecule having at least one 1,3-dipole group attached thereto. Optionally, the at least one 1,3-dipole-functional compound can include a detectable label (e.g., an immunoassay or affinity label).

One or more 1,3-dipole-functional compounds (e.g., azide-functional compounds, nitrile oxide-functional compounds, nitrone-functional compounds, azoxy-functional compounds, and/or acyl diazo-functional compounds) can be combined with an alkyne as described herein under conditions effective to react in a cyclization reaction and form a heterocyclic compound. Preferably, conditions effective to form the heterocyclic compound can include the substantial absence of added catalyst. Conditions effective to form the heterocyclic compound can also include the presence or absence of a wide variety of solvents including, but not limited to, aqueous (e.g., water) and non-aqueous solvents; protic and aprotic solvents; polar and non-polar solvents; and combinations thereof. The heterocyclic compound can be formed over a wide temperature range, with a temperature range of 0° C. to 40° C. (and in some embodiments 23° C. to 37° C.) being particularly useful when biomolecules are involved. Conveniently, reaction times can be less than one day, and sometimes one hour or even less.

In certain embodiments, the cyclization reaction between the one or more 1,3-dipole-functional compounds and the alkyne can take place within or on the surface of a living cell. Such reactions can take place in vivo or ex vivo. As used herein, the term "in vivo" refers to a reaction that is within the body of a subject. As used herein, the term "ex vivo" refers to a reaction in tissue (e.g., cells) that has been removed, for example, isolated, from the body of a subject. Tissue that can be removed includes, for example, primary cells (e.g., cells that have recently been removed from a subject and are capable of limited growth or maintenance in tissue culture medium), cultured cells (e.g., cells that are capable of extended growth or maintenance in tissue culture medium), and combinations thereof.

An exemplary embodiment of a 1,3-dipole-functional compound is an azide-functional compound of the formula $R^8$—$N_3$ (e.g., represented by the valence structure $R^8$—$^-N$—$N{=}N^+$), wherein $R^8$ represents and organic group (e.g., a biomolecule). Optionally, $R^8$ can include a detectable label (e.g., an affinity label).

The cyclization reaction of an azide-functional compound of the formula $R^8$—$N_3$ with an exemplary alkyne of Formula I can result in one or more heterocyclic compounds of the formulas:

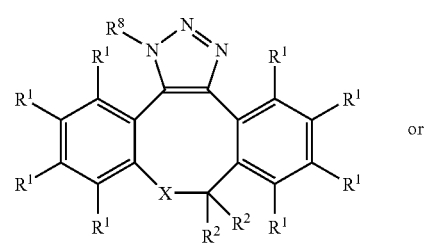

Formula II or

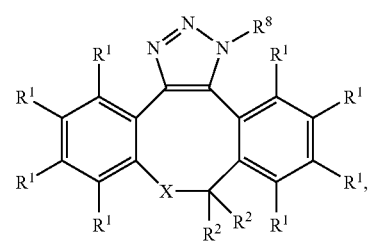

Formula III wherein: each $R^1$ is independently selected from the group consisting of hydrogen, halogen, hydroxy, alkoxy, nitrate, nitrite, sulfate, and a C1-C10 organic group; each $R^2$ is independently selected from the group consisting of hydrogen, halogen, hydroxy, alkoxy, nitrate, nitrite, sulfate, and a C1-C10 organic group; X represents C=O, C=N—OR$^3$, C=N—NR$^3$R$^4$, CHOR$^3$, or CHNHR$^3$; each $R^3$ and $R^4$ independently represents hydrogen or an organic group (e.g., which can include a cleavable linker); and $R^8$ represents an organic group (e.g., which can include a biomolecule and optionally a cleavable linker).

Another exemplary embodiment of a 1,3-dipole-functional compound is a nitrile oxide-functional compound of the formula $R^8$—CNO (e.g., represented by the valence structure $R^8$—$^+C{=}N$—$O^-$), wherein $R^8$ represents and organic group (e.g., a biomolecule). Optionally, $R^8$ can include a detectable label (e.g., an affinity label).

The cyclization reaction of a nitrile oxide-functional compound of the formula $R^8$—CNO with an exemplary alkyne of Formula I can result in one or more heterocyclic compounds of the formulas:

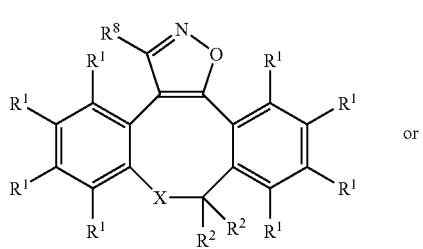

Formula VIII or

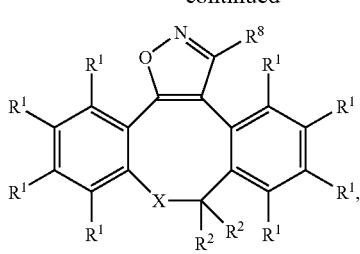

Formula IX wherein: each $R^1$ is independently selected from the group consisting of hydrogen, halogen, hydroxy, alkoxy, nitrate, nitrite, sulfate, and a C1-C10 organic group; each $R^2$ is independently selected from the group consisting of hydrogen, halogen, hydroxy, alkoxy, nitrate, nitrite, sulfate, and a C1-C10 organic group; X represents C=O, C=N—OR$^3$, C=N—NR$^3$R$^4$, CHOR$^3$, or CHNHR$^3$; each $R^3$ and $R^4$ independently represents hydrogen or an organic group (e.g., which can include a cleavable linker); and $R^8$ represents an organic group (e.g., which can include a biomolecule and optionally a cleavable linker).

Another exemplary embodiment of a 1,3-dipole-functional compound is a nitrone-functional compound of the formula $(R^{10})_2CN(R^{10})O$ (e.g., represented by the valence structure $(R^{10})_2C={}^+N(R^{10})\text{—}O^-$) wherein each $R^{10}$ independently represents hydrogen or an organic group, with the proviso that at least one $R^{10}$ represents an organic group (e.g., a biomolecule). Optionally, at least one $R^{10}$ can include a detectable label (e.g., an affinity label).

The cyclization reaction of a nitrone-functional compound of the formula $(R^{10})_2CN(R^{10})O$ with an exemplary alkyne of Formula I can result in one or more heterocyclic compounds of the formulas:

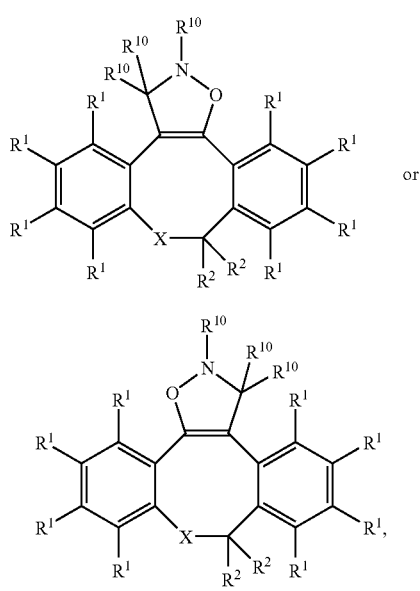

Formula X or

Formula XI wherein: each $R^1$ is independently selected from the group consisting of hydrogen, halogen, hydroxy, alkoxy, nitrate, nitrite, sulfate, and a C1-C10 organic group; each $R^2$ is independently selected from the group consisting of hydrogen, halogen, hydroxy, alkoxy, nitrate, nitrite, sulfate, and a C1-C10 organic group; X represents C=O, C=N—OR$^3$, C=N—NR$^3$R$^4$, CHOR$^3$, or CHNHR$^3$; and each $R^3$, $R^4$, and $R^{10}$ independently represents hydrogen or an organic group, with the proviso that at least one $R^{10}$ represents an organic group (e.g., which can include a biomolecule and optionally a cleavable linker).

Another exemplary embodiment of a 1,3-dipole-functional compound is an azoxy-functional compound of the formula $R^{10}\text{–}N={}^+N(R^{10})\text{—}O^-$) (e.g., represented by the valence structure $R^{10}\text{–}N={}^+N(R^{10})\text{–}O^-$, wherein each $R^{10}$ independently represents hydrogen or an organic group, with the proviso that at least one $R^{10}$ represents an organic group (e.g., a biomolecule). Optionally, at least one $R^{10}$ can include a detectable label (e.g., an affinity label).

The cyclization reaction of an azoxy-functional compound of the formula $R^{10}\text{—}NN(R^{10})O$ with an exemplary alkyne of Formula I can result in one or more heterocyclic compounds of the formulas:

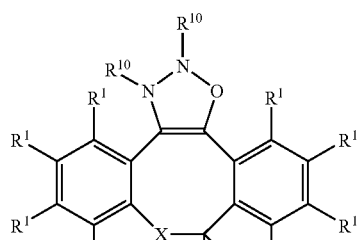

Formula XII or

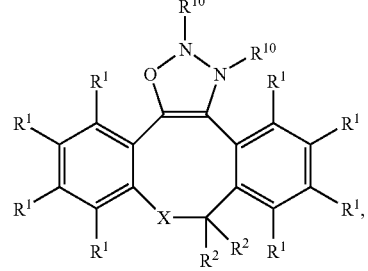

Formula XIII wherein: each $R^1$ is independently selected from the group consisting of hydrogen, halogen, hydroxy, alkoxy, nitrate, nitrite, sulfate, and a C1-C10 organic group; each $R^2$ is independently selected from the group consisting of hydrogen, halogen, hydroxy, alkoxy, nitrate, nitrite, sulfate, and a C1-C10 organic group; X represents C=O, C=N—OR$^3$, C=N—NR$^3$R$^4$, CHOR$^3$, or CHNHR$^3$; and each $R^3$, $R^4$, and $R^{10}$ independently represents hydrogen or an organic group, with the proviso that at least one $R^{10}$ represents an organic group (e.g., which can include a biomolecule and optionally a cleavable linker).

For embodiments in which the heterocyclic compound formed from the cyclization reaction between the alkyne and the one or more 1,3-dipole-functional compounds includes a detectable label, the heterocyclic compound can be detected using the detectable label. For example, for embodiments in which the detectable label is an affinity label, affinity binding (e.g., affinity chromatography) can be used to detect the heterocyclic compound.

In addition, for embodiments in which the heterocyclic compound formed from the cyclization reaction between the alkyne and the one or more 1,3-dipole-functional compounds includes a biotinylated fragment, the heterocyclic compound can be bound by contacting the heterocyclic compound with a compound that binds biotin (e.g., avidin and/or streptavidin). Further, the bound heterocyclic compound can be detected by methods described herein.

Cyclization reactions between alkynes as disclosed herein and 1,3-dipole-functional compounds can be used for a wide variety of applications. For example, an alkyne as disclosed herein can be attached to the surface of a substrate. In certain embodiments, the X group of the alkyne represents a point of attachment to the surface of the substrate. One of skill in the art will recognize that the X group can advantageously be selected to include functionality (e.g., biotin, activated esters, activated carbonates, and the like) to enable attachment of the alkyne to a functional substrate (e.g., amine functionality, thiol functionality, and the like) through a wide variety of reactions.

Substrates having an alkyne attached to the surface thereof can be reacted with 1,3-dipole-functional compounds to form heterocyclic compounds, effectively chemically bonding the 1,3-dipole-functional compounds to the substrate. Such substrates can be, for example, in the form of resins, gels, nanoparticles (e.g., including magnetic nanoparticles), or combinations thereof. In certain embodiments, such substrates can be in the form of microarrays or even three-dimensional matrices or scaffolds. Exemplary three-dimensional matrices include, but are not limited to, those available under the trade designations ALGIMATRIX 3D Culture system, GELTRIX matrix, and GIBCO three-dimensional scaffolds, all available from Invitrogen (Carlsbad, Calif.). Such three-dimensional matrices can be particularly useful for applications including cell cultures.

1,3-Dipole-functional biomolecules (e.g., 1,3-dipole-functional peptides, proteins, glycoproteins, nucleic acids, lipids, saccharides, oligosaccharides, and/or polysaccharides) can be immobilized on, and preferably covalently attached to, a substrate surface by contacting the 1,3-dipole-functional biomolecules with a substrate having an alkyne attached to the surface thereof under conditions effective for a cyclization reaction to form a heterocyclic compound. Preferably, conditions effective to form the heterocyclic compound can include the substantial absence of added catalyst. Conditions effective to form the heterocyclic compound can also include the presence or absence of a wide variety of solvents including, but not limited to, aqueous (e.g., water and other biological fluids) and non-aqueous solvents; protic and aprotic solvents; polar and non-polar solvents; and combinations thereof. The heterocyclic compound can be formed over a wide temperature range, with a temperature range of 0° C. to 40° C. (and in some embodiments 23° C. to 37° C.) being particularly useful. Conveniently, reaction times can be less than one day, and sometimes one hour or even less.

For example, when the substrate is in the form of a three-dimensional matrix and the 1,3-dipole-functional biomolecule is a 1,3-dipole-functional protein (e.g., an azide-functional protein), the cyclization reaction can result in an article having a protein immobilized on a three-dimensional matrix. Such matrices can have a wide variety of uses including, but not limited to, separating and/or immobilizing cell lines. Particularly useful proteins for these applications include, but are not limited to, collagen, fibronectin, gelatin, laminin, vitronectin, and/or other proteins commonly used for cell plating.

For another example, cyclization reactions between 1,3-dipole-functional compounds and alkynes of Formula I in which X represents a polymeric or a copolymeric group can be used, for example, for controlling the delivery of drugs as described herein below. For example, alkynes of Formula I in which X represents a copolymeric group including a hydrophilic segment and a hydrophobic segment can be blended with a polymer or a copolymer. Further, when an alkyne of Formula I in which X represents a copolymeric group including a hydrophilic segment and a hydrophobic segment is blended with a copolymer having a hydrophilic segment and a hydrophobic segment, a copolymer micelle can be formed. Particularly useful copolymers having a hydrophilic segment and a hydrophobic segment include those of the formula $R^9O—[CH_2CH_2O]_p—[C(O)(CH_2)_5O]_o—H$, wherein $R^9$ represents an alkyl group (e.g., methyl), p=0 to 100 (e.g., 1 to 100), and o=0 to 100 (e.g., 1 to 100).

The copolymer micelles that include an alkyne of Formula I as described herein above can advantageously be used to control the delivery of drugs. For example, a copolymer micelle that includes an alkyne of Formula I can be combined with at least one 1,3-dipole-functional drug and allowed to react under conditions effective to form a heterocyclic compound and attach the drug to the copolymer micelle. See, for example, Nishiyama et al., *Adv. Polym. Sci.* 2006, 193:67-101; Gaucher et al., *J. Control. Release* 2005, 109:169-188; Choi et al., *J. Dispersion Sci. Tech.* 2003, 24:475-487; Lavasanifar et al., *Adv. Drug Delivery Rev.* 2002, 54:169-190; and Rösier et al., *Adv. Drug Delivery Rev.* 2001, 53:95-108.

Further, because it does not require a toxic catalyst such as copper, the novel cycloaddition reaction provided by the invention can be used for labeling of living cells. For example, cells can first be metabolically labeled with an azide-functional precursor to produce azide-functional biomolecules (also referred to as bioconjugates) such as azide-functional glycoproteins (also referred to as glycoconjugates). The cells can then be contacted with an alkyne of Formula I, either in solution or on a substrate as discussed above, under conditions to permit labeling (via the cycloaddition reaction) of the azide-functional biomolecules at the surface of the cell. The resulting triazole conjugate can be detected at the cell surface, or it can be endocytosed by the cell and detected inside the cell.

Alkynes of Formula I can also have utility for imaging applications including, for example, as reagents for magnetic resonance imaging (MRI). For another example, alkynes of Formula I can contain a fluorescent tag. Alkynes of Formula I can also be useful in qualitative or quantitative proteomics and glycomics applications utilizing mass spectrometry. The alkyne of Formula I can be selected to contain one or more heavy mass isotopes, such as deuterium, $^{13}C$, $^{15}N$, $^{35}S$ and the like, and then can be used to label and/or immobilize azide-functional biomolecules as described herein.

Alkynes of Formula I can also have utility for applications such as vaccines. For example, alkynes of Formula I can be reacted with an azide-functional protein (e.g., an azide-functional carbohydrate, an azide-functional peptide, and/or an azide-functional glycopeptide), and the resulting triazole conjugate can be used as a carrier protein for the vaccine.

The present invention is illustrated by the following examples. It is to be understood that the particular examples, materials, amounts, and procedures are to be interpreted broadly in accordance with the scope and spirit of the invention as set forth herein.

EXAMPLES

Example 1

Visualizing Metabolically Labeled Glycoconjugates of Living Cells by Copper-Free and Fast Huisgen Cycloadditions Azides, which are extremely rare in biological systems, are emerging as attractive chemical handles for bioconjugation (Kolb and Sharpless, *Drug Discovery Today* 2003, 8:1128-1137; Dedola et al., *Org. Biomol. Chem.* 2007 5:1006-1017; Moses and Moorhouse, *Chem. Soc. Rev.* 2007, 36:1249-1262; Nandivada et al., *Adv. Mater.* 2007, 19:2197-2208; Wu and Fokin, *Aldrichimica Acta* 2007, 40:7-17). In particular, the $Cu^1$-catalyzed 1,3-dipolar cycloaddition of azides with terminal alkynes to give stable triazoles (Rostovtsev et al., *Angew. Chem.* 2002, 114:2708-2711; Rostovtsev et al., *Angew. Chem. Int. Ed.* 2002, 41:2596-2599; Tornoe et al., *J Org. Chem.* 2002, 67:3057-3064) has been employed for the tagging of a variety of biomolecules, (Chin et al., *Science* 2003, 301:964-967; Wang et al., *J. Am. Chem. Soc.* 2003, 125:3192-3193; Kho et al., *Proc. Natl. Acad. Sci. USA* 2004, 101:12479-12484; Gierlich et al., *Org. Lett.* 2006, 8:3639-3642; Link et al., *Proc. Natl. Acad. Sci. USA* 2006, 103:10180-10185) activity-based protein profiling (Speers et al., *J. Am. Chem. Soc.* 2003, 125:4686-4687), and the chemical synthesis of microarrays and small-molecule libraries (Sun et al., *Bioconjugate Chem.* 2006, 17:52-57).

An attractive approach for installing azides into biomolecules is based on metabolic labeling, whereby an azide-containing biosynthetic precursor is incorporated into biomolecules by using the cells' biosynthetic machinery (Prescher and Bertozzi, *Nat. Chem. Biol.* 2005, 1:13-21). This approach has been employed for tagging proteins, glycans, and lipids of living systems with a variety of reactive probes. These probes can facilitate the mapping of saccharide-selective glycoproteins and identify glycosylation sites (Hanson et al., *J. Am. Chem. Soc.* 2007, 129:7266-7267). Alkyne probes have also been used for cell-surface imaging of azide-modified biomolecules, and a particularly attractive approach involves the generation of a fluorescent probe from a nonfluorescent precursor by a [3+2] cycloaddition (Sivakumar et al., *Org. Lett.* 2004, 6:4603-4606).

Figure 1:
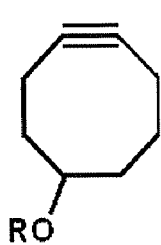
FIG. 1 illustrates exemplary reagents for labeling azide-functional biomolecules.
Figure 1:
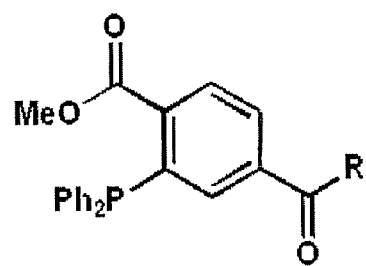
Figure 1:
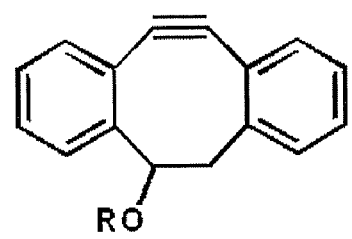

The cellular toxicity of the $Cu^1$ catalyst has precluded applications wherein cells must remain viable (Link and Tinel, *J. Am. Chem. Soc.* 2003, 125:11164-11165), and hence there is a great need for the development of $Cu^1$-free [3+2] cycloadditions (Turner et al., *J. Am. Chem. Soc.* 1973, 95:790-792; Agard et al., *J. Am. Chem. Soc.* 2004, 126:15046-15047; vanBerkel et al., *Chem-BioChem* 2007, 8:1504-1508). In this respect, alkynes can be activated by ring strain, and, for example, constraining an alkyne within an eight-membered ring creates 18 kcalmol$^{-1}$ of strain, much of which is released in the transition state upon [3+2] cycloaddition with an azide (Turner et al., *J. Am. Chem. Soc.* 1973, 95:790-792; Agard et al., *J. Am. Chem. Soc.* 2004, 126:15046-15047). As a result, cyclooctynes such as 1 react with azides at room temperature without the need for a catalyst (FIG. 1). The strain-promoted cycloaddition has been used to label biomolecules without observable cytotoxicity (Agard et al., *J. Am. Chem. Soc.* 2004, 126:15046-15047). The scope of the approach has, however, been limited because of the slow rate of reaction (Agard et al., *ACS Chem. Biol.* 2006, 1:644-648). Appending electron-withdrawing groups to the octyne ring can increase the rate of strain-promoted cycloadditions; however, currently Staudinger ligation with phosphine 2 offers the most attractive reagent for cell-surface labeling with azides.

It was envisaged that 4-dibenzocyclooctynols such as compound 3 would be ideal for labeling living cells with azides because the aromatic rings are expected to impose additional ring strain and conjugate with the alkyne, thereby increasing the reactivity of the alkyne in metal-free [2+3] cycloadditions with azides. The compound should, however, have excellent stability because the ortho hydrogen atoms of the aromatic rings shield the alkyne from nucleophilic attack. Furthermore, the hydroxy group of 3 provides a handle for the incorporation of tags such as fluorescent probes and biotin.

Figure 2:
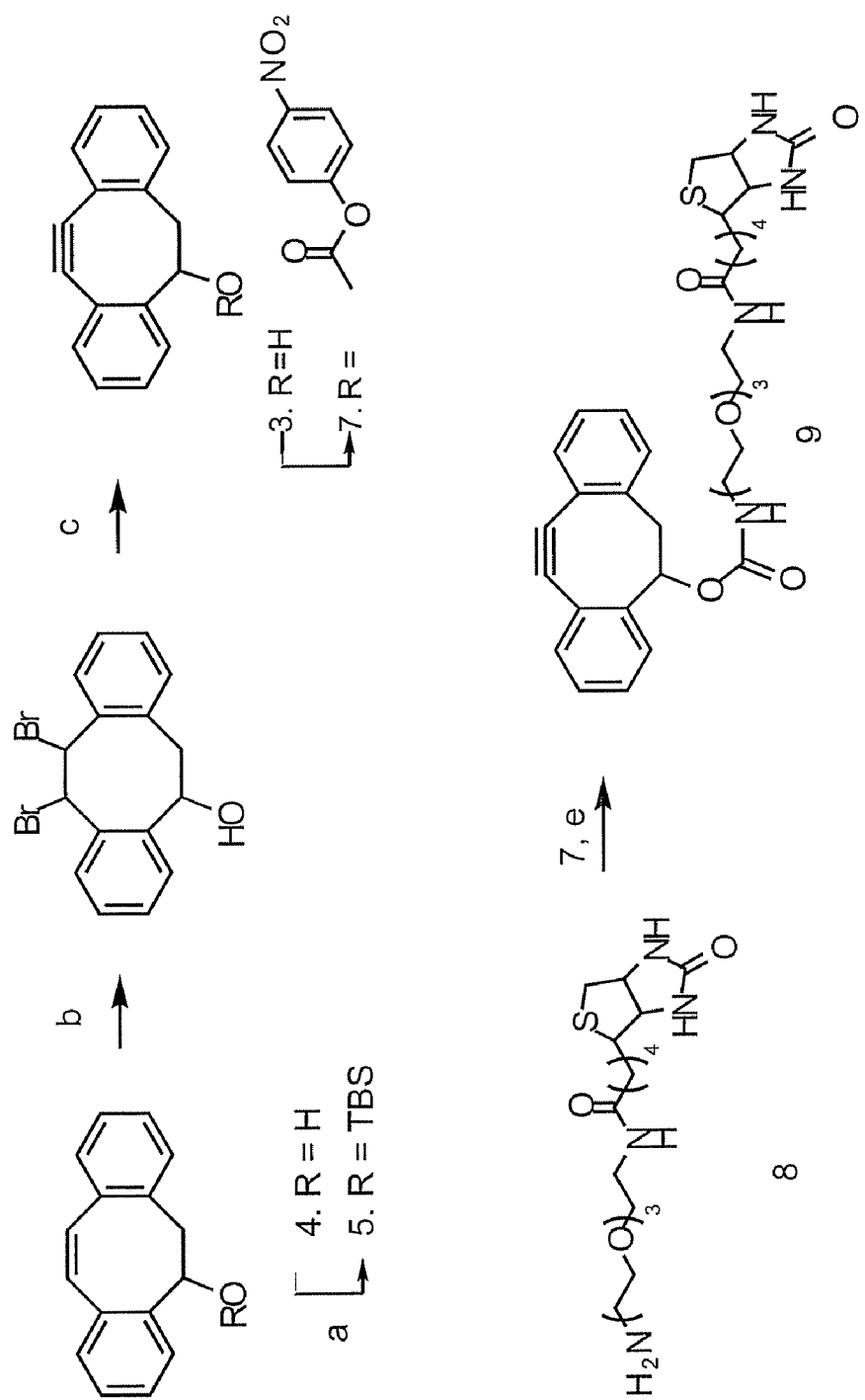
FIG. 2 illustrates Scheme 1: exemplary reagents and conditions: a) TBSCl, pyridine; b) Br$_2$, CHCl$_3$; c) LDA, tetrahydrofuran; d) 4-nitrophenyl chloroformate, pyridine, C$_2$Cl$_2$; e) N,N-dimethylformamide (DMF), triethylamine (TEA). LDA=lithium diisopropylamide, TBS=tert-butyldimethylsilyl.

Compound 3 could be prepared easily from known (Jung et al., *J. Org. Chem.* 1978, 43:3698-3701; Jung and Miller, *J. Am. Chem. Soc.* 1981, 103:1984-1992) 3-hydroxy-1,2:5,6-dibenzocycloocta-1,5,7-triene (4) by protection of the hydroxy group as a TBS ether to give 5, which was brominated to provide dibromide 6 in a yield of 60% (Scheme 1; FIG. 2). The TBS protecting group was lost during the latter transformation, but the bromination was low yielding when performed on alcohol 4. Dehydrobromination of 6 by treatment with LDA in THF at 0° C. (Seitz et al., *Angew. Chem.* 1969, 81:427-428; Seitz et al., *Angew. Chem. Int. Ed. Engl.* 1969, 8:447-448) gave the target cyclooctyne 3 in a yield of 45%.

Figure 3:
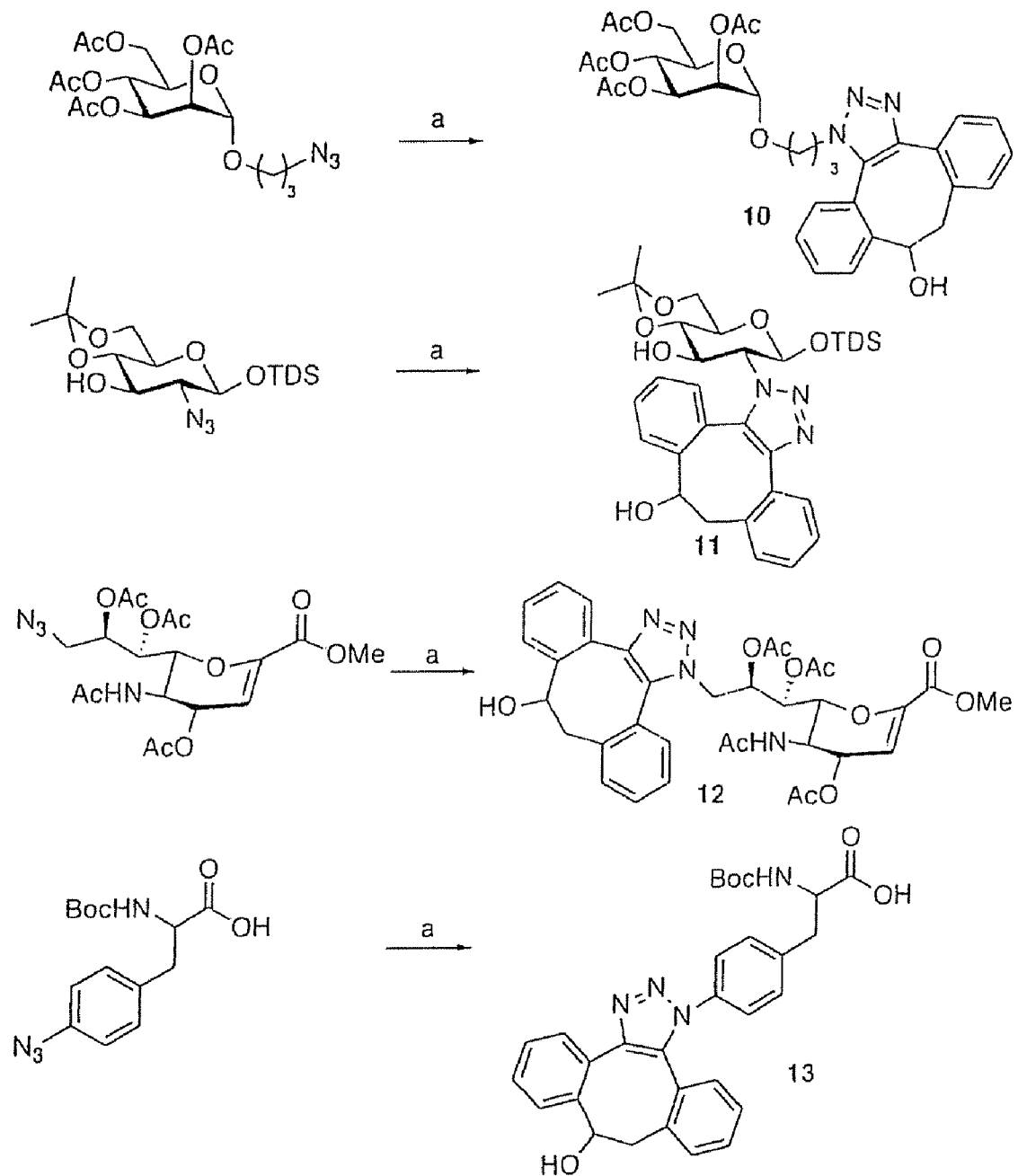
FIG. 3 illustrates Scheme 2: exemplary reagents and conditions: a) compound 3 in methanol.
Figure 4:
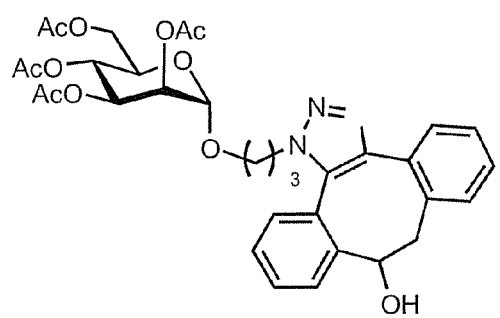
FIG. 4 illustrates exemplary metal-free cycloadditions of compound 3 with azide-functional amino acid and saccharides. Boc=tert-butoxycarbonyl, TDS=thexyldimethylsilyl.
Figure 4:
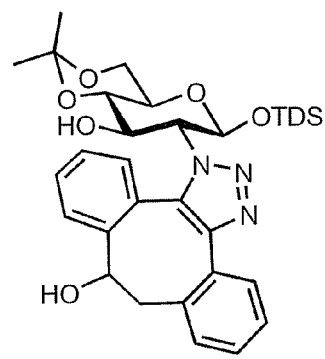
Figure 4:
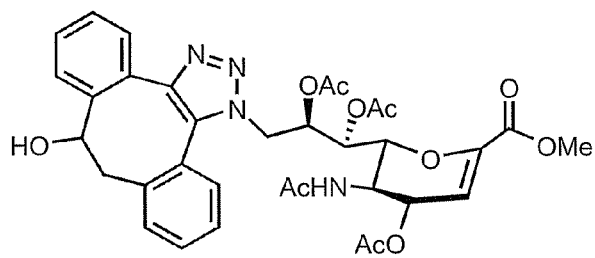
Figure 4:
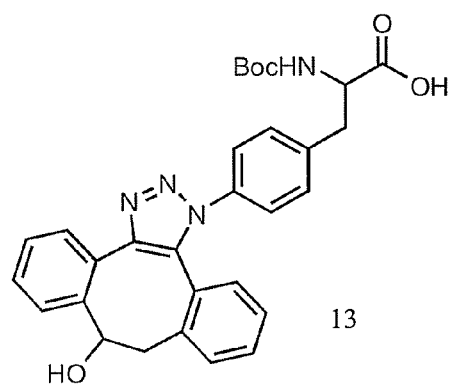

Compound 3 has an excellent, long shelf life and after treatment did not react with nucleophiles such as thiols and amines. However, upon exposure to azides a fast reaction took place and gave the corresponding triazoles in high yield. For example, triazoles 10-13 were obtained in quantitative yields as mixtures of regioisomers by reaction of the corresponding azido-containing sugar and amino acid derivatives with 3 in methanol for 30 minutes (Scheme 2; FIG. 3 and FIG. 4). The progress of the reaction of 3 with benzyl azide in methanol and in a mixture of water/acetonitrile (1:4 v/v) was monitored by $^1$H NMR spectroscopy by integration of the benzylic proton signals, and second-order rate constants of 0.17 and 2.3 $m^{-1}$ $s^{-1}$ respectively, were determined. The rate constant of the reaction with 3 in acetonitrile/water is approximately three orders of magnitude greater than that with cyclooctyne 1.

Figure 5:
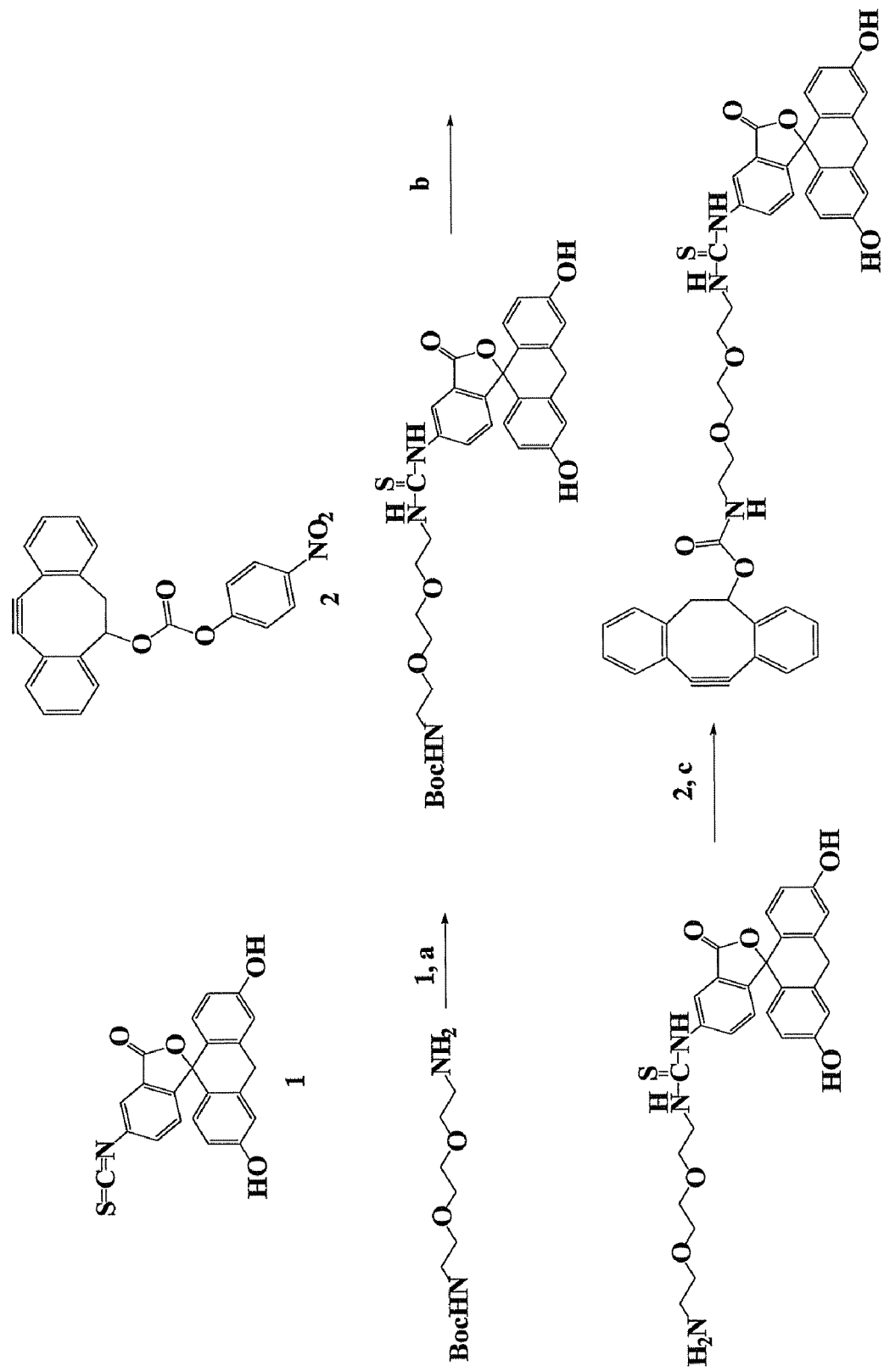
FIG. 5 illustrates Scheme 3: exemplary reaction conditions: a) 1, triethylamine, DMF, room temperature, 78%; b) 20% trifluoroacetic acid (TFA), room temperature, 95%; c)$_2$, TEA, DMF, room temperature, 68%.

Having established the superior reactivity of 3, we focused our attention on the preparation of a derivative of 4-dibenzocyclooctynol (9; Scheme 1; FIG. 2), which is modified with biotin. Such a reagent should make it possible to visualize biomolecules after metabolically labeling cells with an azido-containing biosynthetic precursor, followed by cycloaddition with 9 and treatment with avidin modified with a fluorescence probe. Alternatively, biotinylation of glycoconjugates with 9 should make it possible to isolate these derivatives for glycocomics studies using avidin immobilized on a solid support. Compound 9 could easily be prepared by a two-step reaction involving treatment of 3 with 4-nitrophenyl chloroformate to give activated intermediate 7, followed by immediate reaction with 8. 4-dibenzocyclooctynol (9) may also be functionalized with a fluorescent tag to yield a fluorescent derivative (Scheme 3; FIG. 5).

Next, Jurkat cells were cultured in the presence of 25 micromolar N-azidoacetylmannosamine ($Ac_4$ManNAz) for three days to metabolically introduce N-azidoacetylsialic acid (SiaNAz) moieties into glycoproteins (Luchansky and Bertozzi, *Chem-BioChem* 2004, 5:1706-1709). As a negative control, Jurkat cells were employed that were grown in the absence of $Ac_4$ManNAz. The cells were exposed to a 30 micromolar solution of compound 9 for various time periods, and after washing, the cells were stained with avidin-fluorescein isothiocyanate (FITC) for 15 minutes at 4° C. The efficiency of the two-step cell-surface labeling was determined by measuring the fluorescence intensity of the cell lysates. For comparison, the cell-surface azido moieties were also labeled by Staudinger ligation with biotin-modified phosphine 2 followed by treatment with avidin-FITC. The labeling with 9 was almost complete after an incubation time of 60 minutes (FIG. 6a).

Figure 7:
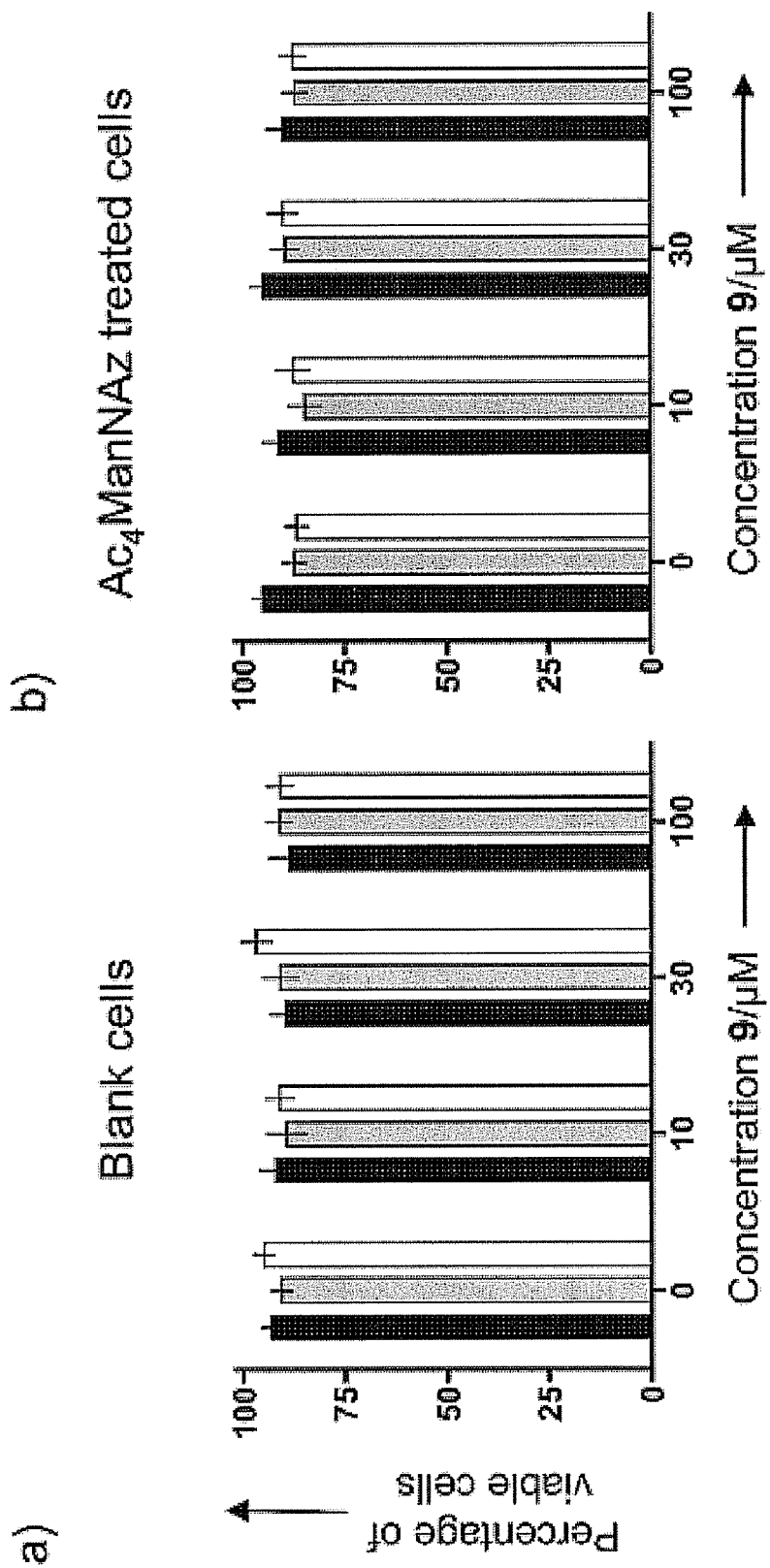
FIG. 7 illustrates an embodiment of toxicity assessment of cell labeling procedure and cycloaddition reaction with compound 9. Jurkat cells grown for 3 days in the absence (a) or presence (b) of Ac$_4$ManNAz (25 micromolar) were incubated with compound 9 (0-100 micromolar) for 1 hour at room temperature. The cells were washed three times and then incubated with avidin conjugated with fluorescein for 15 minutes at 4° C., after which cells were washed three times. Cell viability was assessed at different points during the procedure with trypan blue exclusion; after incubation with 9 (black), after avidin-FITC incubation (grey), and after complete procedure (white). Treatment with Cu$^1$Cl (1 mM) under the same conditions led to approximately 98% cell death for both the blank and the Ac$_4$ManNAz treated cells.

Interestingly, under identical conditions phosphine 2 (Agard et al., *ACS Chem. Biol.* 2006, 1:644-648) gave significantly lower fluorescent intensities, indicating that cell surface labeling by Staudinger ligation is slower and less efficient. In each case, the control cells exhibited very low fluorescence intensities, demonstrating that background labeling is negligible. It was found that the two-step labeling approach with 9 had no effect on cell viability, as determined by morphology and exclusion of trypan blue (data not shown; FIG. 7).

Figure 6:
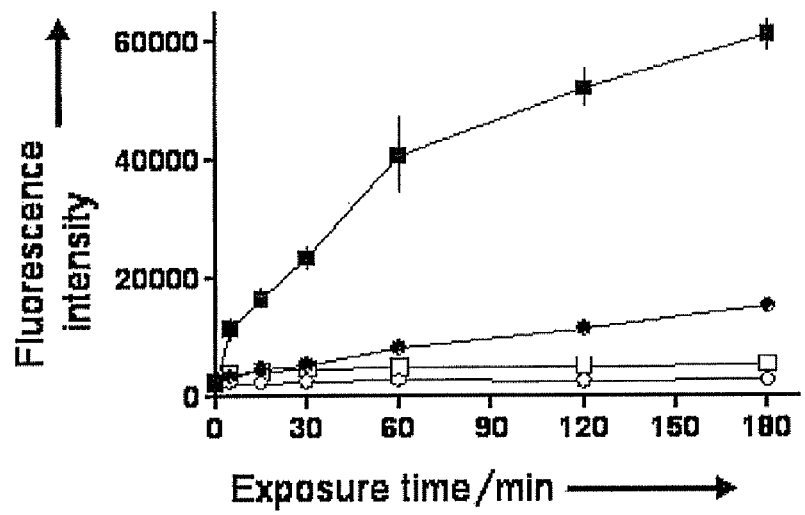
FIG. 6 illustrates embodiments of cell-surface labeling with compounds 2 and 9. Jurkat cells grown for three days in the absence or presence of Ac$_4$ManNAz (25 micromolar) were incubated a) with compounds 2 and 9 (30 micromolar) for 0-180 minutes or b) with compounds 2 and 9 (0-100 micromolar) for 1 hour at room temperature. Next, the cells were incubated with avidin-FITC for 15 minutes at 4° C., after which cell lysates were assessed for fluorescence intensity. Samples are indicated as follows: blank cells incubated with 2 (○) or 9 (□), and Ac,ManNAz cells incubated with 2 (●) or 9 (■).
Figure 6:
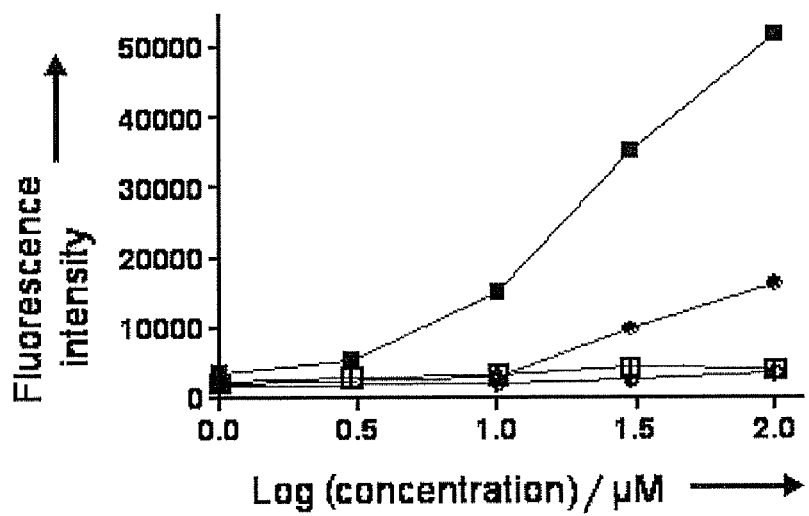

The concentration dependence of the cell-surface labeling was studied by incubation of cells with various concentrations of 2 and 9 followed by staining with avidin-FTIC (FIG. 6b). As expected, cells displaying azido moieties showed a dose-dependent increase in fluorescence intensity. Reliable fluorescent labeling was achieved at a 3 micromolar concentration of 9; however, optimal results were obtained at concentrations ranging from 30 to 100 micromolar. No increase in labeling was observed at concentrations higher than 100 micromolar owing to the limited solubility of 9.

Figure 8:
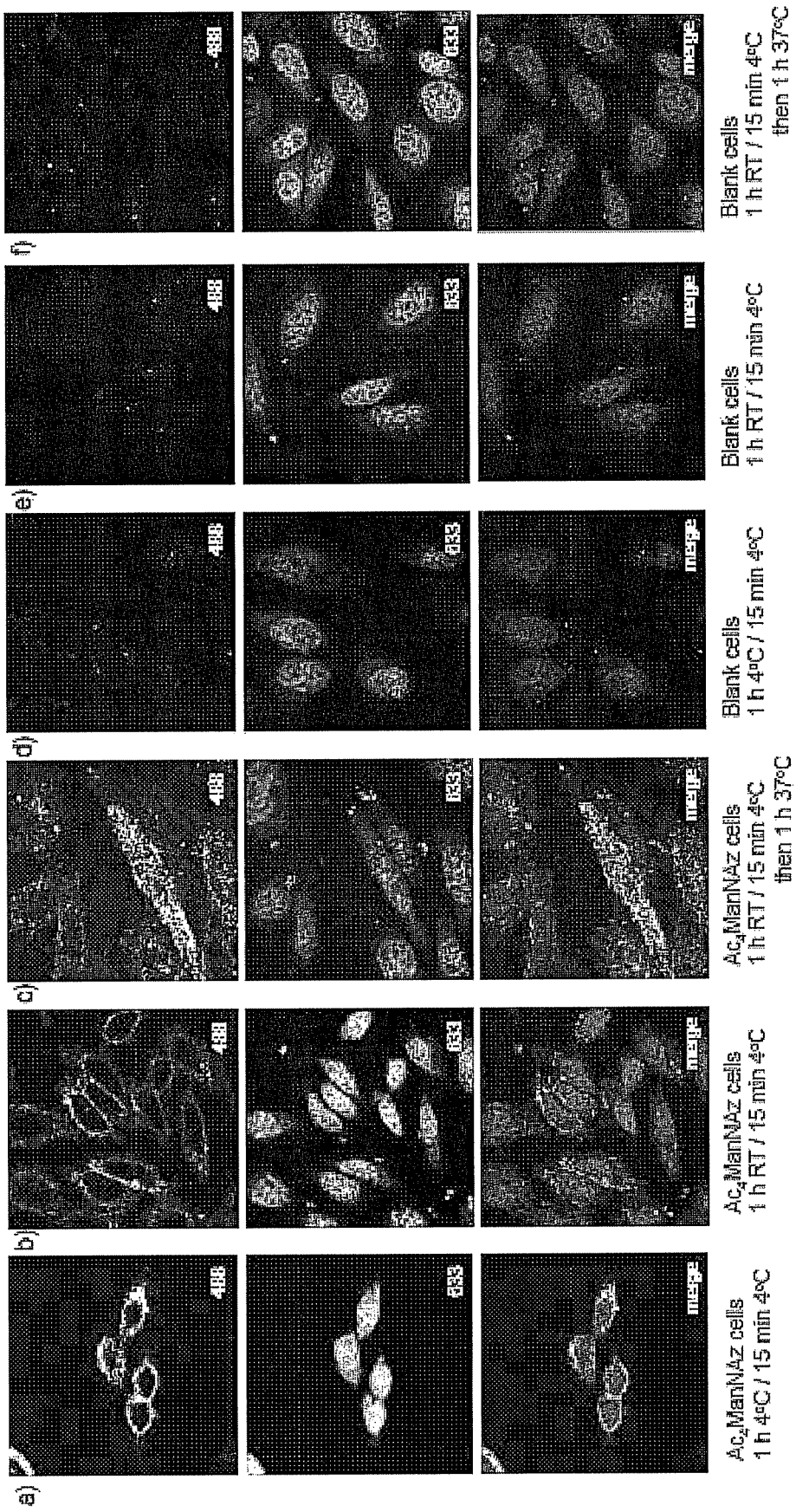
FIG. 8 illustrates fluorescence images for embodiments of cells labeled with compound 9 and avidin-Alexa Fluor 488. CHO cells grown for 3 days in the absence (d-f) or presence (a-c) of Ac$_4$ManNAz (100 micromolar) were incubated with compound 9 (30 micromolar) for 1 hour at 4° C. (a, d) or room temperature (b, c, e, f). Next, cells were incubated with avidin-Alexa Fluor 488 for 15 minutes at 4° C. and, after washing, fixing, and staining for the nucleus with far-red-fluorescent dye TO-PRO, imaged (a, b, d, e) or after washing incubated for 1 hour at 37° C. before fixing, nucleus staining, and imaging (c,f). Merged indicates that the images of cells labeled with Alexa Fluor (488 nanometers (nm)) and TO-PRO-3 iodide (633 nm) are merged.

Next, attention was focused on visualizing azido-containing glycoconjugates of living cells by confocal microscopy. Thus, adherent Chinese hamster ovary (CHO) cells were cultured in the presence of Ac$_4$ManNAz (100 micromolar) for three days. The resulting cell-surface azido moieties were treated with 9 (30 micromolar) for 1 hour and then with avidin-AlexaFluor488 for 15 minutes at 4° C. As expected, staining was observed only at the surface (FIG. 8), and the labeling procedure was equally efficient when performed at either ambient temperature or 4° C. Furthermore, blank cells exhibited very low fluorescence staining, confirming that background labeling is negligible.

Cell-surface glycoconjugates are constantly recycled by endocytosis, and to monitor this process, metabolically labeled cells were reacted with 9 and avidin-AlexaFluor488 according to the standard protocol and incubated at 37° C. for 1 hour before examination by confocal microscopy. We observed that a significant quantity of labeled glycoproteins had been internalized into vesicular compartments.

At the completion of these studies, Bertozzi and co-workers reported a difluorinated cyclooctyne (DIFO) that reacts with azides at almost the same reaction rate as compound 3 (Baskin et al., *Proc. Natl. Acad. Sci. USA* 2007, 104:16793-16797). DIFO linked to AlexaFluor was employed to investigate the dynamics of glycan trafficking. It was found that after incubation for 1 hour, labeled glycans colocalized with markers for endosomes and Golgi.

4-Dibenzocyclooctynols such as 3 and 9 have several advantageous features for researchers such as ease of chemical synthesis and the possibility to further enhance the rate of cycloaddition by functionalization of the aromatic moieties. Modifying the aromatic rings may also offer an exciting opportunity to obtain reagents that become fluorescent upon [3+2] cycloaddition with azido-containing compounds, which will make it possible to monitor in real time the trafficking of glycoproteins and other biomolecules in living cells.

General Methods and Materials

Chemicals were purchased from Aldrich and Fluka and used without further purification. Dichloromethane was distilled from CaH$_2$ and stored over molecular sieves 4 Å. Pyridine was distilled from P$_2$O$_5$ and stored over molecular sieves 4 Å. THF was distilled form sodium. All reactions were performed under anhydrous conditions under an atmosphere of Argon. Reactions were monitored by thin layer chromatography (TLC) on Kieselgel 60 F254 (Merck). Detection was by examination under ultraviolet (UV) light (254 nm) or by charring with 5% sulfuric acid in methanol. Flash chromatography was performed on silica gel (Merck, 70-230 mesh). Iatrobeads (60 micrometers) were purchased from Bioscan. $^1$H NMR (1D, 2D) and $^{13}$C NMR were recorded on a Varian Merc 300 spectrometer and on Varian 500 and 600 MHz spectrometers equipped with Sun workstations. $^1$H and $^{13}$C NMR spectra were recorded in CDCl$_3$, and chemical shifts (δ) are given in ppm relative to solvent peaks ($^1$H, δ 7.24; $^{13}$C, δ 77.0) as internal standard for protected compounds. Negative ion matrix assisted laser desorption ionization time of flight (MALDI-TOF) were recorded on a VOYAGER-DE Applied Biosystems using dihydrobenzoic acid as a matrix. High-resolution mass spectra were obtained using a VOYAGER-DE Applied Biosystems in the positive mode by using 2,5-dihydroxyl-benzoic acid in THF as matrix.

3-tert-Butyl-dimethylsilyl-oxy-1,2:5,6-dibenzocycloocta-1,5,7-triene (5)

text-Butyl dimethyl silyl chloride (3.0 g, 20 mmol) was added to a stirred solution of 4 (2.2 g, 10 mmol) in a mixture of CR$_2$Cl$_2$ (20 mL) and pyridine (5 mL). After stirring for 6 hours at room temperature, the reaction mixture was diluted with water and extracted with CH$_2$Cl$_2$ (40 mL). The combined organic extracts were washed with water and brine and then dried (MgSO$_4$). The solvents were evaporated under reduced pressure and the residue was purified by silica gel column chromatography (hexane/ethyl acetate, 7/1, v/v) to afford 5 (2.9 g, 87%). $^1$H NMR (300 MHz, CDCl$_3$): δ 7.60 (1H, aromatics), 7.32-7.11 (7H, aromatics), 6.93 (1H, d, J=7.5 Hz, CH=CH), 6.85 (1H, d, J=7.5 Hz, CH=CH), 5.51 (1H, dd, J=6.3, 9.6 Hz, CHOSi), 3.54 (1H, dd, J=6.3, 9.6 Hz, CH$_2$), 3.21 (1H, dd, J=6.3, 9.6 Hz, CH), 0.96 (3H, s, CH$_3$), 0.95 (3H, s, CH$_3$), 0.94 (3H, s, CH$_3$), 0.10 (3H, s, CH$_3$), 0.07 (3H, s, CH$_3$); $^{13}$C NMR (75 MHz, CDCl$_3$): δ 148.0, 141.6, 140.8, 139.2, 138.3, 135.5, 135.0, 134.9, 133.0, 131.9, 131.6, 130.9, 130.8, 130.2, 77.0, 52.1, 34.5, 30.7, 30.5, 23.1, 5.8, 0.1; MALDI HRMS: m/z 359.1811 [M+Na+]. Calcd for C$_{22}$H$_{28}$NaOSi 359.1807.

3-Hydroxy-7,8-dibromo-1,2:5,6-dibenzocyclooctene (6)

A solution of bromine (0.8 g, 5 mmol) in CHCl$_3$ was added dropwise to a solution of 5 (1.7 g, 5 mmol) in CHCl$_3$ (30 mL) at 0° C. The reaction mixture was stirred at room temperature for 12 hours until the reaction was complete (monitored by TLC). The resulting mixture was washed with aqueous saturated sodium thiosulfate solution (15 mL), and dried (MgSO$_4$). The solvents were evaporated under reduced pressure and the residue was purified by silica gel column chromatography (hexane/CH$_2$Cl$_2$, 7/1, v/v) to afford 6 (1.2 g, 60%). $^1$H NMR (300 MHz, CDCl$_3$): δ 7.54-7.47 (2H, aromatics), 7.31-6.72 (6H, aromatics), 5.77 (1H, d, J=5.4 Hz, CHBr), 5.22 (1H, dd, J=3.6, 15.9 Hz, CHOH), 5.19 (1H, d, J=5.4 Hz, CHBr), 3.50 (1H, dd, J=3.6, 15.9 Hz, CH$_2$), 2.75 (1H, dd, J=3.6, 15.9 Hz, CH$_2$); $^{13}$C NMR (75 MHz, CDCl$_3$): δ 141.3, 140.0, 137.2, 134.0, 133.4, 131.5, 131.3, 130.9, 127.8, 126.2, 123.7, 121.3, 76.5, 70.0, 62.3, 32.2; MALDI HRMS: m/z 402.9313 [M+Na+]. Calcd for C$_{16}$H$_{14}$Br$_2$NaO 402.9309.

3-Hydroxy-7,8-didehydro-1,2:5,6-dibenzocyclooctene (3)

To a solution of 6 (1.1 g, 3 mmol) in tetrahydrofuran (50 mL) was added dropwise lithium diisopropylamide in tetrahydrofuran (2.0 M), (5 mL) under an atmosphere of Argon at room temperature. The reaction mixture was stirred for 2 hours at room temperature, after which it was poured into ice water (50 mL) and the resulting mixture was extracted with $CH_2Cl_2$ (2×100 mL). The combined extracts were washed with water and brine and then dried ($MgSO_4$). The solvents were evaporated under reduced pressure and the residue purified by silica gel column chromatography (hexane/ethyl acetate, 5/1, v/v) to afford 3 (0.30 g, 45%). $^1H$ NMR (300 MHz, $CDCl_3$): δ 7.67 (1H, aromatics), 7.37-7.18 (7H, aromatics), 4.57 (1H, dd, J=2.1, 14.7 Hz, CHOH), 3.04 (1H, dd, J=2.1, 14.7 Hz, $CH_2$), 2.86 (1H, dd, J=2.1, 14.7 Hz, $CH_2$); $^{13}C$ NMR (75 MHz, $CDCl_3$): δ154.5, 150.6, 128.6, 127.1, 1127.0, 126.0, 125.8, 125.1, 124.7, 123.0, 122.7, 121.7, 111.9, 109.6, 74.2, 47.7.

Carbonic acid 7,8-didehydro-1,2:5,6-dibenzocyclooctene-3-yl ester 4-nitrophenyl ester (7)

To a solution of 3 (0.22 g, 1 mmol) in $CH_2Cl_2$ (30 mL) was added 4-nitro-phenyl chloroformate (0.4 g, 2 mmol) and pyridine (0.4 ml, 5 mmol). After stirring 4 hours at ambient temperature, the reacting mixture was washed with brine (2×10 mL), and the organic layer was dried ($MgSO_4$). The solvents were evaporated under reduced pressure, and the residue was purified by silica gel column chromatography (hexane/ethyl acetate, 10/1, v/v) to afford 7 (0.34 g, 89%). $^1H$ NMR (300 MHz, $CDCl_3$): δ 8.23-8.18 (2H, aromatics), 7.56-7.54 (2H, aromatics), 7.46-7.18 (8H, aromatics), 5.52 (1H, dd, J=3.9, 15.3 Hz, CHOH), 3.26 (1H, dd, J=3.9, 15.3 Hz, $CH_2$), 2.97 (1H, dd, J=3.9, 15.3 Hz, $CH_2$); $^{13}C$ NMR (75 MHz, $CDCl_3$): δ 154.5, 150.7, 149.1, 148.7, 129.0, 127.4, 127.3, 126.7, 126.5, 125.5, 125.2, 124.3, 124.0, 122.6, 122.4, 120.8, 120.6, 120.2, 112.2, 108.5, 80.6, 44.8; MALDI HRMS: m/z 408.0852 [M+Na+]. Calcd for $C_{23}H_{15}NNaO_5$ 408.0848.

Carbonic acid 7,8-didehydro-1,2:5,6-dibenzocyclooctene-3-yl ester, 8'-biotinylamine-3',6'-dioxaoctane 1'-amide (9)

To a solution of 8 (37 mg, 0.1 mmol) and NEt3 (30 mg, 0.3 mmol) in DMF (10 mL) was added 7 (39 mg, 0.1 mmol) under an atmosphere of Argon. After stirring the reaction mixture overnight at ambient temperature, the solvent was removed under reduced pressure and the residue was purified by silica gel column chromatography ($CH_2Cl_2/CH_3OH$, 20/1, v/v) to afford 9 (44 mg, 71%). $^1H$ NMR (500 MHz, CD3OD): δ 7.59 (1H, aromatics), 7.42-7.33 (7H, aromatics), 5.44, (1H, dd, J=5.0, 14.1 Hz, CHOH), 4.60, 4.46 (m, 2H, CHNH), 4.24 (s, 4H, $OCH_2CH_2O$), 3.72 (m, 4H, $OCH_2$), 3.64 (m, 2H, $CH_2NH$), 3.55 (m, 1H, CHS), 3.33 (dd, 1H, J1=12.0 Hz, J2=4.8 Hz, 1H, CHHexoS), 3.23 (t, 2H, J=6 Hz, $CH_2$—$NH_2$), 3.22, (1H, dd, J=5.0, 14.1 Hz, $CH_2$), 2.88, (1H, dd, J=5.0, 14.1 Hz, $CH_2$), 2.68 (d, 1H, J=12.45 Hz, CHHendoS), 2.20 (t, 2H, J=7.5 Hz, $CH_2CO$), δ 1.4 (m, 6H, biotin-$CH_2$). $^{13}C$ NMR (75 MHz, CD3OD): δ 175.0, 164.9, 156.9, 152.5, 151.3, 129.9, 128.2, 128.1, 127.2, 127.1, 126.0, 125.7, 123.8, 121.2, 112.7, 109.8, 76.8, 70.2, 70.1, 69.8, 69.4, 62.1, 60.4, 55.8, 54.6, 46.0, 42.6, 40.6, 39.9, 39.1, 35.5, 28.6, 28.3, 25.6, 17.5, 16.1, 12.0; MALDI HRMS: m/z 643.2575 [M+Na+]. Calcd for $C_{33}H_{40}N_4NaO_6S$ 643.2566.

General Procedure for Click Reactions with Carbohydrates and Peptides

3-Hydroxy-7,8-didehydro-1,2:5,6-dibenzocyclooctene (2.2 mg, 0.01 mmol) was dissolved in $CH_3OH$ (1 mL) and an azide (3-azidopropyl 2,3,4,6-tetra-O-acetate-α-D-mannopyranoside, 1-O-[dimethyl(1,1,2-trimethylpropyl)silyl]-4,6-O-isopropylidene-2-azido-2-deoxy-β-Dglucopyranose, 4,7,8-tri-O-acetyl-5-acetamido-9-azido-2,3-anhydro-3,5,9-trideoxy-D-glycero-D-galacto-non-2-enonic methyl ester, and 4-azido-N-[(1,1-dimethylethoxy)carbonyl]-Lphenylalanine, 1.0 equivalents) was added. The reaction was monitored by TLC, and after stirring the reaction mixture for 30 minutes at room temperature, the reaction had gone to completion. The solvents were evaporated under reduced pressure and the residue was purified by silica gel column chromatography to afford the desired products 10-13 respectively in quantitative yields.

Compound 10; $^1H$ NMR (500 MHz, $CDCl_3$): δ 7.83 (1H, m, aromatics), 7.58-6.99 (7H, m, aromatics), 5.33-4.98 (4H, m, 2-H, 3-H, 4-H, CHOH), 4.90-4.61 (1H, m, 1-H), 4.26, 4.10 (2H, m, 6-H), 3.93 (1H, m, 5-H), 3.70-3.60 (2H, m, $OCH_2CH_2$), 3.58-3.41 (2H, m, $CH_2N$), 3.31, 3.20, 3.06, 2.91 (2H, m, $CHOHCH_2$), 2.35-1.94 (12H, m, $CH_3CO$), 1.38-1.14 (2H, m, $CH_2CH_2N$); $^{13}C$ NMR (75 MHz, $CDCl_3$): δ 170.9, 170.2, 148.5, 146.9, 145.5, 144.9, 141.2, 139.3, 138.0, 136.7, 135.5, 133.8, 133.0, 132.3, 131.6, 130.3, 129.5, 129.0, 128.3, 127.7, 127.2, 126.5, 125.0, 124.2, 98.0, 97.4, 70.1, 69.5, 68.8, 66.2, 65.4, 64.9, 64.4, 62.6, 47.0, 45.1, 40.5, 32.1, 31.1, 30.6, 29.9, 22.9, 20.9, 14.3; MALDI HRMS: m/z 674.2330 [M+Na+]. Calcd for $C_{33}H_{37}N_3NaO_{11}$ 674.2326.

Compound 11; $^1H$ NMR (500 MHz, $CDCl_3$): δ 7.80, 7.65 (1H, d, J=7.5 Hz, aromatics), 7.48-7.06 (7H, aromatics), 5.82, 5.72, 5.60, 5.48 (1H, d, J=7.09 Hz, 1-H), 5.13-4.60 (1H, m, CHOH), 4.40-4.20 (2H, m, 2-H, 3-H), 4.10-3.90 (2H, m, 5-H, 6-H), 3.89-3.63 (1H, m, 6-H), 3.54-3.40 (2H, m, 4-H, HCH-CHOH), 3.07, 2.66 (1H, m, HCHCHOH), 1.54-1.20 (6H, m, $CH(CH_3)C(CH_3)_2$), 0.98-0.60 (13H, m, $2CH_3$, $CH(CH_3)_2$), 0.35-0.19 (6H, m, $Si(CH_3)_2$); $^{13}C$ NMR (75 MHz, $CDCl_3$): δ 151.0, 149.2, 148.5, 148.0, 146.1, 145.3, 142.4, 141.6, 140.8, 139.4, 138.1, 136.6, 135.7, 134.9, 133.4, 132.4, 131.6, 130.6, 129.5, 128.9, 127.1, 103.5, 100.4, 99.8, 80.6, 73.3, 70.9, 69.3, 68.8, 65.5, 50.1, 46.6, 45.4, 44.4, 37.3, 33.3, 32.5, 28.4, 23.4, 22.6, 21.9, 4.6, 1.4, 0.7, 0.0; MALDI HRMS: m/z 630.2980 [M+Na+]. Calcd for $C_{33}H_{45}N_3NaO_6Si$ 630.2975.

Compound 12; $^1H$ NMR (500 MHz, $CDCl_3$): δ 7.95-7.69 (1H, m, aromatics), 7.60-7.03 (7H, m, aromatics), 6.77-6.26 (1H, m), 5.98-8.81 (1H, m), 5.80-5.61 (1H, m), 5.58-5.33 (1H, m), 5.32-5.16 (2H, m), 5.16-4.94 (1H, m), 4.93-4.80 (1H, m), 4.69-4.34 (1H, m), 4.24-4.06 (1H, m), 3.95-3.60 (3H, m), 3.53-2.90 (2H, m), 2.32-1.57 (12H, m); $^{13}C$ NMR (75 MHz, $CDCl_3$): δ 169.6, 160.5, 147.8, 145.5, 145.1, 144.6, 143.9, 140.5, 138.7, 138.2, 137.1, 135.7, 134.5, 133.5, 132.7, 132.2, 131.8, 131.2, 130.8, 129.5, 129.0, 128.3, 127.7, 127.2, 126.5, 125.9, 124.8, 122.7, 108.0, 107.5, 75.1, 69.6, 68.8, 67.1, 66.6, 52.8, 51.7, 47.3, 46.4, 45.3, 28.7, 28.3, 22.0, 19.8; MALDI HRMS: m/z 699.2282 [M+Na+]. Calcd for $C_{34}H_{36}N_4NaO_{11}$ 699.2278.

Compound 13; $^1H$ NMR (300 MHz, CD3OD): δ 7.8-6.8 (12H, m, aromatics), 5.33, 5.17 (1H, dd, J=5.1, 10.5 Hz CHOH), 4.37 (1H, m, CHCOOH), 3.8, 3.23 3.77, 3.20 (2H, m, $CH_2CHOH$), 3.21, 2.93 (2H, m, $CH_2CHNH$), 1.35 (9H, m, $C(CH_3)_3$); $^{13}C$ NMR (75 MHz, CD3OD): δ 156.6, 145.1, 414.3, 139.6, 139.4, 138.0, 137.3, 136.1, 135.3, 135.0, 133.7, 133.4, 132.1, 131.7, 130.6, 130.3, 130.0, 129.5, 129.2, 128.8, 128.3, 128.0, 127.6, 126.9, 126.6, 126.6, 126.2, 125.3, 125.1, 124.8, 79.4, 76.8, 76.2, 68.6, 58.5, 54.9, 46.2, 40.5, 37.1, 29.6, 29.3, 27.5; MALDI HRMS: m/z 549.2118 [M+Na+]. Calcd for $C_{30}H_{30}N_4NAO_5$ 49.2114.

N-Boc-3,6-dioxaoctczne-1,8-diamine

A solution of di-tert-butyl dicarbonate (di-Boc) (6 g, 28 mmol, 0.5 equiv) in $CH_2Cl_2$ (100 mL) was added dropwise to a mixture of tris(ethylene glycol)-1,8-diamine (7.6 g, 56 mmol) and diisopropylethylamine (10 mL, 57 mmol) at room temperature over a period of 2 hours. The reaction mixture was stirred for 6 hours, after which it was concentrated in vacuo. Purification by flash silica gel column chromatography ($CH_2Cl_2/CH_3OH$, 10/1, v/v) afforded N-Boc-3,6-dioxaoctane-1,8-diamine (4.1 g, 58%). $^1H$ NMR (300 MHz, CD3OD): δ 3.6 (s, 4H), 3.54 (t, 2H), 3.53 (t, 2H), 3.24 (t, 2H), 2.8 (t, 2H), 1.4 (s, 9H); MALDI HRMS: m/z 271.1641 [M+Na+]. Calcd for $C_{11}H_{24}N_2NaO_4$ 271.1634.

N-Boc-N'-biotinyl-3,6-dioxaoctane-1,8-diamine

A solution of vitamin H (Biotin) (2.2 g, 9 mmol), O-benzotriazol-1-yl-N,N,N',N'-tetramethyluronium hexafluorophosphate (HBTU) (3 g, 8 mmol), and DIPEA (1.8 mL, 10 mmol) in DMF (100 mL) was stirred for 10 minutes at room temperature before being adding dropwise to a solution of N-Boc-3,6-dioxaoctane-1,8-diamine (1.5 g, 6 mmol, 1). The reaction mixture was stirred for 1 hour at room temperature, after which the DMF was removed in vacuo to give an oily residue, which was purified by flash silica gel column chromatography ($CH_2Cl_2/CH_3OH$, 25/1, v/v) to afford N-Boc-N'-biotinyl-3,6-dioxaoctane-1,8-diamine (2.0 g, 90%). $^1H$ NMR (300 MHz, CD3OD): δ 4.5 (m, 1H), 4.3 (m, 1H), 3.6 (s, 4H), 3.54 (tt, 4H), 3.39 (t, 2H), 3.26 (t, 2H), 2.9 (dd, 1H), 2.7 (d, 1H), 2.2 (t, 2H), 1.7-1.5 (m, 8H), 1.4 (s, 9H); MALDI HRMS: m/z 497.2416 [M+Na+]. Calcd for $C_{21}H_{38}N_4NaO_6S$ 497.2410.

N-Biotinyl-3,6-dioxaoctane-1,8-diamine (8)

N-Boc-N'-biotinyl-3,6-dioxaoctane-1,8-diamine (1.9 g, 4 mmol) was dissolved in 50% TFA in $CH_7Cl$, (20 mL) and stirred for 1 hour at room temperature. The solvents were evaporated under reduced pressure to give an oily residue, which was purified by flash silica gel column chromatography ($CH_2Cl_2/CH_3OH$, 10/1, v/v) to afford 7 (1.3 g, 92%). $^1H$ NMR (300 MHz, DMSO-d6): δ 7.85 (t, 1H, J=5.7 Hz, NHCO), 6.42, 6.35 (s, 2H, NH), 4.29, 4.11 (m, 2H, CHNH), 3.5 (s, 4H, $OCH_2CH_2O$), 3.3 (m, 4H, $OCH_2$), 3.16 (m, 2H, $CH_2NH$), 3.10 (m, 1H, CHS), 2.81 (dd, 1H, J1=12.0 Hz, J2=4.8 Hz, 1H, CHHexoS), 2.64 (t, 2H, J=6 Hz, $CH_2$—$NH_2$), 2.52 (d, 1H, J=12.45 Hz, CHHendoS), 2.06 (t, 2H, J=7.5 Hz, $CH_2CO$), 1.6 (s, 2H, $NH_2$), δ 1.4 (m, 6H, biotin-$CH_2$); $^{13}C$ NMR (75 MHz, DMSO-$d_6$): δ 171.9, 160.6, 71.7, 71.6, 69.5, 69.1, 64.4, 59.2, 55.0, 54.2, 40.7, 38.4, 35.1, 28.4, 28.1, 25.2; MALDI HRMS: m/z 397.1892 [M+Na+]. Calcd for $C_{16}H_{30}N_4NaO_4S$ 397.1885.

Reagents for Biological Experiments

Synthetic compounds 2 and 9 were reconstituted in DMF and stored at 80° C. Final concentrations of DMF never exceeded 0.56% to avoid toxic effects.

Cell Surface Azide Labeling and Detection by Fluorescence Intensity

Human Jurkat cells (Clone E6-1; ATCC) were cultured in RPMI 1640 medium (ATCC) with L-glutamine (2 mM), adjusted to contain sodium bicarbonate (1.5 g $L^{-1}$), glucose (4.5 g $L^{-1}$), HEPES (10 mM), and sodium pyruvate (1.0 mM) and supplemented with penicillin (100 u $mL^{-1}$)/streptomycin (100 micrograms $mL^{-1}$; Mediatech) and fetal bovine serum (FBS, 10%; Hyclone). Cells were maintained in a humid 5% CO, atmosphere at 37° C. Jurkat cells were grown in the presence of peracetylated N-azidoacetylmannosamine (Ac4ManNaz; 25 micromolar final concentration) for 3 days, leading to the metabolic incorporation of the corresponding N-azidoacetyl sialic acid (SiaNAz) into their cell surface glycoproteins. Jurkat cells bearing azides and untreated control cells were incubated with the biotinylated compounds 2 and 9 (0-100 micromolar) in labeling buffer (DPBS, supplemented with FBS (1%)) for 0-180 minutes at room temperature. The cells were washed three times with labeling buffer and then incubated with avidin conjugated with fluorescein (Molecular Probes) for 15 minutes at 4° C. Following three washes and cell lysis, cell lysates were analysed for fluorescence intensity (485 ex/520 em) using a microplate reader (BMG Labtech). Data points were collected in triplicate and are representative of three separate experiments. Cell viability was assessed at different points in the procedure with exclusion of trypan blue.

Cell Labeling and Detection by Fluorescence Microscopy

Chinese hamster ovary (CHO) cells (Clone KI; ATCC) were cultured in Kaighn's modification of Ham's F-12 medium (F-12K) with L-glutamine (2 mM), adjusted to contain sodium bicarbonate (1.5 g $L^{-1}$) and supplemented with penicillin (100 u $mL^{-1}$)/streptomycin (100 micrograms $mL^{-1}$ and FBS (10%). Cells were maintained in a humid 5% $CO_2$ atmosphere at 37° C. CHO cells were grown in the presence of Ac4ManNaz (100 micromolar final concentration) for 3 days to metabolically incorporate SiaNAz into their cell surface glycoproteins. CHO cells bearing azides and untreated control cells were then transferred to a glass coverslip and cultured for 36 hours in their original medium. Live CHO cells were treated with the biotinylated compound 9 (30 micromolar) in labeling buffer (DPBS, supplemented with FBS (1%)) for 1 hour at 4° C. or at room temperature, followed by incubation with avidin conjugated with Alexa Fluor 488 (Molecular Probes) for 15 minutes at 4° C. Cells were washed 3 times with labeling buffer and fixed with formaldehyde (3.7% in PBS) or incubated for 1 hour at 37° C. before fixation. The nucleus was labeled with the far red fluorescent TO-PRO-3 dye (Molecular Probes). The cells were mounted with PennaFluor (Thermo Electron Corporation) before imaging. Initial analysis was performed on a Zeiss Axioplan2 fluorescent microscope. Confocal images were acquired using a 60× (NA1.42) oil objective. Stacks of optical sections were collected in the z dimensions. The step size, based on the calculated optimum for each objective, was between 0.25 and 0.5 micrometers. Subsequently, each stack was collapsed into a single image (z-projection). Analysis was performed offline using ImageJ 1.39f software (National Institutes of Health, USA) and Adobe Photoshop CS3 Extended Version 10.0 (Adobe Systems Incorporated), whereby all images were treated equally.

Example 2

Alkyne Reagents Containing Biotin and a Cleavable Linker

Azides, which are extremely rare in biological systems, are emerging as attractive chemical handles for bioconjugation (Dedola et al., Org. Biomol. Chem. 2007, 5, 1006; Kolb and Sharpless, Drug Dis. Today 2003, 8, 1128; Moses and Moorhouse, Chem. Soc. Rev. 2007, 36, 1249; Nandivada et al., Adv. Mater. 2007, 19, 2197; Wu and Fokin, Aldrichimica ACTA 2007, 40, 7; Agard et al., ACS Chem. Biol. 2006, 1, 644). In particular, the Cu(I) catalyzed 1,3-dipolar cyclization of azides with terminal alkynes to give stable triazoles has been employed for tagging a variety of biomolecules including proteins, nucleic acids, lipids, and saccharides (Chin et al., Science 2003, 301, 964; Gierlich et al., Org. Lett. 2006, 8, 3639; Kho et al., Proc. Natl. Acad. Sci. 2004, 101, 12479; Link et al., Proc. Natl. Acad. Sci. 2006, 103, 10180; Wang et al., J. Am. Chem. Soc. 2003, 125, 3192). The cycloaddition has also been used for activity-based protein profiling (Speers et al., *J. Am. Chem. Soc.* 2003, 125, 4686), monitoring of enzyme activity, and the chemical synthesis of microarrays and small molecule libraries (Sun et al., *Bioconjugate Chem.* 2006, 17, 52).

An attractive approach for installing azides into biomolecules is based on metabolic labeling whereby an azide containing biosynthetic precursor is incorporated into biomolecules using the cells' biosynthetic machinery (Prescher and Bertozzi, *Nat. Chem. Biol.* 2005, 1,13). This approach has been employed for tagging proteins, glycans, and lipids of living systems with a variety of reactive probes. These probes can facilitate the mapping of saccharide-selective glycoproteins and identify glycosylation sites (Hanson et al., *J. Am. Chem. Soc.* 2007, 129, 7266). Alkyne probes have also been used for cell surface imaging of azide-modified bio-molecules and a particularly attractive approach involves the generation of a fluorescent probe from a non-fluorescent precursor by a [3+2] cycloaddition (Sivakumar et al., *Org. Lett.* 2004, 6, 4603).

Figure 9:
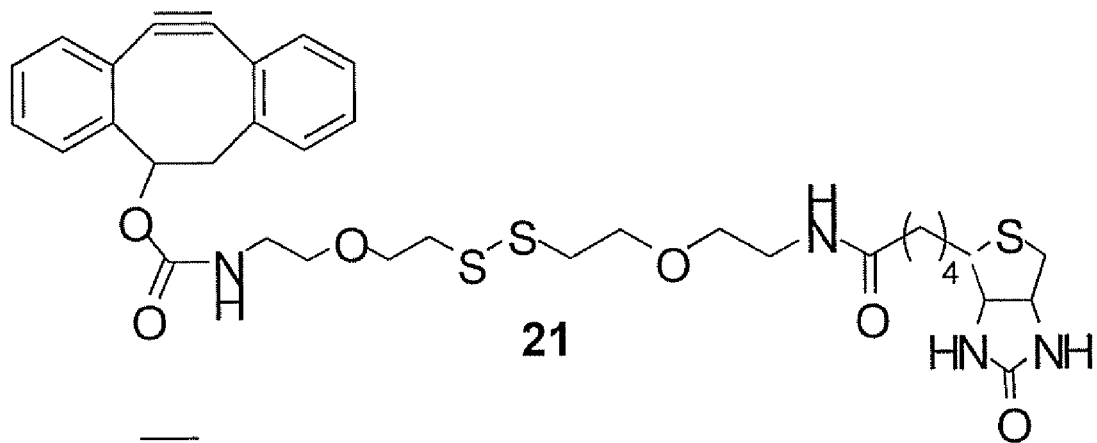
FIG. 9 illustrates exemplary compounds comprising an alkyne fragment, a cleavable linker fragment, and a biotinylated fragment.
Figure 9:
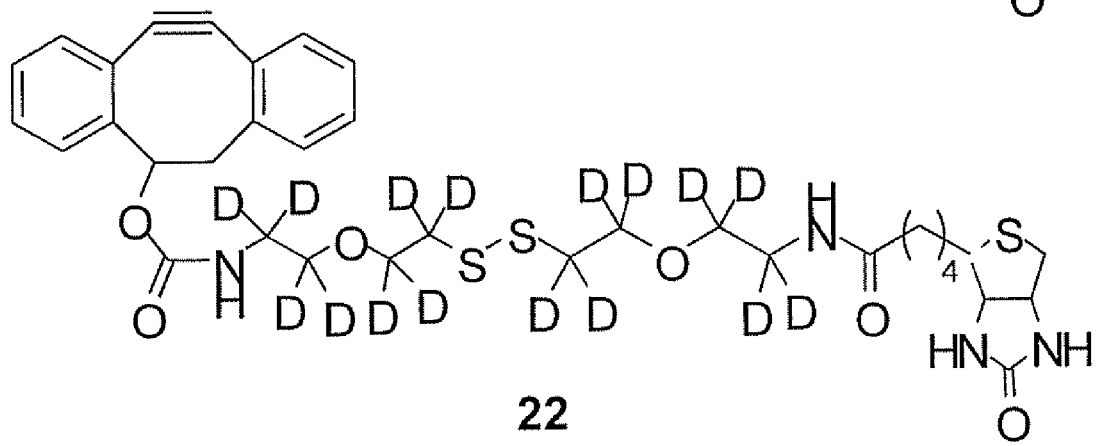

We describe here reagents including an alkyne fragment, a cleavable linker fragment, and biotin. Such compounds are expected to be valuable for biological research. Thus, the alkyne fragment of the reagent can react with various biomolecules containing an azide fragment to give stable triazole adducts. The biotin fragment gives an opportunity to retrieve the tagged compounds by affinity chromatography using immobilized avidin. The cleavable linker allows the release of tagged and captured biomolecules for analysis. For example, released proteins or glycoproteins can be characterized by standard proteomics or glycomics analysis (Tao, *Expert Rev. Proteomics* 2007, 4, 603; Bantscheff et al., *Anal. Bioanal. Chem.* 2007, 389, 1017; Lau et al., *Proteomics* 2007, 7, 2787). Release of the proteins and glycoproteins is much more practical than previously reported analysis of biomolecules attached to immobilized avidin (Hanson et al., *J. Am. Chem. Soc.* 2007, 129, 7266). Compound 21 is an example of the new class of reagent (FIG. 9). It contains a 4-dibenzocyclooctynol fragment for reaction with azides, a disulfide, which can be cleaved with reducing reagents such as dithiothreitol (DTT), and biotin.

The quantification of differences between physiological states of a biological system is a technically challenging task in proteomics (Tao, *Expert Rev. Proteomics* 2007, 4, 603; Bantscheff et al., *Anal. Bioanal. Chem.* 2007, 389, 1017; Lau et al., *Proteomics* 2007, 7, 2787). In addition, to the classical methods of differential protein gel or blot staining by dyes and fluorophores, mass-spectrometry-based quantification methods is gaining popularity. Most of the latter methods employ differential stable isotope labeling to create a specific mass tag that can be recognized by a mass spectrometer and at the same time provide the basis for quantification. These mass tags can be introduced into proteins or peptides by (i) metabolical labeling, (ii) by chemical means, (iii) enzymatically, or (iv) by spiking with synthetic peptide standards.

Figure 10:
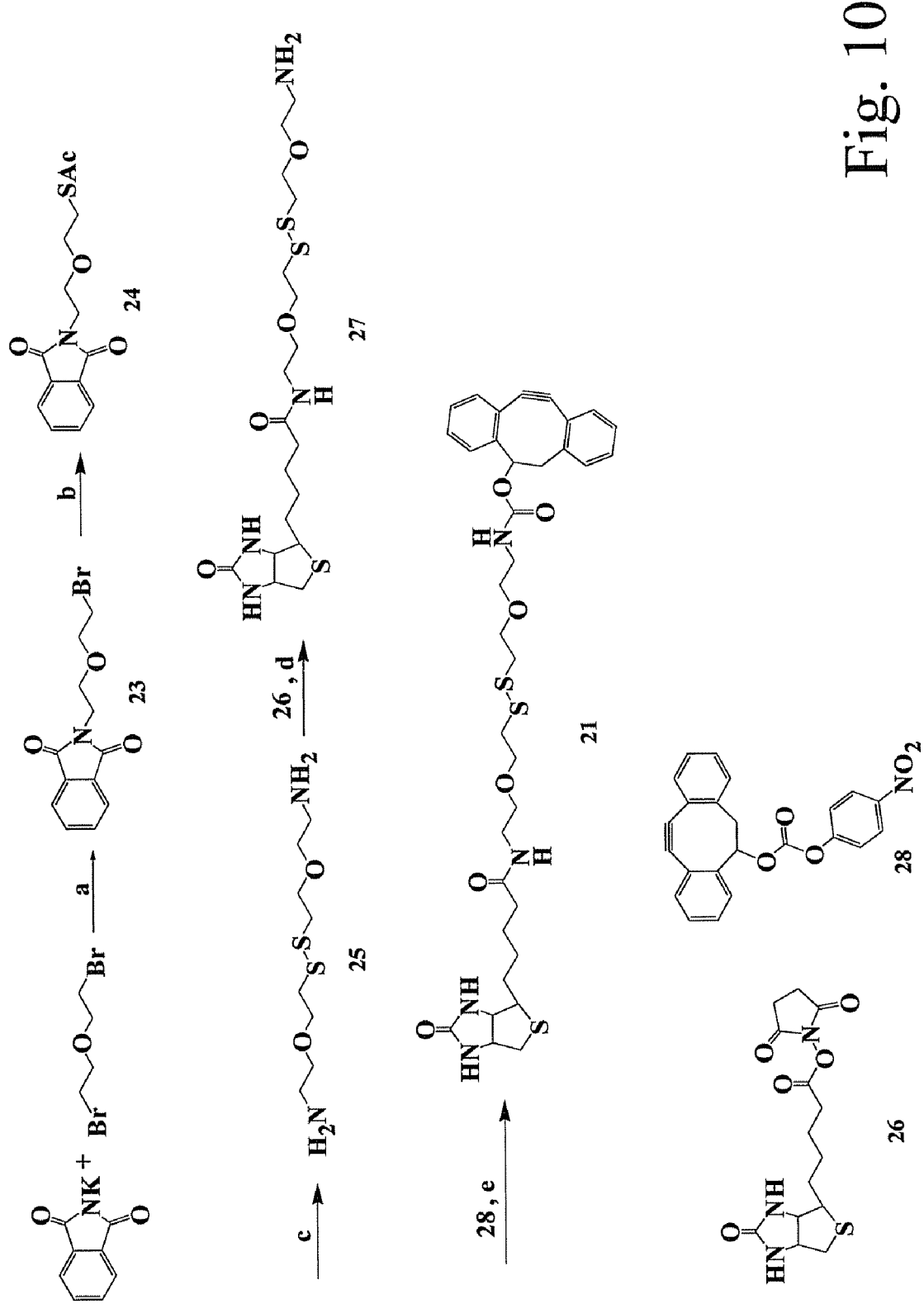
FIG. 10 illustrates Scheme 4: exemplary reaction conditions: a) DMF, 80° C., 70%; b) potassium thioacetate (KSAc), DMF, 60° C., 90%; c) NH$_2$NH$_2$, ethanol (EtOH), refluxing, 95%; d) N,N-diisopropylethylamine (DIPEA), DMF, 0° C., 56%; e) DIPEA, DMF, room temperature, 85%.
Figure 11:
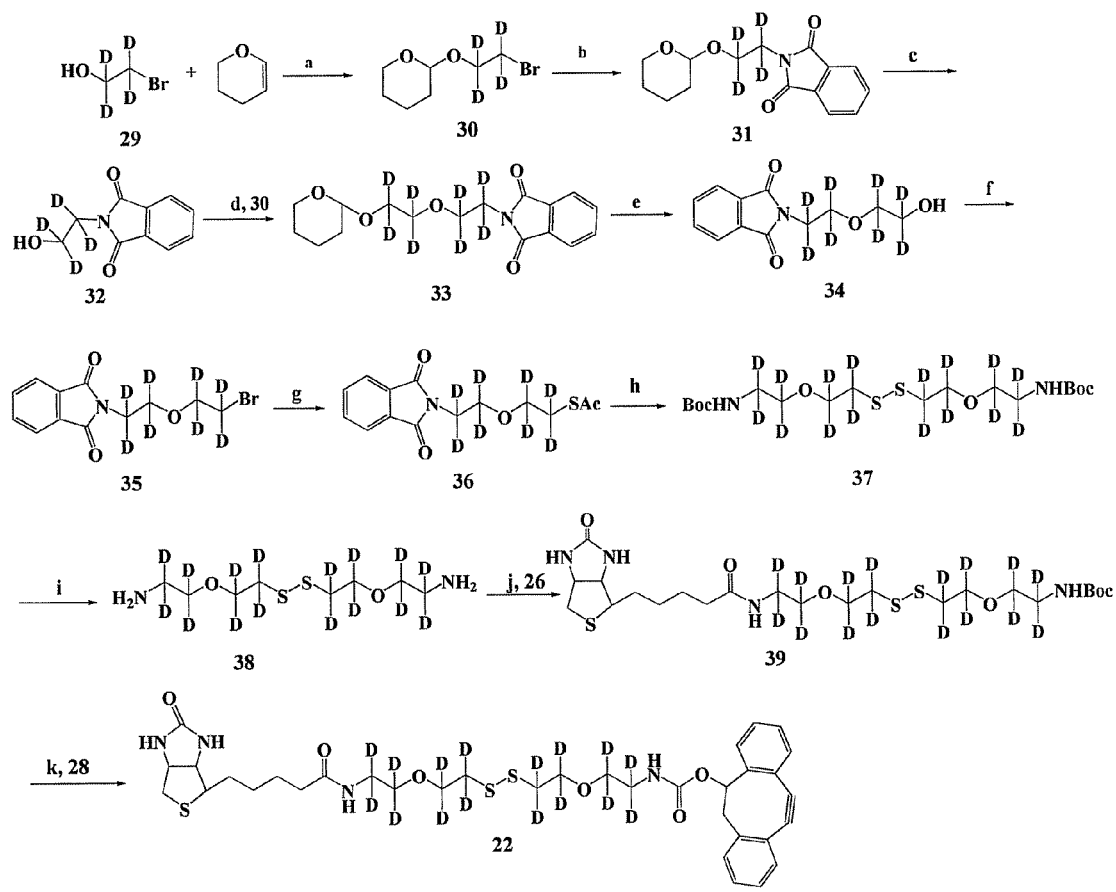
FIG. 11 illustrates Scheme 5: exemplary reaction conditions: a) p-toluenesulfonic acid (TsOH), room temperature, 81%; b) DMF, 80° C., 86%; c) 0.1N HCl, EtOH, room temperature, 90%; d) 9, NaH, DMF, 0° C., 88%; e) 0.1N HCl, EtOH, room temperature, 88%; f) CCl$_4$, PPh$_3$, dichloromethane (DCM), room temperature, 96%; g) KSAc, DMF, 60° C., 90%; h) NH$_2$NH$_2$, EtOH, refluxing, 95%; then (Boc)$_2$O, TEA, EtOH, 91%; i) 20% TFA, DCM, room temperature, 95%; j) DIPEA, DMF, 0° C.; then (Boc)$_2$O, TEA, EtOH, 60% over two steps; k) 20% TFA, DCM, room temperature, then 8 DIPEA, DMF, room temperature, 80% over two steps.
Figure 12:
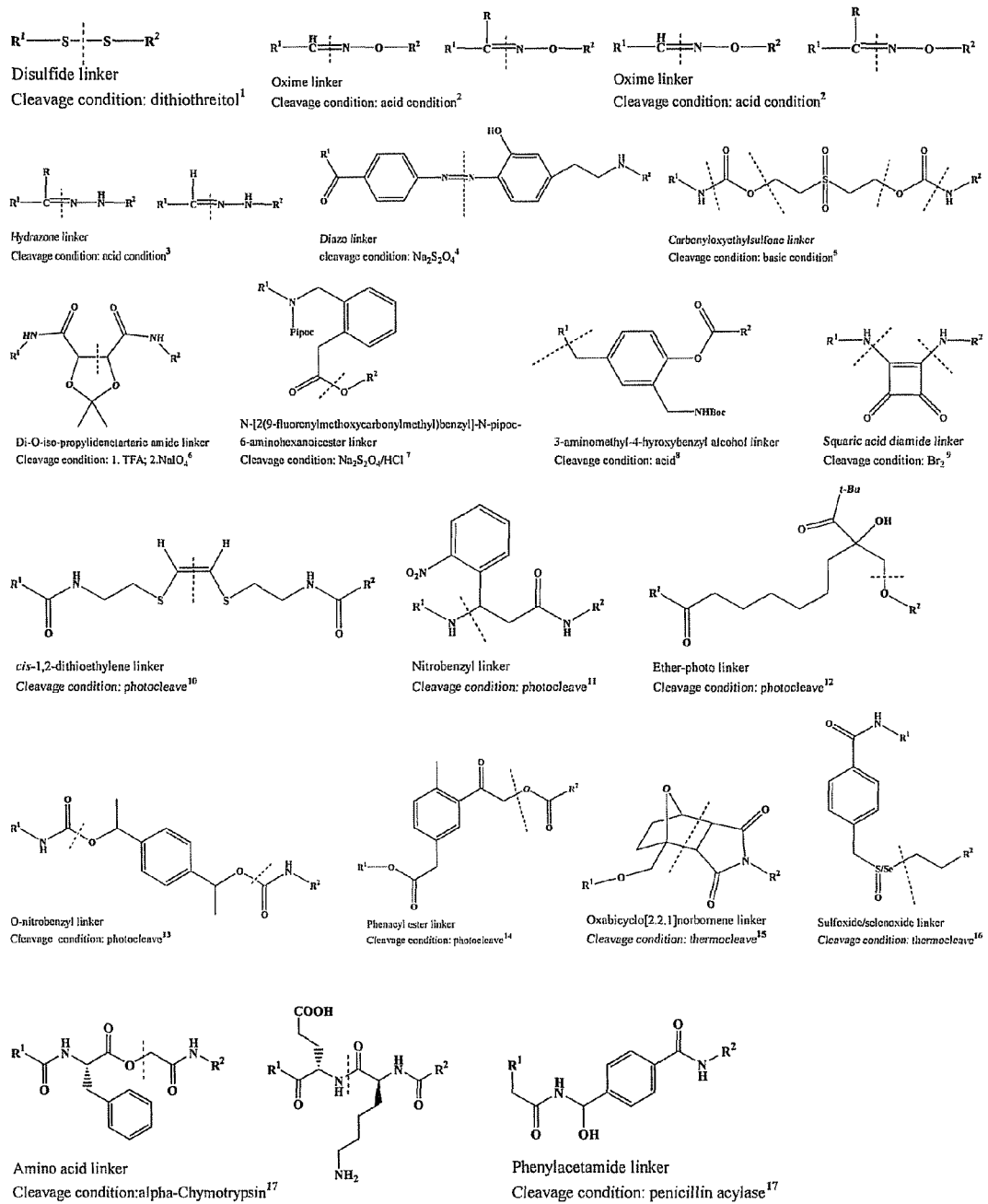
FIG. 12 illustrates exemplary cleavable linkers.
Figure 13:
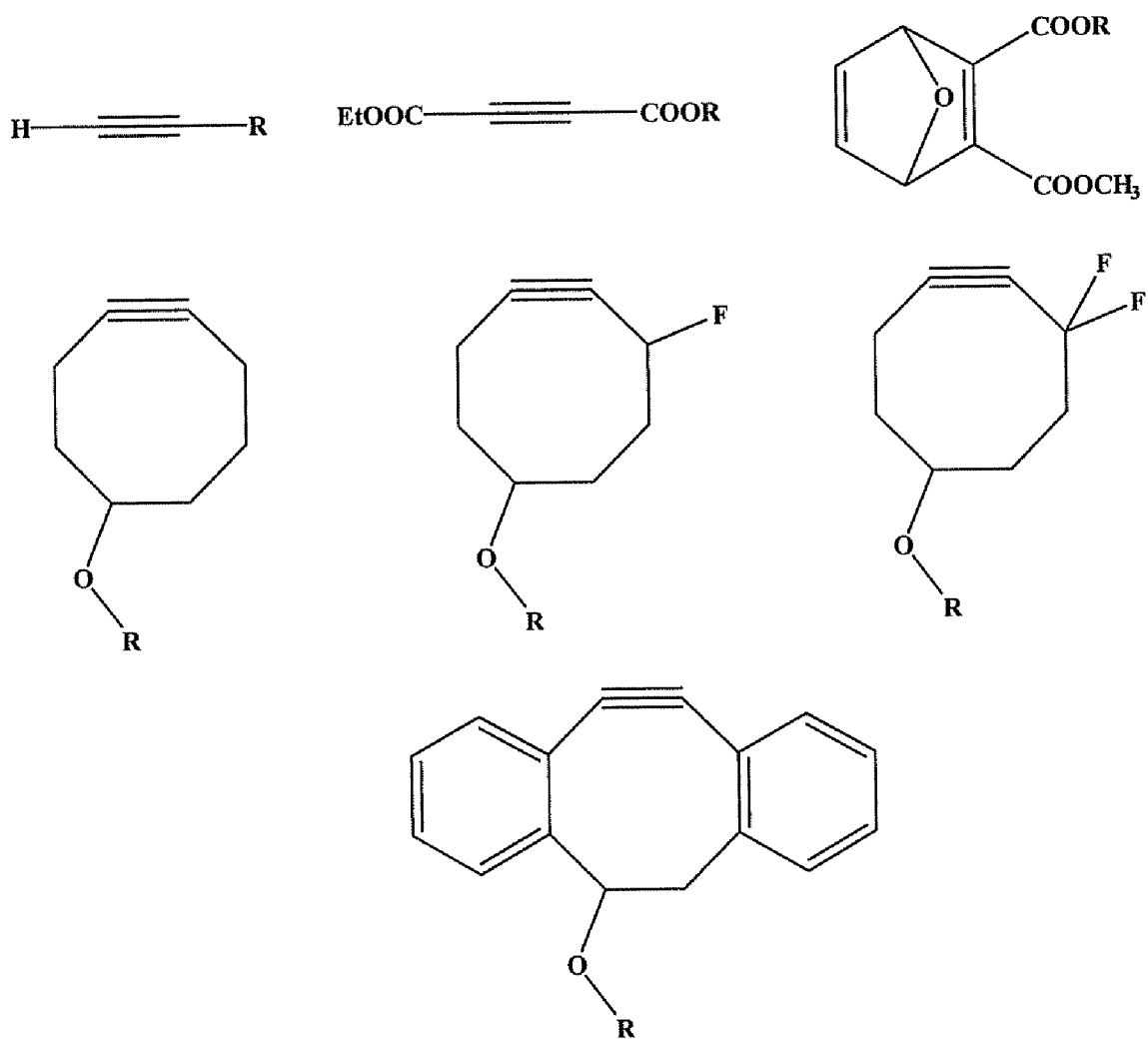
FIG. 13 illustrates exemplary alkynes and a reactive diene.

Reagents composed of an alkyne, a cleavable linker and biotin can be employed to introduce mass tags into proteins, glycoproteins and other biomolecules containing an azide fragment. Thus, by employing reagents such as 21 and 22, different mass tags can be introduced to quantify proteins, glycoproteins, glycopeptides, peptides and carbohydrates. The chemical synthesis of 21 and 22 is depicted in Schemes 4 and 5, respectively (FIGS. 10 and 11). Various alkyne moieties, cleavable linkers and biotin derivatives are depicted in FIG. 12 and alkyne and reactive diene derivatives are depicted in FIG. 13.

Example 3

Fast Click Reactions for Labeling of Living Cells and Nanoparticles

An Alternative Approach for Preparing 4-Dibenzcyclooctynol and Using this Compound for the Preparation of Amine Containing Click Reagents.

Figure 14:
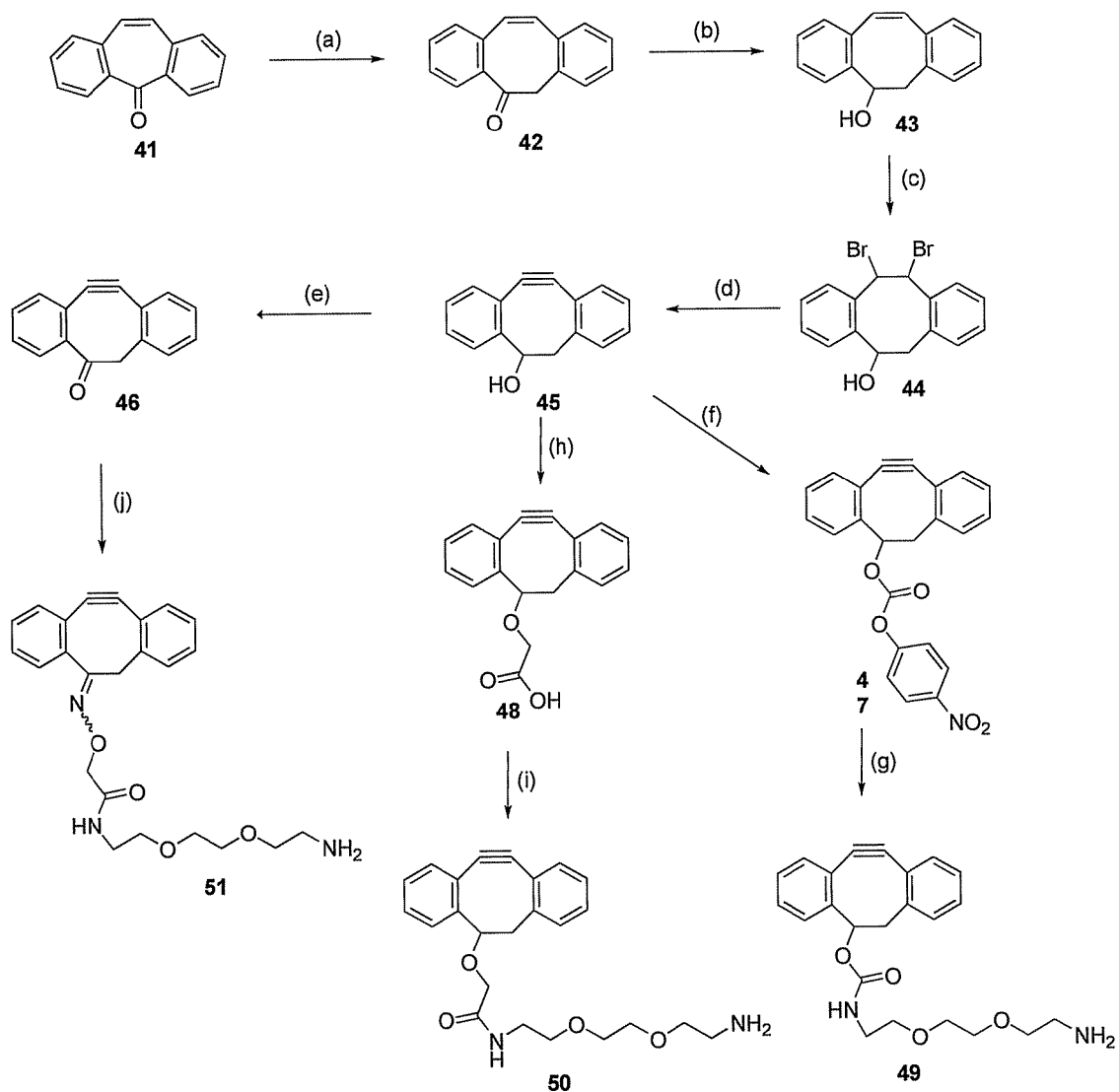
FIG. 14 illustrates scheme 6: exemplary reaction conditions: a) TMSCH$_2$N$_2$, BF$_3$OEt$_2$, DCM, −10° C., 3 hours, 71%; b) NaBH$_4$, 1:1 EtOH/THF, room temperature, 7 hours, 100%; C) Br$_2$, CHCl$_3$, room temperature, 0.5 hour, 58%; d) LDA, THF, 0.5 hour, 57%; e) Dess-Martin reagent, DCM, 0.5 h; f) 4-nitrophenyl chloroformate, pyridine, DCM, 18 hours, 92%; g) tris(ethylene glycol)-1,8-diamine, TEA, DCM, room temperature, 3 hours, 80%; h) bromoacetic acid, NaH, THF, 22%; i) tris(ethylene glycol)-1,8-diamine, HATU coupling reagent, DIPEA, DMF, room temperature, 2 hours, 75%; j)

4-Dibenzocyclooctynol 45 could be prepared by an alternative synthetic route (Scheme 6; FIG. 14). Thus, known of dibenzosuberenone (41) was treated trimethylsilyl diazomethane in the presence of $BF_3.OEt_2$ in $CH_2Cl_2$ (20 ml) at −10° C. to give 6H-Dibenzo[a,e]cyclooctatrien-5-one (42) in good yield. The ketone of 42 was reduced with sodium borohydride in a mixture of ethanol and THF to give alcohol 43, which could be converted into 4-dibenzocyclooctynol 45 by bromination of the double bond followed by elimination of the resulting compound 44 by treatment LDA in THF. Compound 45 could be oxidized to the corresponding ketone 46 by employing Dess-Martin reagent.

Compounds 45 and 46 were converted into amine containing derivatives 49, 50 and 51. The attraction of these compounds is that the can easily be derivatized with various probes such as fluorescent tags and biotin. Furthermore, the amine gives an easy chemical handle for attachment to polymeric supports. Thus, alcohol 45 was converted into p-nitrophenyl ester 49 by reaction with 4-nitro-phenyl chloroformate (0.4 g, 2 mmol) and pyridine. The target compound compound 49 was obtained by reaction of 49 with an excess of tris(ethylene glycol)-1,8-diamine. Compound 50 was obtained by reaction of 46 with bromoacetic acid in the presence of lithium diisopropylamide in tetrahydrofuran followed by condensation of the resulting acid 48 with tris(ethylene glycol)-1,8-diaminein DMF in the presence of the coupling reagent HATU and the base DIPEA. Finally, derivative 51 was prepared by oxime formation be reaction of ketone 51 with N-{2-[2-(2-amino-ethoxy)-ethoxy]-ethyl}-2-aminooxy-acetamide (84 mg, 0.251 mmol) in the presence of acetic acid and in a mixture of methanol and dichloromethane. A feature of 51 is that the oxime linkage can be cleaved by treatment with aqueous acid to detach the captured compound from the click reagent.

Experimental

6H-Dibenzo[a,e]cyclooctatrien-5-one (42). To a stirred solution of dibenzosuberenone 41 (2.888 g, 14.0 mmol) and $BF_3.OEt_2$ (2.59 ml, 21.0 mmol) in $CH_2Cl_2$ (30 ml) was added dropwise a solution of trimethylsilyl diazomethane (10.5 ml, 21.9 mmol) in $CH_2Cl_2$ (20 ml) at −10° C. over 1 hour. The mixture was stirred at −10° C. for 2 hours, and then poured into ice water. The aqueous layer was extracted with $CH_2Cl_2$ (3×100 ml) and the organic layers were combined. The combined organic layers were washed with brine and dried ($MgSO_4$). The solvent was removed under reduced pressure, and the crude product was purified by flash chromatography on silica gel (2:1-1:2 v/v hexanes/$CH_2Cl_2$) to give the product as pale solid (2.220 g, 72%). $^1H$ NMR (300 MHz, $CDCl_3$): δ 8.26 (1H, q, J=1.4, 6.6 Hz), 7.13-7.43 (7H, m), 7.05 (2H, q, J=3.8, 12.9 Hz), 4.06 (2H, s). $^{13}C$ NMR (75 MHz, $CDCl_3$): δ 196.6, 136.9, 136.3, 135.4, 133.8, 133.1, 132.4, 131.4, 130.6, 129.3, 128.8, 128.0, 127.3, 126.9, 48.4. MALDI HRMS: m/z [M+Na$^+$]. Calcd for $C_{16}H_{12}NaO$: 243.0786 (Chaffins, S.; Brettreich, M.; Wudl, F. Synthesis 2002, 1191-1194).

5,6-Dihydro-dibenzo[a,e]cycloocten-5-ol (43). To a stirred solution of 42 (2.203 g, 10 mmol) in 1:1 EtOH/THF (120 ml) at room temperature was added slowly sodium borohydride (0.757 g, 20 mmol), and the reaction mixture was stirred at room temperature for 7 hours. TLC indicated that the reaction was complete, and the reaction mixture was quenched by slow addition of acetic acid (1 ml). The solvent was evaporated, and the residue was dissolved in $CH_2Cl_2$ (100 ml) and brine (100 ml), extracted with $CH_2Cl_2$ (4×100 ml). The organic phase was combined, dried ($MgSO_4$) and evaporated to give the product as white solid (2.223 g, 100%), which is directly used in the next step reaction without further purification. $^1H$ NMR (300 MHz, $CDCl_3$): δ 7.50 (1H, m), 7.14-7.30 (7H, m), 6.90 (2H, q, J=2.7, 12.0 Hz), 5.31 (1H, q, J=6.3, 10.0 Hz), 3.41 (2H, m). $^{13}C$ NMR (75 MHz, $CDCl_3$): δ 141.7, 136.7, 136.2, 134.5, 131.7, 131.5, 130.1, 129.9, 129.3, 128.7, 127.4, 127.2, 126.9, 125.9, 74.4, 42.7. MALDI HRMS: m/z [M+Na$^+$]. Calcd for $C_{16}H_{14}NaO$: 245.0942.

11,12-Dibromo-5,6, 11,12-tetrahydro-dibenzo [a,e]cycloocten-5-ol (44). To a stirred solution of 43 (2.223 g, 10 mmol) in 1:1 $CHCl_3$ (50 ml) at room temperature was added dropwise bromine (0.512 ml, 10 mmol), and the reaction mixture was stirred at room temperature for 0.5 hour TLC indicated that the reaction was complete, and the solvent was removed at room temperature under reduced pressure. The residue was purified by flash chromatography on silica gel (2:1-1:2 v/v hexanes/$CH_2Cl_2$) to give the product as yellowish oil (2.220 g, 58%). $^1H$ NMR (300 MHz, $CDCl_3$): δ 7.54-7.47 (2H, aromatics), 7.31-6.72 (6H, aromatics), 5.77 (1H, d, J=5.4 Hz, CHBr), 5.22 (1H, dd, J=3.6, 15.9 Hz, CHOH), 5.19 (1H, d, J=5.4 Hz, CHBr), 3.50 (1H, dd, J=3.6, 15.9 Hz, $CH_2$), 2.75 (1H, dd, J=3.6, 15.9 Hz, $CH_2$). $^{13}C$ NMR (75 MHz, $CDCl_3$): δ 141.3, 140.0, 137.2, 134.0, 133.4, 131.5, 131.3, 130.9, 127.8, 126.2, 123.7, 121.3, 76.5, 70.0, 62.3, 32.2. MALDI HRMS: m/z 402.9313 [M+Na$^+$]. Calcd for $C_{16}H_{14}Br_2NaO$: 402.9309.

5,6-Dihydro-11,12-didehydro-dibenzo[a,e]cycloocten-5-ol (45). To a stirred solution of 44 (1.528 g, 4 mmol) in tetrahydrofuran (40 ml) was added dropwise lithium diisopropylamide in tetrahydrofuran (2.0 M) (8 ml, 16 mmol) under an atmosphere of Argon at room temperature. The reaction mixture was stirred for 0.5 hour at room temperature, after which it was quenched by addition of dropwise water (0.5 ml). The solvents were evaporated under reduced pressure, and the residue was purified by flash chromatography on silica gel (2:1-0:1 v/v hexanes/$CH_2Cl_2$) to give the product as white solid (0.503 g, 57%). $^1H$ NMR (300 MHz, $CDCl_3$): δ 7.67 (1H, aromatics), 7.37-7.18 (7H, aromatics), 4.57 (1H, dd, J=2.1, 14.7 Hz, CHOH), 3.04 (1H, dd, J=2.1, 14.7 Hz, $CH_2$), 2.86 (1H, dd, J=2.1, 14.7 Hz, $CH_2$). $^{13}C$ NMR (75 MHz, $CDCl_3$): δ154.5, 150.6, 128.6, 127.1, 1127.0, 126.0, 125.8, 125.1, 124.7, 123.0, 122.7, 121.7, 111.9, 109.6, 74.2, 47.7.

6H-11,12-Didehydro-dibenzo [a,e]cyclooctatrien-5-one (46). To a stirred solution of 45 (0.172 g, 0.781 mmol) in $CH_2Cl_2$ (40 ml) was added Dess-Martin reagent (0.397 g, 0.937 mmol). The reaction mixture was stirred for 0.5 hour at room temperature, TLC indicated that the reaction was complete. The reaction mixture was filter through a short pad of silica gel, and washed with $CH_2Cl_2$. The filtrate was concentrated, and the residue was purified by flash chromatography on silica gel (1:1-0:1 v/v hexanes/$CH_2Cl_2$) to give the product as white solid (0.158 g, 93%). $^1H$ NMR (300 MHz, $CDCl_3$): δ 7.29-7.57 (8H, m), 4.17 (1H, d, J=10.6 Hz), 3.64 (1H, J=10.6 Hz). $^{13}C$ NMR (75 MHz, $CDCl_3$): δ 200.4, 154.7, 148.2, 131.21 (2 C), 131.18, 129.3, 128.2, 127.8, 126.3, 125.9, 122.2, 111.1, 109.4, 49.3.

MALDI HRMS: m/z [M+Na$^+$]. Calcd for $C_{16}H_{10}NaO$: 241.0629.

Carbonic acid 5,6-dihydro-11,12-didehydro-dibenzo[a,e]cycloocten-5-yl ester 4-nitro-phenyl ester (47). To a solution of 45 (0.22 g, 1 mmol) in $CH_2Cl_2$ (30 mL) was added 4-nitro-phenyl chloroformate (0.4 g, 2 mmol) and pyridine (0.4 ml, 5 mmol). After stirring 4 hours at ambient temperature, the reacting mixture was washed with brine (2×10 mL), and the organic layer was dried ($MgSO_4$). The solvents were evaporated under reduced pressure, and the residue was purified by silica gel column chromatography (hexane/ethyl acetate, 10/1, v/v) to afford 47 (0.34 g, 89%). $^1H$ NMR (300 MHz, $CDCl_3$): δ 8.23-8.18 (2H, aromatics), 7.56-7.54 (2H, aromatics), 7.46-7.18 (8H, aromatics), 5.52 (1H, dd, J=3.9, 15.3 Hz, CHOH), 3.26 (1H, dd, J=3.9, 15.3 Hz, $CH_2$), 2.97 (1H, dd, J=3.9, 15.3 Hz, $CH_2$). $^{13}C$ NMR (75 MHz, $CDCl_3$): δ 154.5, 150.7, 149.1, 148.7, 129.0, 127.4, 127.3, 126.7, 126.5, 125.5, 125.2, 124.3, 124.0, 122.6, 122.4, 120.8, 120.6, 120.2, 112.2, 108.5, 80.6, 44.8. MALDI HRMS: m/z 408.0852 [M+ Na$^+$]. Calcd for $C_{23}H_{15}NNaO_5$: 408.0848.

(5,6-Dihydro-11,12-didehydro-dibenzo[a,e]cycloocten-5-yloxy)-acetic acid (48). To a stirred solution of bromoacetic acid (0.280 g, 2 mmol) in tetrahydrofuran (40 ml) at 0° C. was added slowly sodium hydride (60% oil dispersion, 0.120 g, 3.0 mmol). The mixture was stirred at 0° C. for 10 minutes, then 45 (0.220 g, 1.0 mmol) was added. The mixture was stirred at 0° C. for another 10 minutes, then warmed to room temperature and stirred for 1 day. The reaction was quenched by 1 drop of HOAc, filtered through a short pad of silica gel washed by EtOAc, then concentrated under reduced pressure. The residue was purified by flash chromatography on silica gel (1:0-1:1 $CH_2Cl_2$/EtOAc) to give the product as white solid (0.60 g, 22%). $^1H$ NMR (300 MHz, $CDCl_3$): δ 7.69 (1H, d, J=7.7 Hz), 7.49 (1H, d, J=6.7 Hz), 7.41 (1H, m), 7.27-7.35 (5H, m), 4.25 (1H, m), 4.15 (2H, d, J=8.0 Hz), 3.30 (1H, dd, J=2.2, 14.8 Hz), 2.72 (1H, dd, J=3.6, 14.8 Hz). $^{13}C$ NMR (75 MHz, $CDCl_3$): δ 154.5, 150.6, 128.6, 127.1, 1127.0, 126.0, 125.8, 125.1, 124.7, 123.0, 122.7, 121.7, 111.9, 109.6, 74.2, 47.7. MALDI HRMS: m/z 301.0838 [M+Na$^+$]. Calcd for $C_{18}H_{14}NaO_3$: 301.0841.

{2-[2-(2-Amino-ethoxy)-ethoxy]ethyl}-carbamic acid 5,6-dihydro-11,12-didehydro-dibenzo[a,e]cycloocten-5-yl ester (49). To a stirred solution of 47 (0.077 g, 0.2 mmol) and tris(ethylene glycol)-1,8-diamine (0.293 ml, 2 mmol) in $CH_2Cl_2$ (20 ml) at room temperature was added $Et_3N$ (0.139 ml, 1.0 mmol). The reaction mixture was stirred for 3 hours at room temperature, after which the solvent was removed under reduced pressure. The residue was purified by flash chromatography on Iatrobeads (8-30% v/v MeOH/$CH_2Cl_2$) to give the product as yellowish solid (0.063 g, 80%). $^1H$ NMR (300 MHz, $CDCl_3$): δ 7.51 (1H, d, J=7.3 Hz), 7.24-7.37 (7H, m), 5.81 (1H, s, NH), 5.48, (1H, br), 3.50-3.68 (8H, m), 3.39 (2H, m), 3.16 (1H, d, J=14.8 Hz), 2.91 (2H, br), 2.88 (1H, d, J=14.8 Hz), 2.57 (2H, br, $NH_2$). $^{13}C$ NMR (75 MHz, $CDCl_3$): δ 155.7, 152.2, 151.1, 130.0, 128.1, 128.0, 127.2, 127.1, 126.3, 126.0, 123.9, 123.8, 121.3, 113.0, 110.0, 76.7, 72.8, 70.3, 70.2, 70.1, 70.0, 46.2, 41.5, 41.0. MALDI HRMS: m/z 417.1746 [M+Na$^+$]. Calcd for $C_{23}H_{26}N_2NaO_4$: 417.1790.

N-{2-[2-(2-Amino-ethoxy)-ethoxy]-ethyl}-2-(5,6-dihydro-11,12-didehydro-dibenzo[a,e]cycloocten-5-yloxy)-acetamide (50). To a stirred solution of 48 (5.6 mg, 0.02 mmol) and tris(ethylene glycol)-1,8-diamine (0.0292 ml, 0.2 mmol) in DMF (3 ml) at room temperature was added HATU coupling reagent (7.6 mg, 0.02 mmol) and DIPEA (0.0348 ml, 0.2 mmol). The reaction mixture was stirred for 2 hours at room temperature, after which the solvent was removed under reduced pressure. The residue was purified by flash chromatography on Iatrobeads (8-30% v/v MeOH/$CH_2Cl_2$) to give the product as colorless oil. MALDI HRMS: m/z 431.1916 [M+Na$^+$]. Calcd for $C_{24}H_{28}N_2NaO_4$: 431.1947.

N-{2-[2-(2-Amino-ethoxy]-ethyl}-2-(6H-11,12-didehydro-dibenzo[a,e]cycloocten-5-ylideneaminooxy)-acetamide (51). A solution of 46 (46 mg, 0.211 mmol), N-{2-[2-(2-amino-ethoxy)-ethoxy]-ethyl}-2-aminooxy-acetamide (84 mg, 0.251 mmol) and acetic acid (0.1 ml) in 1:1 v/v MeOH/$CH_2Cl_2$ (4 ml) was stirred at room temperature for 2 days. The solvent was removed under reduced pressure, and the residue was purified by flash chromatography on Iatrobeads (4-15% v/v MeOH/$CH_2Cl_2$) to give the product as yellowish solid. (56 mg, 63%). MALDI HRMS: m/z 444.1835 [M+Na$^+$]. Calcd for $C_{24}H_{27}N_3NaO_4$: 444.1899.

Reaction Kinetics of Cycloaddition of Derivatives of 4-Dibenzocyclooctynol.

A number of analogs (63-68) of 4-dibenzocyclooctynol (61) were prepared and the influence of these modifications on the reaction rate of the cycloaddition with benzyl azide was determined by integration of the benzylic proton signals in $^1$H NMR spectrum. FIG. 15 shows the second order constant of compounds 61-68. A surprising finding was that compound 62, which does not have a hydroxyl function, reacts approximately 70-times slower that the analogous 4-dibenzocyclooctynol (61). Acylation of the hydroxyl of 61 such as in compounds 63 and 64, led to a slow reduction in reaction rate. Alkylation of 61, as in compound 65, also resulted in a slower rate of reaction. Compound 66, which has a gem-difluoride reacted at a similar rate as compound 61. Interestingly, ketone 67 reacts with a slightly higher reaction rate than 1. Oxime 68 has a similar reaction than 61. These results demonstrate that modification of the hydroxyl of 61 can have a dramatic influence on the rate of cycloaddition.

Experimental

Synthesis of 70. To a stirring solution of LiAlH$_4$ (0.38 g, 10 mmol) and AlCl$_3$ (1.3 g, 10 mmol) in Et$_2$O (100 mL) was added 69 (1.1 g, 5 mmol). The reaction was kept at 0° C. for 12 hours, and then it was quenched with water (100 ml). The aqueous layer was extracted with ether (4×100 ml), and the combined organic extracts were washed with water (100 ml) and brine (100 ml). The crude product was purified by column chromatography (hexane/$CH_2Cl_2$, 2/1, v/v) to yield two 70 (0.63 g, 61%; Scheme 7; FIG. 16). $^1$H NMR (CDCl$_3$, 300 MHz) δ: 6.90-7.21 (m, 8H, aromatics), 6.67 (s, 2H, CH=CH), 3.11 (s, 4H, —CH$_2$—CH$_2$—). $^{13}$C NMR (75 MHz, CDCl$_3$) δ: 140.0, 136.9, 131.6, 130.3, 130.1, 128.7, 128.5, 127.1, 125.6. HRMS calcd for $C_{16}H_{14}Na$ (M+Na): 229.0993. Found: 229.1003.

Synthesis of 71. A solution of bromine (0.4 g, 2.5 mmol) in CHCl$_3$ (10 mL) was added dropwise to a solution of 70 (0.5 g, 2.5 mmol) in CHCl$_3$ (20 mL) at 0° C. The reaction mixture was stirred at room temperature for 12 hours until the reaction was complete (monitored by TLC). The resulting mixture was washed with aqueous saturated sodium thiosulfate solution (15 mL), and dried (MgSO$_4$). The solvents were evaporated under reduced pressure and the residue was purified by silica gel column chromatography (hexane/$CH_2Cl_2$, 10/1, v/v) to afford 71 (0.53 g, 58%; Scheme 7; FIG. 16). $^1$H NMR (CDCl$_3$, 300 MHz) δ: 7.06-7.52 (m, 8H, aromatics), 5.79 (s, 2H, Ph-CH—Br), 3.05 (dd, 2H, PhHCH), 2.84 (m, 2H, PhHCH). $^{13}$C NMR (75 MHz, CDCl$_3$) δ: 141.8, 138.7, 131.3, 130.6, 129.3, 126.6, 35.7.

Synthesis of 62. To a solution of 71 (0.36 g, 1 mmol) in tetrahydrofuran (20 mL) was added dropwise t-BuOK in tetrahydrofuran (2.0 M), (2 mL) under an atmosphere of Argon at room temperature. The reaction mixture was stirred for 2 hours at room temperature, after which it was poured into ice water (10 mL) and the resulting mixture was extracted with $CH_2Cl_2$ (2×50 mL). The combined extracts were washed with water, brine and dried (MgSO$_4$) and the solvents were evaporated under reduced pressure. The residue was purified by silica gel column chromatography (hexane/$CH_2Cl_2$, 2/1, v/v) to afford 62 (50 mg, 25%; Scheme 7; FIG. 16). $^1$H NMR (CDCl$_3$, 300 MHz) δ: 7.29-7.14 (m, 8H, aromatics), 3.28-3.15 (m, 2H, —HCH—HCH—), 2.40-2.27 (m, 2H, —HCH—HCH—). $^{13}$C NMR (75 MHz, CDCl$_3$) δ: 153.8, 129.6, 127.9, 126.7, 126.3, 124.2, 111.8, 36.7.

Synthesis of 63. To a stirring solution of 72 (38 mg, 0.1 mmol) in $CH_2Cl_2$ (15 mL) was added 73 (15 mg, 0.2 mmol) and TEA (10 μL). The reaction mixture was stirred at room temperature for 12 hours. The solvents were evaporated under reduced pressure and the residue was purified by silica gel column chromatography ($CH_2Cl_2/CH_3OH$, 20/1, v/v) to afford 63 (25 mg, 77%; Scheme 8; FIG. 17). $^1$H NMR (CDCl$_3$, 300 MHz) δ: 6.94-7.43 (m, 8H, aromatics), 5.42 (m, 1H, Ph-CH—O), 3.61 (m, 2H, CH$_7$OH), 3.30 (m, 2H, CH$_2$NH), 3.08 (dd, 1H, J=15.0, 1.8 Hz, PhHCH), 2.84 (dd, 1H, J=15.0, 3.9 Hz, PhHCH), 1.53-1.68 (m, 2H, CH$_2$CH$_2$OH). $^{13}$C NMR (75 MHz, CDCl$_3$) δ: 150.8, 149.1, 128.9, 128.0, 127.0, 126.1, 126.0, 125.9, 125.8, 125.3, 125.1, 125.0, 122.8, 122.6, 120.3, 111.9, 108.9, 58.6, 45.2, 36.8, 36.7, 31.6. HRMS calcd for $C_{20}H_{19}O_3Na$ (M+Na): 344.1263. Found: 344.1896.

Synthesis of 64. To a stirring solution of 61 (22 mg, 0.1 mmol) in pyridine (4 mL) was added Ac$_2$O (1 mL). The reaction mixture was stirred at room temperature for 12 hours. The solvents were evaporated under reduced pressure and the residue was purified by silica gel column chromatography (hexane/$CH_2Cl_2$, 1/1, v/v) to afford 64 (21 mg, 81%; Scheme 9; FIG. 18). $^1$H NMR (CDCl$_3$, 300 MHz) δ: 7.43-7.17 (m, 8H, aromatics), 5.49 (m, 1H, Ph-CH—OAc), 3.06 (dd, 1H, J=15.6, 2.4 Hz, PhHCH), 2.84 (dd, 1H, J=15.6, 2.4 Hz, PhHCH), 2.17 (s, 3H, CH$_3$). $^{13}$C NMR (75 MHz, CDCl$_3$) δ: 169.9, 151.3, 151.1, 130.1, 128.3, 128.1, 127.4, 127.3, 126.5, 126.2, 124.0, 121.6, 113.2, 110.0, 76.6, 46.5, 21.4. HRMS calcd for $C_{18}H_{14}O_2Na$ (M+Na): 285.0891. Found: 285.1005.

Synthesis of 65. To a stirring solution of 61 (22 mg, 0.1 mmol) in DMF (2 mL) was added NaH (8 mg, 0.2 mmol), the mixture was stirred at room temperature for 1 hour and then benzyl bromide (BnBr, 34 mg, 0.2 mmol) was added. The reaction mixture was stirred at room temperature for 12 hours. The solvents were evaporated under reduced pressure and the residue was purified by silica gel column chromatography (hexane/$CH_2Cl_2$, 2/1, v/v) to afford 65 (18 mg, 59%; Scheme 9; FIG. 18). $^1$H NMR (CDCl$_3$, 300 MHz) δ: 7.70 (m, 1H, aromatics), 7.39-7.17 (m, 13H, aromatics), 4.55 (dd, 2H, J=11.6, 3.0 Hz, CH$_2$Ph), 4.26 (m, 1H, Ph-CH—OBn), 3.23 (dd, 1H, J=15.0, 2.4 Hz, PhHCH), 2.84 (dd, 1H, J=15.0, 2.4 Hz, PhHCH). $^{13}$C NMR (75 MHz, CDCl$_3$) δ: 152.6, 151.1, 137.3, 128.4, 127.3, 127.1, 127.0, 126.5, 126.2, 125.8, 125.7, 125.1, 125.0, 123.6, 123.0, 120.5, 111.8, 109.5, 81.5, 71.0, 46.1. HRMS calcd for $C_{23}H_{18}ONa$ (M+Na): 333.1255. Found: 333.1905.

Synthesis of 74. To a stirring solution of LDA (20 ml, 40 mmol, 2.0 M solution in THF) in THF (200 mL) at room temperature was added a solution of ketone 69 (4.4 g, 20 mmol) in THF (40 mL) over 1 hour using a syringe pump. After an additional 20 minutes of stirring at room temperature, chlorotriethylsilane (6.7 ml, 40 mmol) was added. The solution was stirred at room temperature for 1 hour. The reaction mixture was concentrated on a rotary evaporator, and the crude product was purified directly by column chromatography (hexane/$CH_2Cl_2$, 10/1, v/v) to yield a clear oil 74 (5.8 g, 85%; Scheme 10; FIG. 19). $^1$H NMR (CDCl$_3$, 300 MHz) δ: 7.25-6.95 (m, 8H, aromatics), 6.72 (t, 2H, J=7.0 Hz, CH=CH), 6.11 (s, 1H, J=7.0 Hz, CH=C), 0.87-0.82 (m, 9H, CH$_2$—CH$_3$), 0.61-0.48 (m, 6H, CH$_2$—CH$_3$). $^{13}$C NMR (75 MHz, CDCl$_3$) δ: 151.9, 138.2, 137.3, 137.2, 136.7, 136.5, 134.0, 132.6, 130.1, 129.3, 129.0, 128.6, 128.0, 127.1, 127.0, 126.2, 112.7, 6.9, 5.1. HRMS calcd for $C_{22}H_{26}OSiNa$ (M+Na): 357.1651. Found: 357.1993.

Synthesis of 75. To a stifling solution of fluorinating reagent (1-chloromethyl-4-fluoro-1,4-diazoniabicyclo[2.2.2]octane bis-(tetrafluoroborate)) available under the trade designation SELECTFLUOR from Air Products (Allentown, Pa.) (6.3. g, 18 mmol) in DMF (20 ml) at 0° C. was added a solution of silyl enol ether 74 (5.0 g, 15 mmol) DMF (20 ml) via an addition funnel over 10 minutes. The reaction was allowed to slowly warm to room temperature while stirring over 30 minutes, and then it was quenched with water (100 mL). The aqueous layer was extracted with ether (4×100 ml), and the combined organic extracts were washed with water (3×100 mL) and brine (1×200 mL). The crude product was purified by column chromatography (hexane/$CH_2Cl_2$, 1/1, v/v) to yield 75 (2.4 g, 66%; Scheme 10; FIG. 19). $^1H$ NMR ($CDCl_3$, 300 MHz) δ: 7.80-7.06 (m, 8H, aromatics), 6.85 (s, 2H, CH=CH), 4.41-4.36 (m, 1H, CHF). $^{13}C$ NMR (75 MHz, $CDCl_3$) δ: 196.4, 152.8, 144.1, 140.4, 138.5, 135.8, 135.5, 135.4, 131.5, 129.6, 128.3, 127.7, 126.9, 125.3, 124.6, 124.1, 63.6, 56.9; $^{19}F(CDCl_3$, 283 MHz) δ: –109.1 (s, 1F). HRMS calcd for $C_{16}H_{11}FONa$ (M+Na): 261.0692. Found: 261.1237.

Synthesis of 76. To a stirring solution of LDA (10 ml, 20 mmol, 2.0 M solution in THF) in THF (100 mL) at room temperature was added a solution of ketone 75 (2.4 g, 10 mmol) in THF (20 mL) over 1 hour using a syringe pump. After an additional 20 minutes of stirring at room temperature, chlorotriethylsilane (3.3 ml, 20 mmol) was added. The solution was stirred at room temperature for 1 hour. The reaction mixture was concentrated on a rotary evaporator, and the crude product was purified directly by column chromatography (hexane/$CH_2Cl_2$, 5/1, v/v) to yield a clear oil 76 (2.8 g, 79%; Scheme 10; FIG. 19). $^1H$ NMR ($CDCl_3$, 300 MHz) δ: 7.41 (m, 2H, aromatics), 7.22 (m, 4H, aromatics), 7.08 (m, 2H, aromatics), 6.91 (s, 2H, CH=CH), 0.94 (t, 9H, J=7.8 Hz, $CH_2$—$CH_3$), 0.63 (m, 6H, CH)—$CH_3$). $^{13}C$ NMR (75 MHz, $CDCl_3$) δ: 145.8, 142.6, 137.3, 137.2, 136.3, 136.1, 134.2, 133.3, 132.6, 132.1, 130.1, 130.0, 129.6, 129.3, 128.9, 128.8, 128.7, 128.5, 128.2, 127.5, 127.4, 6.7, 6.3, 5.2; $^{19}F(CDCl_3$, 283 MHz) δ: –111.978 (s, 1F). HRMS calcd for $C_{22}H_{23}FOSiNa$ (M+Na): 373.1400. Found: 373.1522.

Synthesis of 77. To a stirring solution of SELECTFLUOR fluorinating reagent (3.5. g, 10 mmol) in DMF (15 ml) at 0° C. was added a solution of silyl enol ether 76 (2.8 g, 8 mmol) DMF (10 ml) via an addition funnel over 10 minutes. The reaction was allowed to slowly warm to room temperature while stirring over 30 minutes, and then it was quenched with water (100 mL). The aqueous layer was extracted with ether (4×100 mL), and the combined organic extracts were washed with water (3×100 mL) and brine (1×100 mL). The crude product was purified by column chromatography ($CH_2Cl_2$) to yield 77 (1.0 g, 51%; Scheme 10; FIG. 19). $^1H$ NMR ($CDCl_3$, 300 MHz) δ: 8.05 (m, 1H, aromatics), 7.69 (m, 1H, aromatics), 7.51 (m, 1H, aromatics), 7.39-7.21 (m, 5H, aromatics), 6.92 (d, 1H, CH=CH, J=14.8 Hz), 6.73 (d, 1H, CH=CH, J=14.8 Hz). $^{13}C$ NMR (75 MHz, $CDCl_3$) δ: 188.1, 134.6, 133.6, 132.8, 132.3, 131.1, 130.8, 130.5, 130.1, 129.8, 129.6, 129.3, 126.8, 15.0, 124.8, 115.3; $^{19}F(CDCl_3$, 283 MHz) δ: —110.1 (s, 2F). HRMS calcd for $C_{16}H_{10}F_2ONa$ (M+Na): 279.0597. Found: 279.1032.

Synthesis of 78. To a stirring solution of 77 (1.0 g, 4 mmol) in EtOH (30 mL) was added $NaBH_4$ (0.3 g, 8 mmol) over 5 minutes. The reaction was kept at room temperature for 2 hours, and then it was quenched with water (100 ml). The aqueous layer was extracted with $CH_2Cl_2$ (3×100 mL), and the combined organic extracts were washed with water (100 mL) and brine (100 mL). The crude product was purified by column chromatography (hexane/EtOAc, 5/1, v/v) to yield 78 (0.78 g, 78%; Scheme 10; FIG. 19). $^1H$ NMR ($CDCl_3$, 300 MHz) δ: 7.02-7.74 (m, 8H, aromatics), 6.94 (d, 1H, J=12.3 Hz, CH=CH), 6.85 (d, 1H, J=12.3 Hz, CH=CH), 5.60 (m, 1H, Ph-CH—OH), 2.82 (m, 1H, OH). $^{13}C$ NMR (75 MHz, $CDCl_3$) δ: 136.0, 135.9, 135.0, 133.8, 131.2, 130.6, 130.0, 128.1, 127.9, 126.8, 124.6, 121.5, 121.4; $^{19}F(CDCl_3$, 282 MHz) δ: —69.8 (d, 1F, J=259.4 Hz), –111.7 (dd, 1F, J=259.4, 21.4 Hz). HRMS calcd for $C_{16}H_{12}F_2ONa$ (M+Na): 281.0754. Found: 281.1122.

Synthesis of 79. To a stirring solution of bromine (0.16 g, 1.0 mmol) in $CHCl_3$ (10 mL) was added dropwise to a solution of 78 (0.25 g, 1.0 mmol) in $CHCl_3$ (10 mL) at 0° C. The reaction mixture was stirred at room temperature for 12 hours until the reaction was complete (monitored by TLC). The resulting mixture was washed with aqueous saturated sodium thiosulfate solution (10 mL), and dried ($MgSO_4$). The solvents were evaporated under reduced pressure and the residue was purified by silica gel column chromatography (hexane/EtOAc, 8/1, v/v) to afford 79 (0.19 g, 46%; Scheme 10; FIG. 19). $^1H$ NMR ($CDCl_3$, 300 MHz) δ: 6.96-7.82 (m, 8H, aromatics), 5.62 (d, 1H, J=10.8 Hz, Ph-CH—Br), 5.17 (d, 1H, J=10.8 Hz, PhHCH). $^{13}C$ NMR (75 MHz, $CDCl_3$) δ: 132.7, 132.4, 131.0, 130.8, 129.2, 129.0, 128, 128.4, 128.3, 127.8, 125.4, 123.8, 111.5, 57.3, 56.5, 50.5; $^{19}F(CDCl_3$, 282 MHz) δ: —98.8 (d, 1F, J=341.1 Hz), –110.4 (d, 1F, J=341.1 Hz).

Synthesis of 66. To a stirring solution of 79 (40 mg, 0.1 mmol) in tetrahydrofuran (10 mL) was added dropwise t-BuOK in tetrahydrofuran (2.0 M), (0.5 mL) under an atmosphere of Argon at room temperature. The reaction mixture was stirred for 6 hours at room temperature, after which it was poured into ice water (10 mL) and the resulting mixture was extracted with $CH_2Cl_2$ (2×50 mL). The combined extracts were washed with water, brine and dried ($MgSO_4$) and the solvents were evaporated under reduced pressure. The residue was purified by silica gel column chromatography (hexane/EtOAc, 5/1, v/v) to afford 66 (10 mg, 49%; Scheme 10; FIG. 19). $^1H$ NMR ($CDCl_3$, 300 MHz) δ: 7.19-7.92 (m, 8H, aromatics), 5.39 (d, 1H, J=23.4, 10.8 Hz, —CH—OH). $^{13}C$ NMR (75 MHz, $CDCl_3$) δ: 131.3, 129.5, 129.4, 128.4, 127.9, 127.5, 126.8, 126.6, 125.9, 125.7, 124.8, 124.5, 120.3, 107.3, 82.8; $^{19}F(CDCl_3$, 282 MHz) δ: —91.5 (d, 1F, J=253.8 Hz). –103.4 (d, 1F, 1=253.8 Hz).

(6H-11,12-didehydro-dibenzo [a,e]cycloocten-5-ylideneaminooxy)-acetic acid (68). A solution of 6H-11,12-didehydro-dibenzo[a,e]cyclooctatrien-5-one 67 (21.8 mg, 0.1 mmol) and carboxymethyl)hydroxylamine hemihydrochloride (21.8 mg, 0.2 mmol) in 1:1:0.02 v/v/v MeOH/$CH_2Cl_2$/HOAc (8 ml) was stirred at room temperature for 2 days. The solvent was removed under reduced pressure, and the residue was purified by flash chromatography on silica gel (EtOAc) to give the product as white solid (17.8 mg, 61%). $^1H$ NMR (300 MHz, $CDCl_3$): δ 7.54 (1H, d, J=7.4 Hz), 7.46 (1H, d, J=7.4 Hz), 7.18-7.39 (6H, m), 4.53 (2H, m), 4.23 (1H, d, J=12.8 Hz), 3.16 (1H, d, J=12.8 Hz). $^{13}C$ NMR (75 MHz, $CDCl_3$): δ 175.2 & 173.6, 154.1 153.2, 130.7, 129.5, 19.3, 129.2, 129.1, 128.1, 128.0, 127.1, 126.9, 125.5, 125.2, 122.7, 113.9, 111.2, 84.7, 68.3 & 67.1, 35.0 & 33.2. MALDI HRMS: m/z 314.0810 [M+Na+]. Calcd for $C_{18}H_{13}NNaO_3$: 314.0793.

Modification of Macromolecules and Nano-Material Using Cycloadditions with 4-Dibenzocyclooctynol The Cu(I) catalyzed 1,3-dipolar cycloaddition of azides with terminal alkynes to give stable triazoles has been employed for tagging a variety of biomolecules including proteins, nucleic acids, lipids, and saccharides. This reaction has also been used to modify polymers and nanoscale materials. Potential difficulties to remove Cu(I), which is highly cytotoxic, complicates the use of the 1,3-dipolar cycloaddition for conjugation of compounds or material for biological or medical application. The use of 4-dibenzocyclooctynol instead of a terminal alkyne for cycloadditions with azides should overcome this problem.

To demonstrate the use of 4-dibenzocyclooctynol in bioconjugation, co-block polymers 83 and 84 were prepared. These materials were employed to form organomicelles in water and it was shown that 4-dibenzocyclooctyne fragment of these materials can be reacted was with azido containing molecules (FIGS. 20A, B).

It is well known that co-block polymers composed of a polyester and polyethyleneglycol fragment self-assemble in water to form organomicelles. These nano-materials have attracted attention as drug delivery devises. Derivatization of organomicelles with, for example, tissue or tumor targeting moieties may lead to smart drug delivery devises. In addition, modification of organomicelles with fluorescent tags or MRI reagents, such as biotin, will be valuable for imaging purposes (FIG. 20C).

Copolymerization of polyethylene glycol methyl ether (81) or azide (82) (MW ~2000 Da) with caprolactone in the presence of a catalytic amount of SnOct gave copolymers 83 and 84, respectively (Scheme 11; FIG. 21). The azido fragment of 84 was reduced with triphenylphosphine and the amine of the resulting polymer 85 was reacted with 86 and 87 to give dibenzocyclooctyl derivatives 88 and 89, respectively. A mixture of 83 and 88 or 89 (9/1, w/w) dissolved in a small amount of THF were added to water. Cryo-TEM showed that organomicelles that have a diameter of approximately 40 A were formed. The resulting micelles were incubated with azido-containing saccharide 90 and after a reaction time of 24 hours, unreacted saccharide was removed by dialysis. The micelles were analyzed for sugar content by hydrolysis with TFA followed by quantification by high pH anion exchange chromatography. It was established that approximately 45% of the cyclooctynes were modified by saccharides.

It is to be expected that compound 84 can also be employed for the formation of micelles and the azido moieties of the resulting azides employed in cycloaddition with compounds modified with a dibenzocyclooctyl fragment.

Experimental

Synthesis of $PEG_{44}$-b-$PCL_{26}$ 83. $PEG_{45}$-b-$PCL_{23}$ block copolymers were synthesized as reported. A predetermined volume (12.0 mL) of ε-caprolactone monomer was placed in a flask containing an amount (9.0 g) of PEG 81 under an argon atmosphere. Then, a drop of SnOct was added. After cooling to liquid-nitrogen temperature, the flask was evacuated for 12 hours, sealed off, and kept at 130° C. for 24 hours. The synthesized polymers were dissolved in THF, recovered by precipitation by cold hexane, and dried under vacuum at room temperature. The degree of polymerization of the PCL was calculated by $^1$H NMR relative to the degree of polymerization of the PEG 81.

Synthesis of azide-$PEG_{44}$-b-$PCL_{26}$ 84. Azide-PEG-b-PCL was synthesized by a one-pot cationic ring opening polymerization at 130° C. under a stream of argon adopting a previously reported method for the preparation of PEG-b-PCL with some modifications. Briefly, a predetermined volume (3.3 mL) of ε-caprolactone monomer was placed in a flask containing a preweighed amount (2.5 g) of azide-PEG-OH 82 under a nitrogen atmosphere. Then a drop of SnOct was added. After cooling to liquid-nitrogen temperature, the flask was evacuated, sealed off, and kept at 130° C. for 24 hours. The synthesized polymers were then dissolved in THF, recovered by precipitation into cold hexane, and dried under vacuum at room temperature. The number average molecular weight ($M_n$) of azide-$PEO_{44}$-b-$PCL_{26}$ 84 block copolymer was determined by $^1$H NMR.

Synthesis of amine-$PEG_{44}$-b-$PCL_{26}$ 85. Pd/C (10 wt. % on activated carbon, 50 mg) was added to a solution of azide-$PEG_{44}$-b-$PCL_{26}$ 84 (200 mg) in EtOH and HOAc (50 μL) after which $H_2$ was bubbled through the solution for 1 hr followed by stirring under an $H_2$ atmosphere for 16 hours. The mixture was filtered, concentrated in vacuum. The residues were then dissolved in THF, recovered by precipitation into cold hexane, and dried under vacuum at room temperature to afford amine-$PEG_{44}$-b-$PCL_{76}$ 85.

DIDO-PEO-PCL copolymer (88). To a stirred solution of carbonic acid 5,6-dihydro-11,12-didehydro-dibenzo[a,e]cycloocten-5-yl ester 4-nitro-phenyl ester 86 (11.6 mg, 0.03 mmol) and copolymer 85 (98 mg, 0.02 mmol) in $CH_2Cl_2$ (10 ml) at room temperature was added $Et_3N$ (0.014 ml, 0.1 mmol). The reaction mixture was stirred overnight at room temperature, after which the solvent was removed under reduced pressure. The residue was purified by size exclusion chromatography (SEC) on LH-20 column (1:1 v/v MeOH/$CH_2Cl_2$) to give the product as yellowish solid (101 mg, 97%).

DIDO-PEO-PCL copolymer (89). To a stirred solution of (5,6-Dihydro-11,12-didehydro-dibenzo[a,e]cycloocten-5-yloxy)-acetic acid 88 (8.3 mg, 0.03 mmol) and copolymer 85 (98 mg, 0.02 mmol) in DMF (15 ml) at room temperature was added HATU coupling reagent (11.4 mg, 0.03 mmol) and DIPEA (0.0104 ml, 0.06 mmol). The reaction mixture was stirred for 5 hours at room temperature, after which the solvent was removed under reduced pressure. The residue was purified by SEC chromatography on LH-20 column (1:1 v/v MeOH/$CF_2Cl_2$) to give the product as yellowish solid (100 mg, 96%).

Cycloadditions of Dibenzocyclooctanol with Various 1,3-Dipoles.

It has been found that 4-dibenzocyclooctynol can react in the absence of catalyst or promoter at ambient temperature with 1,3-dipoles such as nitrones and acyl diazo derivatives, which can provide unique opportunities for bioconjugation reactions.

Nitrones were prepared by a modification of the procedures disclosed in Dicken et al., *J. Org. Chem.* 1982, 47, 2047-2051; and Inouye et al., *Bull. Chem. Soc. Jpn.* 1983, 56, 3541-3542. N-alkylhydroxylamine hydrochloride (10.0 mmol), glyoxylic acid (0.92 g, 10.0 mmol), and sodium bicarbonate (1.68 g, 20.0 mmol) in toluene (20 ml) were stirred at room temperature overnight. The solid was filtered and the filtrate was concentrated to afford the nitrone. This nitrone was then used directly without any purification.

Thus nitrones 91-95 were mixed with 4-dibenzocyclooctynol and after a reaction time of 3 minutes to 3.5 hours the corresponding 2,3-dihydro-issoxazole cycloaddition products were isolated in almost a quantitative yield. It can be seen in FIG. 18 that the chemical nature of the nitrone has a dramatic impact of the reaction rate. In particular electron poor nitrones 93 and 94 react at much faster rates than corresponding azides.

Experimental

General method for calculating second order rate constants by NMR. Substrates were dissolved separately in the appropriate solvent and mixed 1:1 at 6 mM concentrations. Percent conversion was monitored both by disappearance of starting material and appearance of the two regioisomeric products as determined by integration at multiple chemical shifts. Second order rate constants for the reaction were determined by plot-

What is claimed is:

1. An alkyne of the formula:

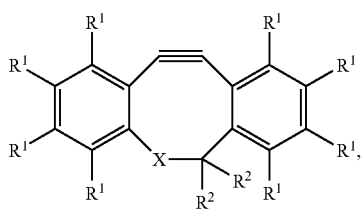

Formula I wherein:
each $R^1$ is independently selected from the group consisting of hydrogen, halogen, hydroxy, alkoxy, nitrate, nitrite, sulfate, and a C1-C10 organic group;
each $R^2$ is independently selected from the group consisting of hydrogen, halogen, hydroxy, alkoxy, nitrate, nitrite, sulfate, and a C1-C10 organic group;
X represents C=O, C=N—$OR^3$, C=N—$NR^3R^4$, $CHOR^3$, or $CHNHR^3$; and
each $R^3$ and $R^4$ independently represents hydrogen or an organic group.

2. The alkyne of claim 1 wherein $R^3$ comprises a covalently bound organic dye.

3. The alkyne of claim 1 wherein X represents C=N—$OR^3$ and $R^3$ represents an organic group having the formula —$(CH_2)_aC(O)Y$, wherein:
a is 1-3;
Y represents OH or $NHR^5$; and
$R^5$ represents hydrogen or a biotinylation product of a primary amine-containing organic group.

4. The alkyne of claim 3 wherein the biotinylation product is the biotinylation product of a primary amine-containing group of the formula —$(CH_2CH_2O)_b(CH_2)_c$-$L_d$-$(CH_2CH_2O)_e(CH_2)_fNH_2$ and/or —$(CD_2CD_2O)_b(CD_2)_c$-$L_d$-$(CD_2CD_2O)_e(CD_2)_fNH_2$, wherein b=0 to 100; c=0 to 100; d=0 to 100; e=0 to 100; f=0 to 100; and L is an optional cleavable linker.

5. The alkyne of claim 4 wherein the cleavable linker, if present, is a disulfide.

6. The alkyne of claim 1 wherein X represents $CHOR^3$ and $R^3$ is selected from the group consisting of an alkyl group, an aryl group, an alkaryl group, and an aralkyl group.

7. The alkyne of claim 6 wherein $R^3$ represents —C(O)Z, wherein:
Z represents an alkyl group, $OR^6$, or $NHR^7$;
$R^6$ and $R^7$ are each independently selected from the group consisting of an alkyl group, an aryl group, an alkaryl group, and an aralkyl group.

8. An alkyne of the formula:

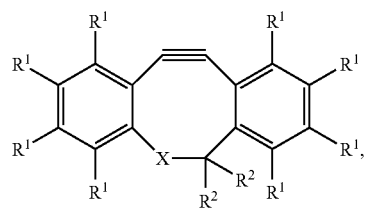

Formula I wherein:
each $R^1$ is independently selected from the group consisting of hydrogen, halogen, hydroxy, alkoxy, nitrate, nitrite, sulfate, and a C1-C10 organic group;
each $R^2$ is independently selected from the group consisting of hydrogen, halogen, hydroxy, alkoxy, nitrate, nitrite, sulfate, and a C1-C10 organic group;
X represents $CHOR^3$;
$R^3$ represents —C(O)Z, wherein:
Z represents an alkyl group, $OR^6$, or $NHR^7$;
$R^6$ is selected from the group consisting of an alkyl group, an aryl group, an alkaryl group, and an aralkyl group; and
$R^7$ is a biotinylation product of a primary amine-containing organic group.

9. The alkyne of claim 8 wherein the biotinylation product is the biotinylation product of a primary amine-containing group of the formula —$(CH_2CH_2O)_b(CH_2)_c$-$L_d$-$(CH_2CH_2O)_e(CH_2)_fNH_2$ and/or —$(CD_2CD_2O)_b(CD_2)_c$-$L_d$-$(CD_2CD_2O)_e(CD_2)_fNH_2$, wherein b=0 to 100; c=0 to 100; d=0 to 100; e=0 to 100; f=0 to 100; and L is an optional cleavable linker.

10. The alkyne of claim 9 wherein the cleavable linker, if present, is a disulfide.

11. An alkyne of the formula:

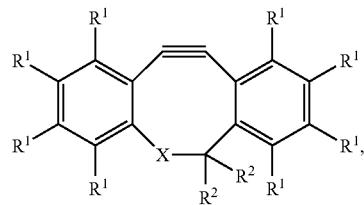

Formula I wherein:
each $R^1$ is independently selected from the group consisting of hydrogen, halogen, hydroxy, alkoxy, nitrate, nitrite, sulfate, and a C1-C10 organic group;
each $R^2$ is independently selected from the group consisting of hydrogen, halogen, hydroxy, alkoxy, nitrate, nitrite, sulfate, and a C1-C10 organic group;
X represents C=O, C=N—$OR^3$, C=N—$NR^3R^4$, $CHOR^3$, or $CHNHR^3$;
$R^3$ represents a polymeric or a copolymeric group; and
$R^4$ represents hydrogen or an organic group.

12. The alkyne of claim 11 wherein the copolymeric group comprises a hydrophilic segment and a hydrophobic segment.

13. The alkyne of claim 11 wherein the copolymeric group comprises a fragment of the formula —$[CH_2CH_2O]_n[C(O)(CH_2)_5O]_m$—H, wherein n=0 to 100 and m=0 to 100.

14. An alkyne of the formula:

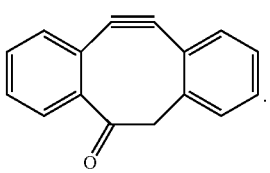

Formula IV

15. An alkyne of the formula:

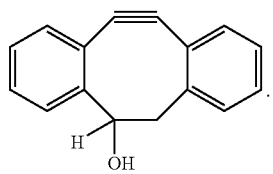

Formula V

16. An alkyne of the formula:

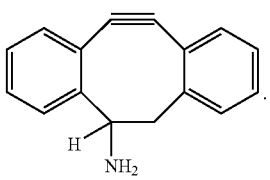

Formula VI

17. An alkyne of the formula:

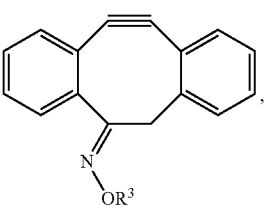

Formula VII wherein $R^3$ represents hydrogen or an organic group.

18. A composition comprising a blend of:
   an alkyne according to claim 11; and
   a polymer or a copolymer.

19. The composition of claim 18 wherein the composition forms a copolymer micelle.

20. A method for controlling the delivery of drugs, the method comprising:
   combining at least one 1,3-dipole-functional drug with a copolymer micelle according to claim 19 comprising an alkyne; and
   allowing the at least one 1,3-dipole-functional drug and the copolymer micelle comprising the alkyne to react under conditions effective to form a heterocyclic compound.

21. A method of preparing a heterocyclic compound, the method comprising:
   combining at least one 1,3-dipole-functional compound with at least one alkyne according to claim 1; and
   allowing the at least one 1,3-dipole-functional compound and the at least one alkyne to react under conditions effective to form the heterocyclic compound.

22. A substrate having on the surface thereof an alkyne according to claim 1.

23. A method of immobilizing a biomolecule on a substrate, the method comprising:
   providing a substrate according claim 22;
   contacting the substrate with a 1,3-dipole-functional biomolecule under conditions effective to form a heterocyclic compound.

24. A method for immobilizing a cell, the method comprising:
   providing a substrate according to claim 22;
   contacting the substrate with a cell comprising a 1,3-dipole-functional biomolecule under conditions effective to form a heterocyclic compound.

* * * * *